US012751952B2

(12) United States Patent
Zhang et al.

(10) Patent No.: US 12,751,952 B2
(45) Date of Patent: Oct. 6, 2026

(54) QUINAZOLINE DERIVATIVE, OR PREPARATION METHOD THEREFOR AND USE THEREOF

(71) Applicants: Zhejiang Hisun Pharmaceutical Co., Ltd., Taizhou (CN); Shanghai Aryl Pharmtech Co., Ltd., Shanghai (CN)

(72) Inventors: Panpan Zhang, Taizhou (CN); Chaoying Cheng, Taizhou (CN); Zhipeng He, Taizhou (CN); Chengcai Lin, Taizhou (CN); Linjiang Shao, Taizhou (CN); Cheng Ye, Shanghai (CN); Wenjian Qian, Taizhou (CN); Lei Chen, Taizhou (CN)

(73) Assignees: Zhejiang Hisun Pharmaceutical Co., Ltd., Taizhou (CN); Shanghai Aryl Pharmtech Co., Ltd., Shanghai (CN)

( * ) Notice: Subject to any disclaimer, the term of this patent is extended or adjusted under 35 U.S.C. 154(b) by 359 days.

(21) Appl. No.: 18/686,997

(22) PCT Filed: Aug. 29, 2022

(86) PCT No.: PCT/CN2022/115379

§ 371 (c)(1),
(2) Date: Feb. 27, 2024

(87) PCT Pub. No.: WO2023/030216

PCT Pub. Date: Mar. 9, 2023

(65) Prior Publication Data

US 2024/0382475 A1 Nov. 21, 2024

(30) Foreign Application Priority Data

| | | |
|---|---|---|
| Aug. 30, 2021 | (CN) | 202111003188.1 |
| Nov. 10, 2021 | (CN) | 202111325366.2 |
| Jan. 26, 2022 | (CN) | 202210090957.4 |
| Apr. 22, 2022 | (CN) | 202210428769.8 |

(51) Int. Cl.

*A61K 31/4709* (2006.01)
*A61P 35/00* (2006.01)

(52) U.S. Cl.

CPC .......... *A61K 31/4709* (2013.01); *A61P 35/00* (2018.01)

(58) Field of Classification Search

CPC .............................. A61K 31/517; A61P 35/00
See application file for complete search history.

(56) References Cited

U.S. PATENT DOCUMENTS

2019/0358230 A1 11/2019 Gmachl et al.

FOREIGN PATENT DOCUMENTS

| | | | |
|---|---|---|---|
| CN | 101619043 | A | 1/2010 |
| CN | 110167928 | A | 8/2019 |
| WO | 2010002845 | A2 | 1/2010 |
| WO | 2021105960 | A1 | 6/2021 |

OTHER PUBLICATIONS

Ju. Hou et al. "Design. synthesis. anti-tumor activity. and molecular modeling of quinazoline and pyrido[2. 3-d] pyrimidine derivatives targeting epidermal growth factor receptor" European Journal of Medicinal Chemistry, vol. 118, Apr. 20, 2016 (Apr. 20, 2016), pp. 276-289.

Xu. Yanzhao et al., "Research Progress of KRAS Inhibitors", Acta Pharmaceutica Sinica, vol. 56. No. 6. Jan. 29, 2021 (Jan. 29, 2021). pp. 1562-1570.

International Search Report for Application No. PCT/CN2022/115379 mailed Nov. 29, 22. 4 pgs.

*Primary Examiner* — Alicia L Otton
(74) *Attorney, Agent, or Firm* — Lerner David LLP

(57) ABSTRACT

The present invention relates to a substituted quinazoline derivative, a preparation method therefor, a pharmaceutical composition comprising the derivative, and use of the quinazoline derivative or a composition thereof in medicine. Specifically, the present invention relates to substituted quinazoline derivative represented by general formula (I), a preparation method therefor, a pharmaceutically acceptable salt thereof, and use thereof as therapeutic agents, in particular as SOS1 inhibitors. The definition of each substituent in general formula (I) is the same as the definition in the description.

20 Claims, 1 Drawing Sheet

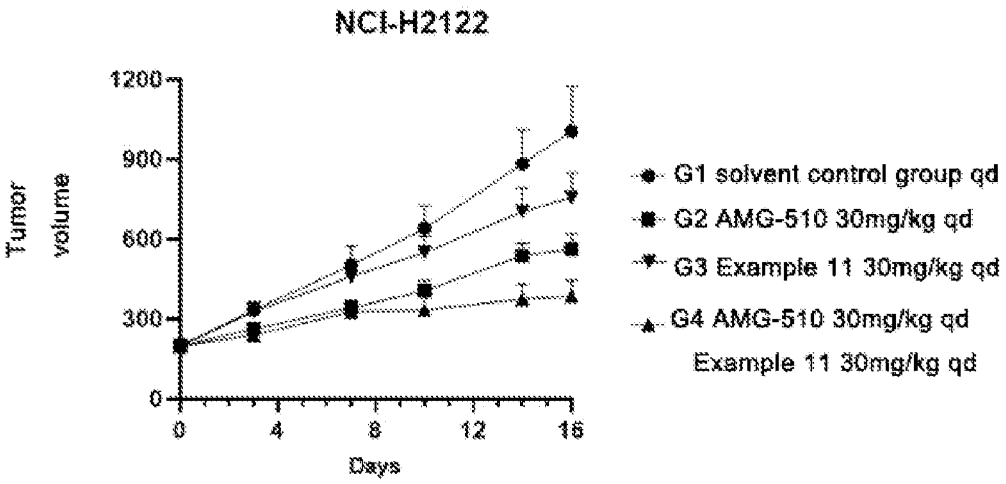
NCI-H2122
Tumor volume
1200
900
600
300
0
0
4
8
12
16
Days
G1 solvent control group qd
G2 AMG-510 30mg/kg qd
G3 Example 11 30mg/kg qd
G4 AMG-510 30mg/kg qd Example 11 30mg/kg qd

QUINAZOLINE DERIVATIVE, OR PREPARATION METHOD THEREFOR AND USE THEREOF

CROSS-REFERENCE TO RELATED APPLICATIONS

The present application is a U.S. National entry under 35 U.S.C. § 371 of International Application No. PCT/CN2022/115379, filed Aug. 29, 2022, which claims the benefit of, and priority to Chinese Patent Application Nos. 202111003188.1, filed Aug. 30, 2021, 202111325366.2, filed Nov. 10, 2021, 202210090957.4, filed Jan. 26, 2022 and 202210428769.9, filed Apr. 22, 2022 in the China National Intellectual property Administration, the disclosures of which are hereby incorporated by reference in its entirety.

TECHNICAL FIELD

The present invention relates to a substituted quinazoline derivative, a preparation method therefor, a pharmaceutical composition comprising the derivative and use of the derivative as a therapeutic agent, in particular as an SOS1 inhibitor.

BACKGROUND

RAS genes are widely found in various eukaryotes such as mammals, fruit flies, fungi, nematodes and yeasts, and have important physiological functions in various life systems. There are three members in the mammalian RAS gene family, namely H-RAS, K-RAS and N-RAS. Various RAS genes have similar structures and are all composed of four exons distributed over a DNA of about 30 kb in length. Their encoded products are monomeric globular proteins with a relative molecular mass of 21 kDa. The activated and inactivated states of RAS proteins have a significant impact on life processes of cells such as growth, differentiation, proliferation and apoptosis. This protein is a membrane-bound guanine nucleotide-binding protein with weak GTPase activity. In normal physiological activities, the activity status of RAS is regulated by GTPase-activating proteins (GAPs) and guanine nucleotide exchange factors (GEFs). When RAS protein combines with GTP to form RAS-GTP, the protein is in an activated state. GTPase activating protein can dephosphorylate RAS-GTP and convert RAS-GTP into RAS-GDP, thereby inactivating it; inactive RAS-GDP is converted into active RAS-GTP under the action of guanine nucleotide exchange factor, thereby activating a series of downstream pathways such as RAF/MER/ERK and PI3K/AKT/mTOR.

The RAS genes are also closely related to various human diseases, especially cancers. RAS is a frequently mutated oncogene, wherein, KRAS subtype gene mutations account for 86% of the total RAS gene mutations. Varying degrees of KRAS gene mutations are found in about 90% of pancreatic cancer, 30%-40% of colon cancer, and 15-20% of lung cancer. Due to the prevalence of KRAS gene mutations, this target has always been the focus of drug developers. Starting from the announcement of the clinical results of AMG-510, which directly acts on the KRAS-G12C target, research on KRAS inhibitors has set off an upsurge at home and abroad.

SOS (Son of sevenless homolog) protein was first discovered in fruit flies research and was a guanosine-releasing protein encoded by the SOS gene. There are two SOS homologues in humans, hSOS1 and hSOS2, both of which are members of the guanine nucleotide exchange factor family and share 70% homology. Although they are highly similar in structure and sequence, there are certain differences in their physiological functions. The hSOS1 protein is 150 kDa in size and is a multi-structured protein domain composed of 1333 amino acids, including an N-terminal protein domain, multiple homodomains (HD), a helical linker (HL), a RAS exchanger motif (REM), and a proline-rich C-terminal domain. There are two binding sites on hSOS1 that bind to RAS protein, namely the catalytic site and the allosteric site. The catalytic site binds to the RAS protein on the RAS-GDP complex to promote guanine nucleotide exchange, and the allosteric site binds to the RAS protein on the RAS-GTP complex to further enhance the catalytic effect, thereby participating in and activating the signal transduction of RAS family proteins. Studies have shown that inhibition of SOS1 not only completely inhibits the RAS-RAF-MEK-ERK pathway in wild-type KRAS cells, but also causes a 50% reduction in phospho-ERK activity in mutant KRAS cell lines. Therefore, inhibition of SOS1 can also reduce the activity of RAS, thereby treating various cancers caused by RAS gene mutations or excessive activation of RAS protein, including pancreatic cancer, colorectal cancer, bile duct cancer, gastric cancer, non-small cell lung cancer, etc.

In addition, changes in SOS1 are also involved in cancers. Studies have shown that SOS1 mutations are found in embryonal rhabdomyosarcoma, Sertoli cell testicular tumors, diffuse large B-cell lymphoma, neurofibroma, cutaneous granular cell tumor, and lung adenocarcinoma. Meanwhile, studies have described overexpression of SOS1 in bladder cancer and prostate cancer. In addition to cancer, inherited SOS1 mutations have also been involved in the pathogenesis of RAS pathologies such as Noonan syndrome (NS), cardio-facio-cutaneous syndrome (CFC), and type I hereditary gingival fibromatosis.

SOS1 is also the GEF used to activate the GTPase RAC1 (Ras-related C3 botulinum toxin substrate 1). Like RAS family proteins, RAC1 is involved in the pathogenesis of multiple human cancers and other diseases.

There are no drugs that selectively target SOS1 on the market, but a series of related patents have been published, including WO2018115380A1, WO2019122129A1 of BI, WO2019201848A1 of Bayer, WO2020180768A1, WO2020180770A1 of Revolution, etc., the drug currently in clinical trials is BI-1701963, and the drug in preclinical stage is BI-3406. However, these are far from enough for anti-tumor research. Research and development of new selective SOS1 kinase inhibitors remains necessary to address unmet medical needs.

SUMMARY

In response to the above technical problems, the present invention provides a substituted quinazoline compound represented by general formula (I) or a stereoisomer, a tautomer or a pharmaceutically acceptable salt thereof:

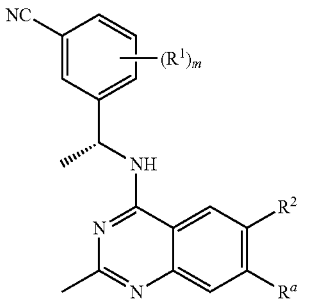

(I)

wherein:

$R^a$ is cyano, —C(O)$R^3$ or $C_1$-$C_6$ alkoxy;

$R^1$ are the same or different, and are each independently halogen, hydroxyl, amino, $C_1$-$C_6$ alkyl or $C_1$-$C_6$ alkoxy; wherein, the alkyl or alkoxy is optionally further substituted by one or more substituents selected from halogen, hydroxyl, cyano, amino, $C_1$-$C_6$ alkyl and $C_1$-$C_6$ alkoxy; $R^1$ is preferably $C_1$-$C_6$ alkyl; more preferably methyl;

$R^2$ is $C_3$-$C_6$ cycloalkyl, 3-6 membered monocyclic heterocyclyl, 6-11 membered spiroheterocyclyl, 6-11 membered bridged heterocyclyl, 6-11 membered fused heterocyclyl or 6-11 membered fused ring; wherein, the cycloalkyl, monocyclic heterocyclyl, spiroheterocyclyl, bridged heterocyclyl, fused heterocyclyl or fused ring is optionally further substituted by one or more $R^A$s.

$R^A$ is each independently halogen, cyano, hydroxyl, amino, oxo, $C_1$-$C_6$ alkyl, $C_1$-$C_6$ alkoxy, $C_3$-$C_6$ cycloalkyl, 3-8 membered heterocyclyl, —C(O)$R^3$ or —$SO_2R^4$, wherein, the alkyl, alkoxy or cycloalkyl is optionally further substituted by one or more substituents selected from halogen, nitro, cyano, hydroxyl, amino, $C_1$-$C_6$ alkyl, $C_3$-$C_6$ cycloalkyl, $C_1$-$C_6$ alkoxy and —$SO_2R^4$; the heterocyclyl is optionally further substituted by one or more substituents selected from halogen, nitro, cyano, hydroxyl, amino, oxo, $C_1$-$C_6$ alkyl, $C_3$-$C_6$ cycloalkyl, $C_1$-$C_6$ alkoxy, —C(O)$R^3$ and —$SO_2R^4$;

$R^3$ is each independently $C_1$-$C_6$ alkyl, $C_1$-$C_3$ alkoxy, $C_3$-$C_6$ cycloalkyl, —$NR^5R^6$ or 3-6 membered heterocyclyl, wherein, the alkyl or cycloalkyl is optionally further substituted by one or more substituents selected from hydroxyl, halogen, nitro, amino, cyano, $C_1$-$C_6$ alkyl, $C_1$-$C_6$ alkoxy, $C_1$-$C_6$ haloalkyl and $C_1$-$C_6$ haloalkoxy; the heterocyclyl is optionally further substituted by one or more substituents selected from hydroxyl, halogen, nitro, amino, cyano, oxo, $C_1$-$C_6$ alkyl, $C_1$-$C_6$ alkoxy, $C_1$-$C_6$ haloalkyl and $C_1$-$C_6$ haloalkoxy;

$R^4$ is each independently amino, $C_1$-$C_6$ alkyl or $C_3$-$C_6$ cycloalkyl;

$R^5$ and $R^6$ are each independently a hydrogen atom or $C_1$-$C_6$ alkyl, wherein, the alkyl is optionally further substituted by one or more substituents selected from hydroxyl, halogen, amino, cyano and $C_1$-$C_6$ alkoxy;

or, $R^5$ and $R^6$ together with the N atom bound therewith form a 4-10 membered heterocyclic ring, the formed heterocyclic ring is optionally further substituted with a substituent selected from halogen, cyano, hydroxyl, amino, oxo, $C_1$-$C_6$ alkyl, $C_1$-$C_6$ alkoxy, —C(O)$R^7$ and $C_3$-$C_6$ cycloalkyl;

$R^7$ is $C_1$-$C_3$ alkyl or $C_3$-$C_6$ cycloalkyl, the alkyl or cycloalkyl is optionally further substituted by one or more substituents selected from hydroxyl, halogen, amino, cyano and $C_1$-$C_6$ alkoxy; and m is 0, 1, 2, 3 or 4.

In one or more embodiments of the present application, the compound represented by general formula (I) or the stereoisomer, the tautomer, or the pharmaceutically acceptable salt thereof, is a compound represented by general formula (II) or a stereoisomer, a tautomer, or a pharmaceutically acceptable salt thereof:

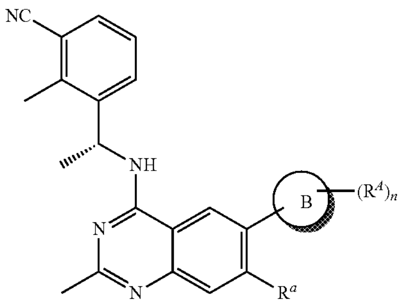

(II)

wherein:

$R^a$ is cyano, acetyl or methoxy;

ring B is $C_3$-$C_6$ cycloalkyl, 3-6 membered monocyclic heterocyclyl, 6-11 membered spiroheterocyclyl, 6-11 membered bridged heterocyclyl, 6-11 membered fused heterocyclyl or 6-11 membered fused ring;

$R^A$ is each independently halogen, cyano, hydroxyl, amino, oxo, $C_1$-$C_6$ alkyl, $C_1$-$C_6$ alkoxy, $C_3$-$C_6$ cycloalkyl, 3-8 membered heterocyclyl, —C(O)$R^3$ or —$SO_2R^4$, wherein, the alkyl, alkoxy or cycloalkyl is optionally further substituted by one or more substituents selected from halogen, nitro, cyano, hydroxyl, amino, $C_1$-$C_6$ alkyl, $C_3$-$C_6$ cycloalkyl, $C_1$-$C_6$ alkoxy and —$SO_2R^4$; the heterocyclyl is optionally further substituted by one or more substituents selected from halogen, nitro, cyano, hydroxyl, amino, oxo, $C_1$-$C_6$ alkyl, $C_3$-$C_6$ cycloalkyl, $C_1$-$C_6$ alkoxy, —C(O)$R^3$ and —$SO_2R^4$;

$R^3$ is $C_1$-$C_6$ alkyl, $C_1$-$C_3$ alkoxy, $C_3$-$C_6$ cycloalkyl, —$NR^5R^6$ or 3-6 membered heterocyclyl; wherein, the alkyl or cycloalkyl is optionally further substituted by one or more substituents selected from halogen, cyano and $C_1$-$C_6$ alkyl; the heterocyclyl is optionally further substituted by one or more substituents selected from halogen, cyano, oxo and $C_1$-$C_6$ alkyl;

$R^4$ is each independently amino, $C_1$-$C_6$ alkyl or $C_3$-$C_6$ cycloalkyl;

$R^5$ and $R^6$ are each independently a hydrogen atom or $C_1$-$C_6$ alkyl, wherein, the alkyl is optionally further substituted by one or more substituents selected from hydroxyl, halogen, amino, cyano and $C_1$-$C_6$ alkoxy;

or, $R^5$ and $R^6$ together with the N atom bound therewith form a 4-10 membered heterocyclic ring, the formed heterocyclic ring is optionally further substituted with a substituent selected from halogen, cyano, hydroxyl, amino, oxo, $C_1$-$C_6$ alkyl, $C_1$-$C_6$ alkoxy, —C(O)$R^7$ and $C_3$-$C_6$ cycloalkyl;

$R^7$ is $C_1$-$C_3$ alkyl or $C_3$-$C_6$ cycloalkyl, the alkyl or cycloalkyl is optionally further substituted by one or more substituents selected from hydroxyl, halogen, amino, cyano and $C_1$-$C_6$ alkoxy; and n is 0, 1, 2 or 3.

In one or more embodiments of the present application, in the compound represented by general formula (II) or the stereoisomer, the tautomer, or the pharmaceutically acceptable salt thereof, ring B is the following group:

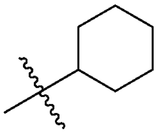
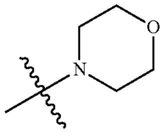
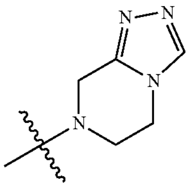
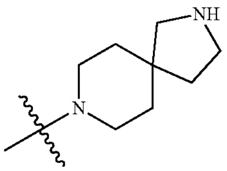
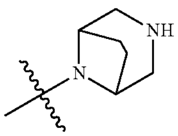
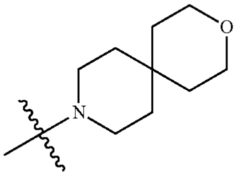
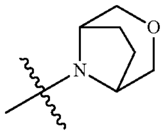
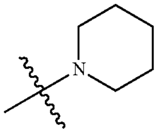
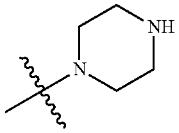
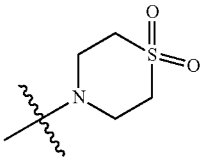
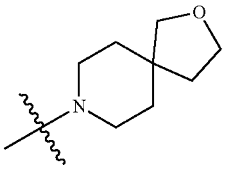
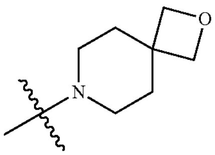
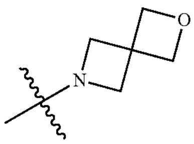
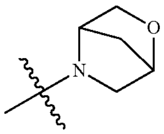
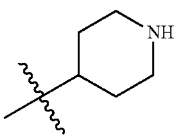
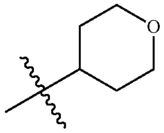
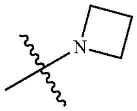
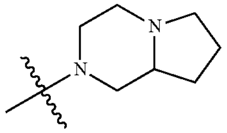
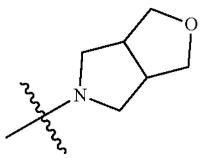
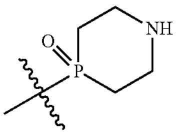
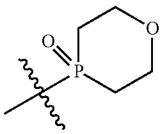

-continued

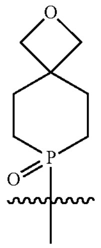
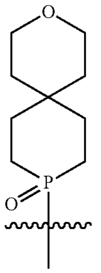
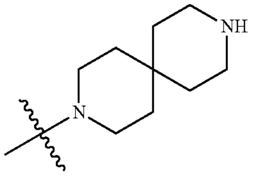

or

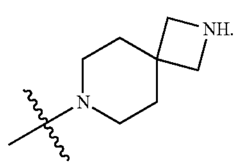

In one or more embodiments of the present application, in the compound represented by general formula (II) or the stereoisomer, the tautomer, or the pharmaceutically acceptable salt thereof,

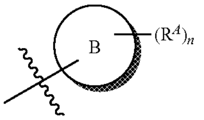

is the following group:

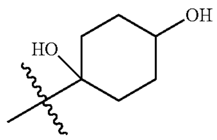
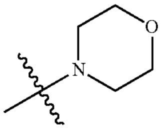
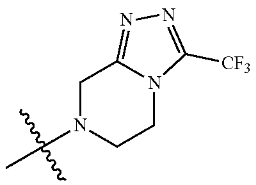
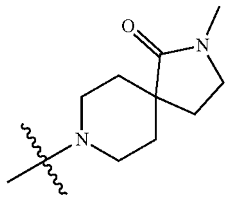
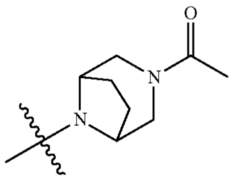
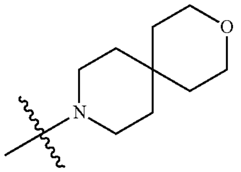
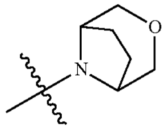
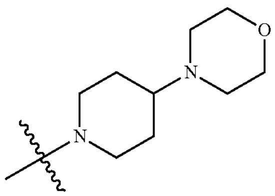

-continued
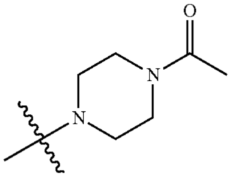
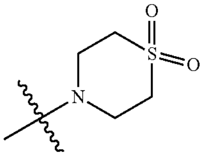
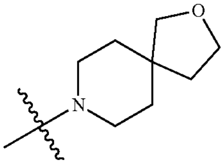
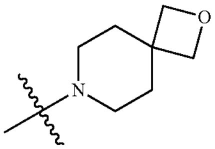
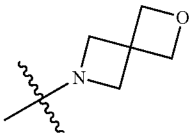
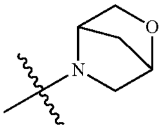
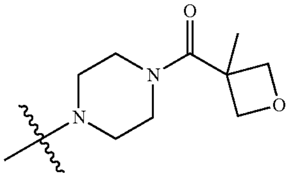
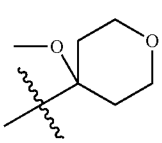
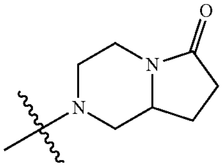
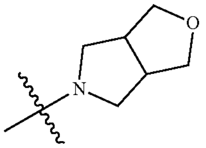
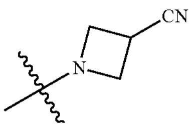
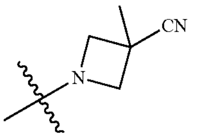
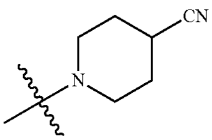
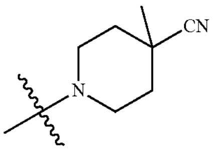
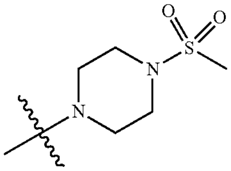
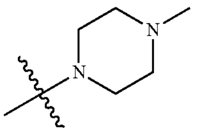
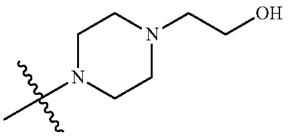
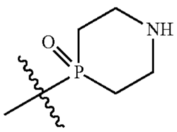
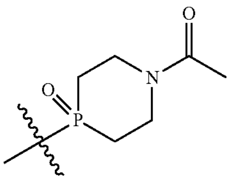
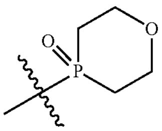
-continued
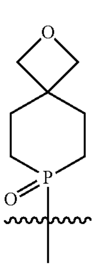
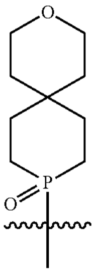
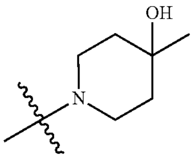
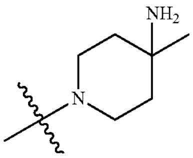
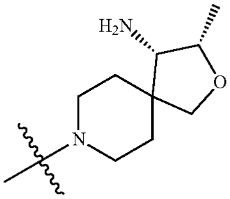
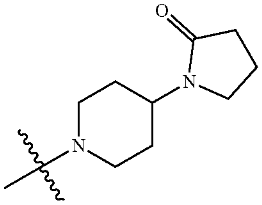
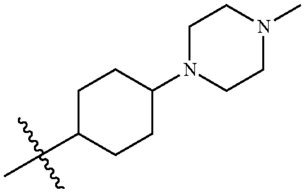
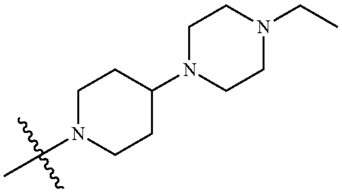
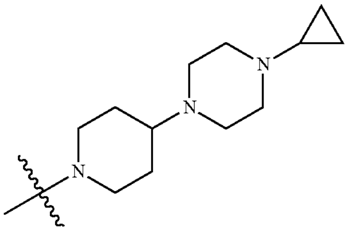
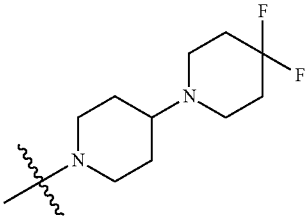
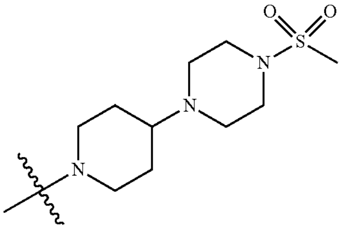

-continued
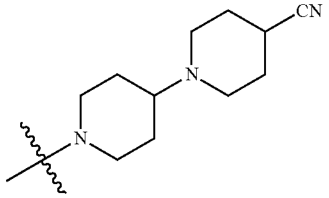
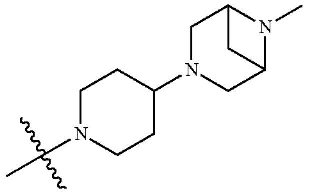
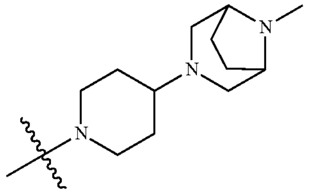
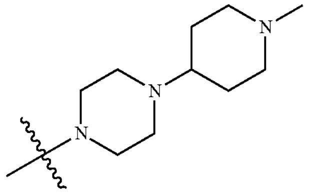
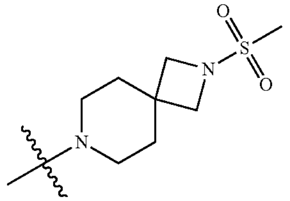
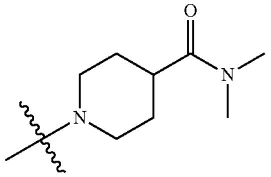
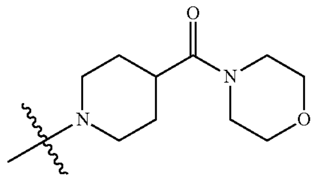
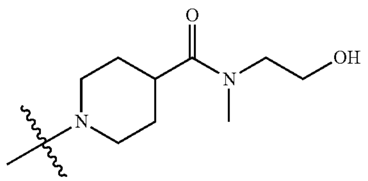
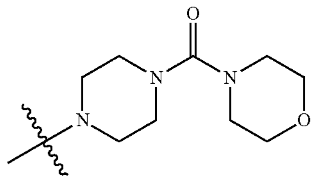
-continued
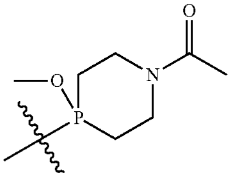
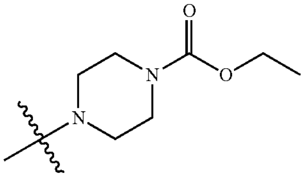
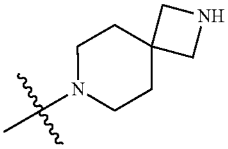
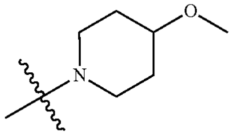
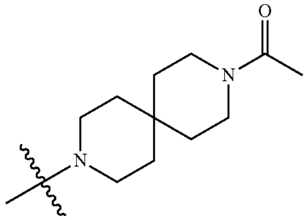
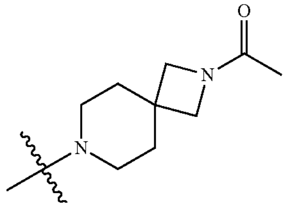
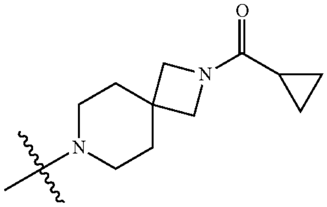
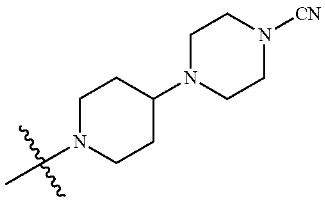
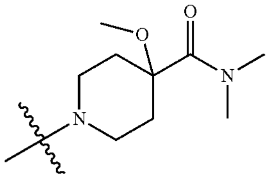
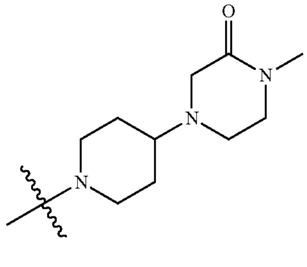
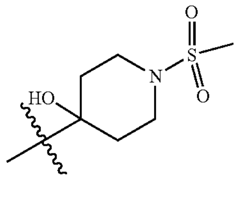

-continued

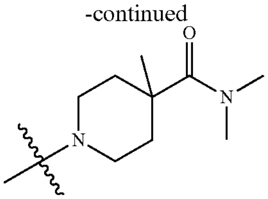

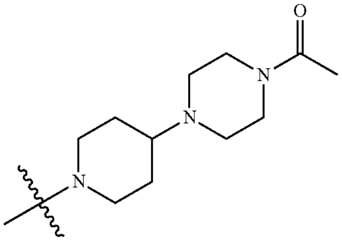

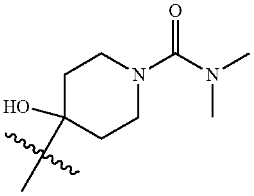

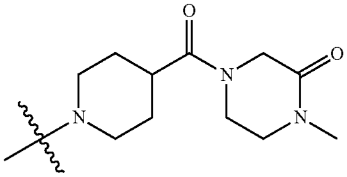

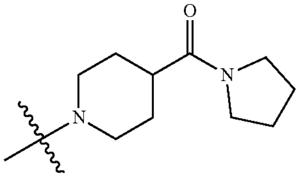

-continued

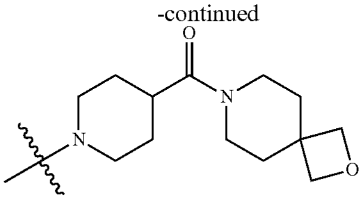

or

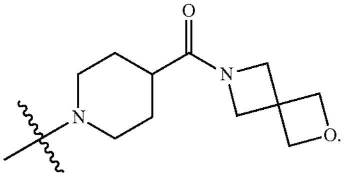

In one or more embodiments of the present application, in the compound represented by general formula (I) or the stereoisomer, the tautomer, or the pharmaceutically acceptable salt thereof, $R^1$ is methyl.

In one or more embodiments of the present application, in the compound represented by general formula (I) or (II) or the stereoisomer, the tautomer, or the pharmaceutically acceptable salt thereof, $R^a$ is methoxy.

In one or more embodiments of the present application, in the compound represented by general formula (I) or (II) or the stereoisomer, the tautomer, or the pharmaceutically acceptable salt thereof, $R^a$ is acetyl.

In one or more embodiments of the present application, the compound of formula (I) is:

| Compound number | Structure | Name |
|---|---|---|
| 1 | 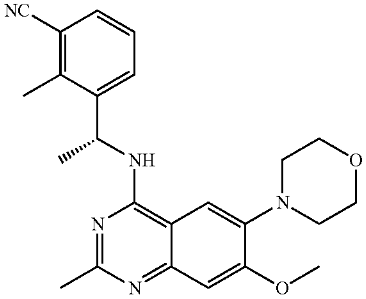 [SMILES: COc1cc2nc(C)nc(N[C@H](C)c3cccc(C#N)c3C)c2cc1N1CCOCC1] | (R)-3-(1-((7-methoxy-2-methyl-6-morpholinoquinazolin-4-yl)amino)ethyl)-2-methylbenzonitrile |
| 2 | 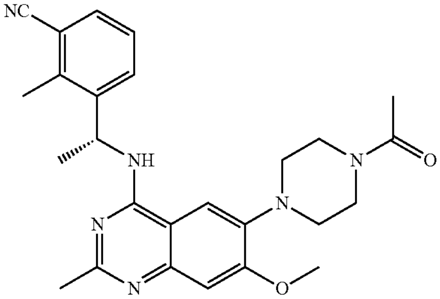 [SMILES: COc1cc2nc(C)nc(N[C@H](C)c3cccc(C#N)c3C)c2cc1N1CCN(C(C)=O)CC1] | (R)-3-(1-((6-(4-acetylpiperazin-1-yl)-7-methoxy-2-methylquinazolin-4-yl)amino)ethyl)-2-methylbenzonitrile |

-continued

| Compound number | Structure | Name |
|---|---|---|
| 3 | 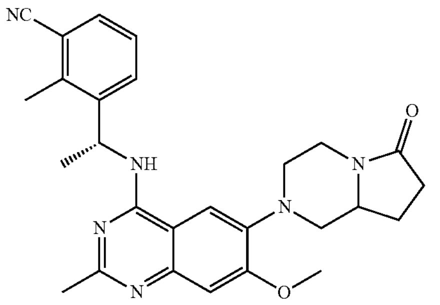 [SMILES: COc1cc2nc(C)nc(N[C@H](C)c3cccc(C#N)c3C)c2cc1N1CCN2C(=O)CCC2C1] | 3-((1R)-1-((7-methoxy-2-methyl-6-(6-oxo hexahydropyrrolo[1,2-a]pyrazin-2(1H)-yl) quinazolin-4-yl)amino)ethyl)-2-methylbenzonitrile |
| 4 | 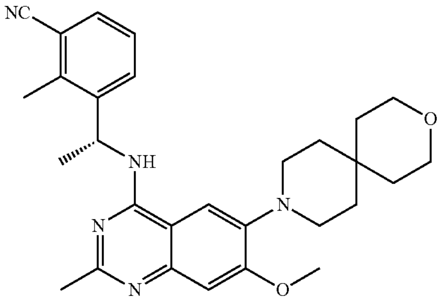 [SMILES: COc1cc2nc(C)nc(N[C@H](C)c3cccc(C#N)c3C)c2cc1N1CCC2(CCOCC2)CC1] | (R)-3-(1-((7-methoxy-2-methyl-6-(3-oxa-9-azaspiro[5.5]undecan-9-yl)quinazolin-4-yl) amino)ethyl)-2-methylbenzonitrile |
| 5 | 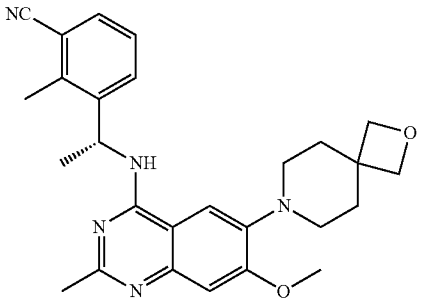 [SMILES: COc1cc2nc(C)nc(N[C@H](C)c3cccc(C#N)c3C)c2cc1N1CCC2(CC1)COC2] | (R)-3-(1-((7-methoxy-2-methyl-6-(2-oxa-7-azaspiro[3.5]nonan-7-yl)quinazolin-4-yl) amino)ethyl)-2-methylbenzonitrile |
| 6 | 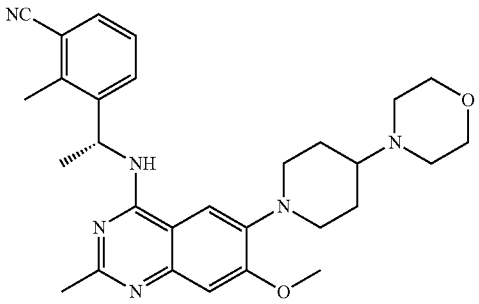 [SMILES: COc1cc2nc(C)nc(N[C@H](C)c3cccc(C#N)c3C)c2cc1N1CCC(N2CCOCC2)CC1] | (R)-3-(1-((7-methoxy-2-methyl-6-(4-morpholinopiperidin-1-yl)quinazolin-4-yl) amino)ethyl)-2-methylbenzonitrile |
| 7 | 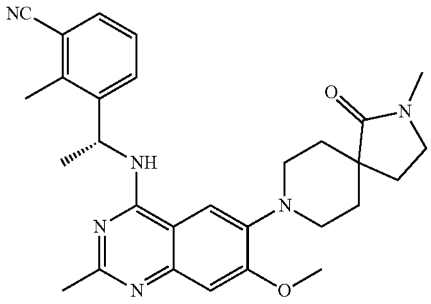 [SMILES: COc1cc2nc(C)nc(N[C@H](C)c3cccc(C#N)c3C)c2cc1N1CCC2(CCN(C)C2=O)CC1] | (R)-3-(1-((7-methoxy-2-methyl-6-(2-methyl-1-oxo-2,8-diazaspiro[4.5]decan-8-yl)quinazolin-4-yl)amino)ethyl)-2-methylbenzonitrile |

-continued

| Compound number | Structure | Name |
|---|---|---|
| 8 | 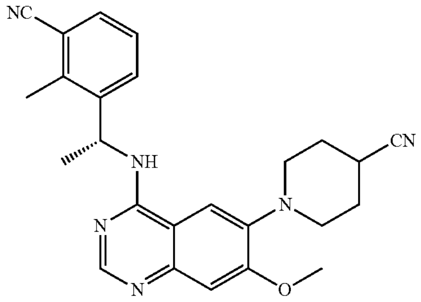 [SMILES: COc1cc2ncnc(N[C@H](C)c3cccc(C#N)c3C)c2cc1N1CCC(C#N)CC1] | (R)-1-(4-((1-(3-cyano-2-methylphenyl) ethyl)amino)-7-methoxy-2-methylquinazolin-6-yl)piperidine-4-carbonitrile |
| 9 | 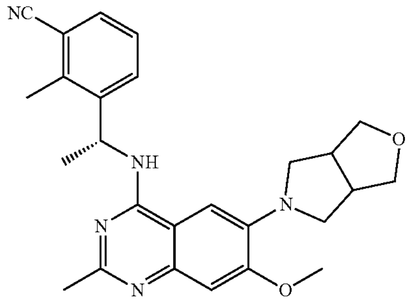 [SMILES: COc1cc2nc(C)nc(N[C@H](C)c3cccc(C#N)c3C)c2cc1N1CC2COCC2C1] | 3-((1R)-1-((7-methoxy-2-methyl-6-(tetrahydro-1H-furo[3,4-c]pyrrol-5(3H)-yl) quinazolin-4-yl)amino)ethyl)-2-methylbenzonitrile |
| 10 | 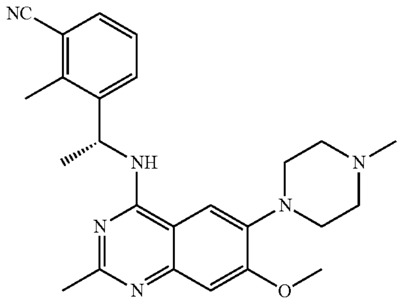 | (R)-3-(1-((7-methoxy-2-methyl-6-(4-methylpiperazin-1-yl)quinazolin-4-yl)amino) ethyl)-2-methylbenzonitrile |
| 11 | 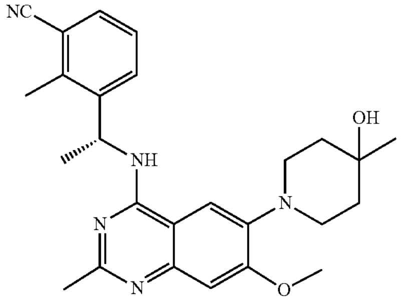 | (R)-3-(1-((6-(4-hydroxy-4-methylpiperidin-1-yl)-7-methoxy-2-methylquinazolin-4-yl) amino)ethyl)-2-methylbenzonitrile |
| 12 | 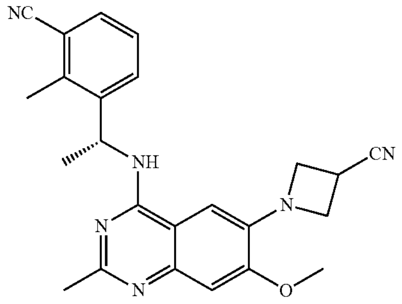 [SMILES: COc1cc2nc(C)nc(N[C@H](C)c3cccc(C#N)c3C)c2cc1N1CC(C#N)C1] | (R)-1-(4-((1-(3-cyano-2-methylphenyl) ethyl)amino)-7-methoxy-2-methylquinazolin-6-yl)azetidine-3-carbonitrile |

-continued

| Compound number | Structure | Name |
|---|---|---|
| 13 | 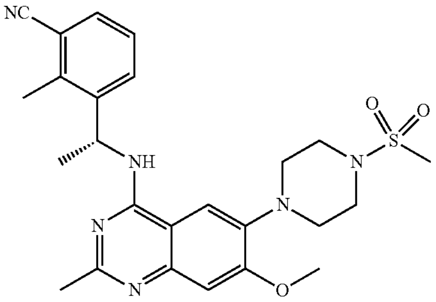 | (R)-3-(1-((7-methoxy-2-methyl-6-(4-(methylsulfonyl)piperazin-1-yl)quinazolin-4-yl)amino)ethyl)-2-methylbenzonitrile |
| 14 | 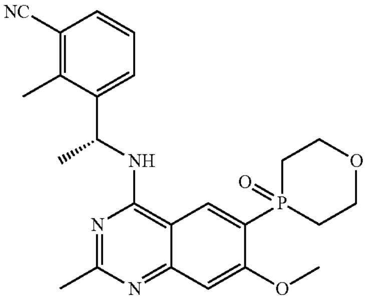 [SMILES: COc1cc2nc(C)nc(N[C@H](C)c3cccc(C#N)c3C)c2cc1P1(=O)CCOCC1] | (R)-3-(1-((7-methoxy-2-methyl-6-(4-oxido-1,4-oxaphosphinan-4-yl)quinazolin-4-yl)amino)ethyl)-2-methylbenzonitrile |
| 15 | 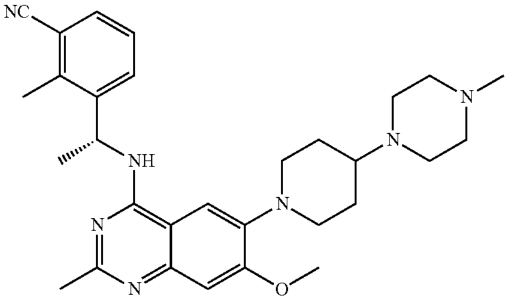 | (R)-3-(1-((7-methoxy-2-methyl-6-(4-(4-methylpiperazin-1-yl)piperidin-1-yl)quinazolin-4-yl)amino)ethyl)-2-methylbenzonitrile |
| 16 | 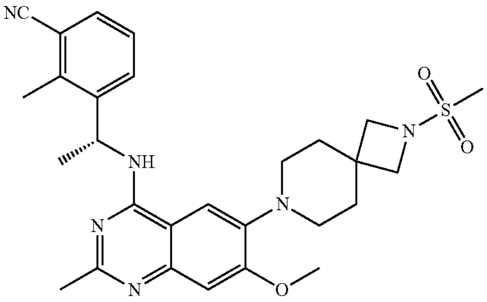 | (R)-3-(1-((7-methoxy-2-methyl-6-(2-(methylsulfonyl)-2,7-diazaspiro[3.5]nonan-7-yl)quinazolin-4-yl)amino)ethyl)-2-methylbenzonitrile |
| 16c | 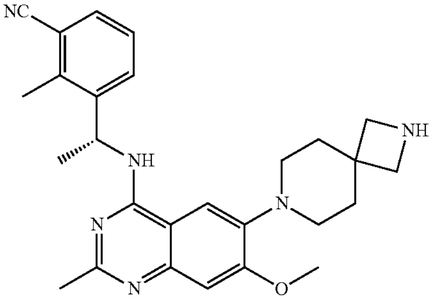 [SMILES: COc1cc2nc(C)nc(N[C@H](C)c3cccc(C#N)c3C)c2cc1N1CCC2(CC1)CNC2] | (R)-3-(1-((7-methoxy-2-methyl-6-(2,7-diazaspiro[3.5]nonan-7-yl)quinazolin-4-yl)amino)ethyl)-2-methylbenzonitrile |

-continued

| Compound number | Structure | Name |
|---|---|---|
| 17 | 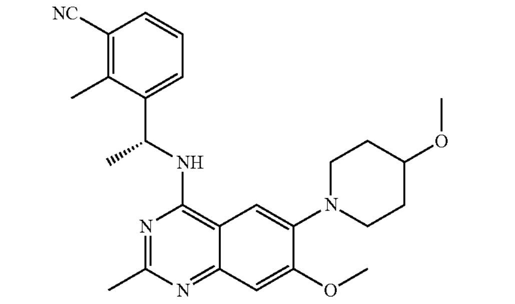 | (R)-3-(1-((7-methoxy-6-(4-methoxypiperidin-1-yl)-2-methylquinazolin-4-yl)amino) ethyl)-2-methylbenzonitrile |
| 18 | 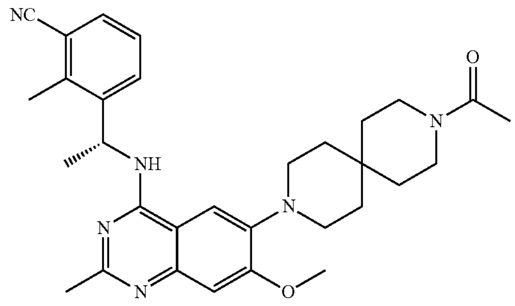 [SMILES: COc1cc2nc(C)nc(N[C@H](C)c3cccc(C#N)c3C)c2cc1N1CCC2(CCN(C(C)=O)CC2)CC1] | (R)-3-(1-((6-(9-acetyl-3,9-diazaspiro[5.5] undecan-3-yl)-7-methoxy-2-methylquinazolin-4-yl)amino)ethyl)-2-methylbenzonitrile |
| 19 | 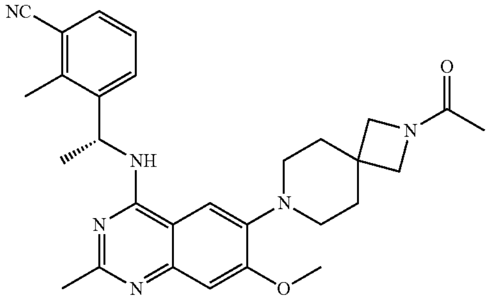 [SMILES: COc1cc2nc(C)nc(N[C@H](C)c3cccc(C#N)c3C)c2cc1N1CCC2(CC1)CN(C(C)=O)C2] | (R)-3-(1-((6-(2-acetyl-2,7-diazaspiro[3.5] nonan-7-yl)-7-methoxy-2-methylquinazolin-4-yl)amino)ethyl)-2-methylbenzonitrile |
| 20 | 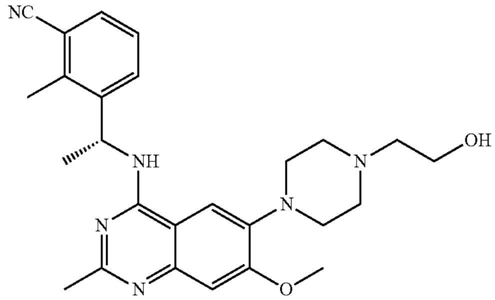 [SMILES: COc1cc2nc(C)nc(N[C@H](C)c3cccc(C#N)c3C)c2cc1N1CCN(CCO)CC1] | (R)-3-(1-((6-(4-(2-hydroxyethyl)piperazin-1-yl)-7-methoxy-2-methylquinazolin-4-yl) amino)ethyl)-2-methylbenzonitrile |
| 21 | 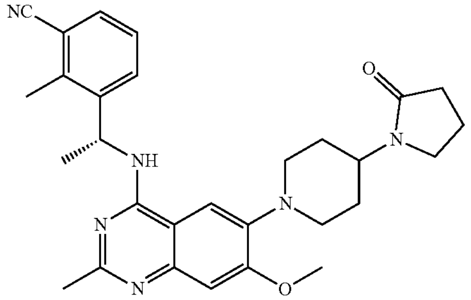 [SMILES: COc1cc2nc(C)nc(N[C@H](C)c3cccc(C#N)c3C)c2cc1N1CCC(N2CCCC2=O)CC1] | (R)-3-(1-((7-methoxy-2-methyl-6-(4-(2-oxopyrrolidin-1-yl)piperidin-1-yl)quinazolin-4-yl)amino)ethyl)-2-methylbenzonitrile |

-continued

| Compound number | Structure | Name |
|---|---|---|
| 22 | 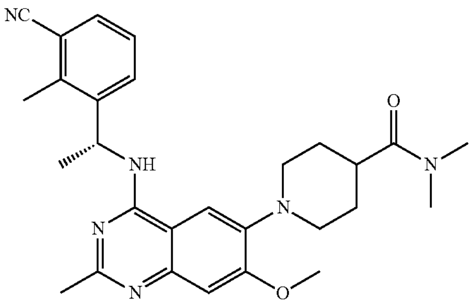 | (R)-1-(4-((1-(3-cyano-2-methylphenyl) ethyl)amino)-7-methoxy-2-methylquinazolin-6-yl)-N, N-dimethylpiperidine-4-carboxamide |
| 23 | 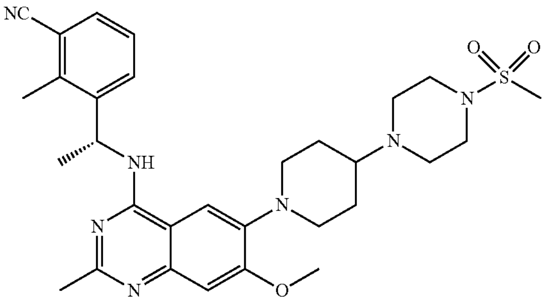 | (R)-3-(1-((7-methoxy-2-methyl-6-(4-(4-(methylsulfonyl)piperazin-1-yl)piperidin-1-yl) quinazolin-4-yl)amino)ethyl)-2-methylbenzonitrile |
| 24 | 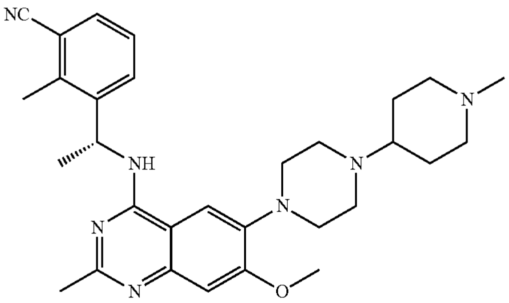 | (R)-3-(1-((7-methoxy-2-methyl-6-(4-(1-methylpiperidin-4-yl)piperazin-1-yl)quinazolin-4-yl)amino)ethyl)-2-methylbenzonitrile |
| 25 | 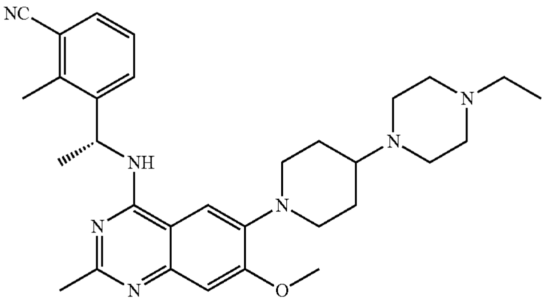 [SMILES: CCN1CCN(C2CCN(c3cc4c(N[C@H](C)c5cccc(C#N)c5C)nc(C)nc4cc3OC)CC2)CC1] | (R)-3-(1-((6-(4-(4-ethylpiperazin-1-yl)piperidin-1-yl)-7-methoxy-2-methylquinazolin-4-yl)amino)ethyl)-2-methylbenzonitrile |
| 26 | 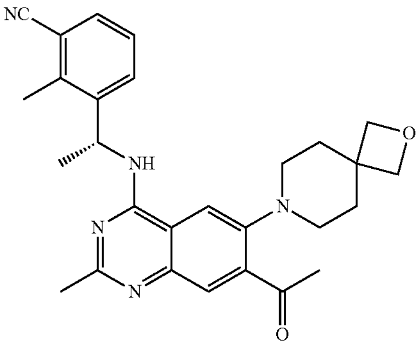 [SMILES: CC(=O)c1cc2nc(C)nc(N[C@H](C)c3cccc(C#N)c3C)c2cc1N1CCC2(CC1)COC2] | (R)-3-(1-((7-acetyl-2-methyl-6-(2-oxa-7-azaspiro[3.5]nonan-7-yl)quinazolin-4-yl) amino)ethyl)-2-methylbenzonitrile |

-continued

| Compound number | Structure | Name |
|---|---|---|
| 27 | 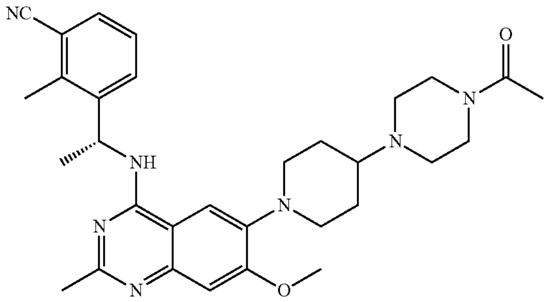 [SMILES: COc1cc2nc(C)nc(N[C@H](C)c3cccc(C#N)c3C)c2cc1N1CCC(N2CCN(C(C)=O)CC2)CC1] | (R)-3-(1-((6-(4-(4-acetylpiperazin-1-yl)piperidin-1-yl)-7-methoxy-2-methylquinazolin-4-yl)amino)ethyl)-2-methylbenzonitrile |
| 28 | 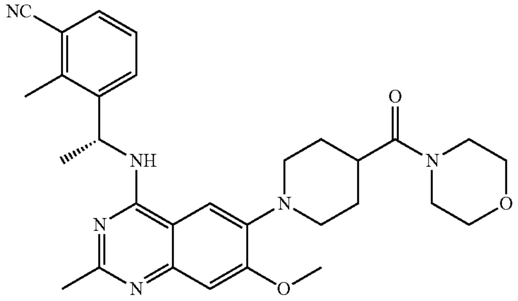 [SMILES: COc1cc2nc(C)nc(N[C@H](C)c3cccc(C#N)c3C)c2cc1N1CCC(C(=O)N2CCOCC2)CC1] | (R)-3-(1-((7-methoxy-2-methyl-6-(4-(morpholine-4-carbonyl)piperidin-1-yl)quinazolin-4-yl)amino)ethyl)-2-methylbenzonitrile |
| 29 | 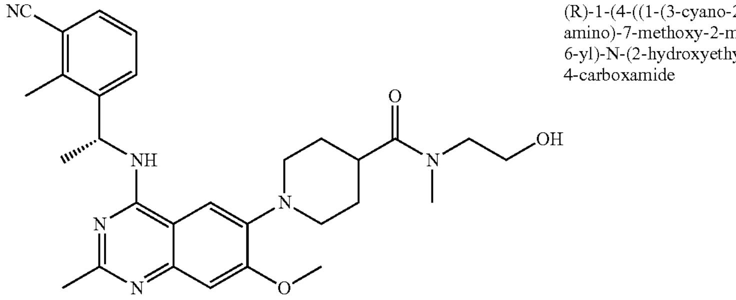 | (R)-1-(4-((1-(3-cyano-2-methylphenyl)ethyl)amino)-7-methoxy-2-methylquinazolin-6-yl)-N-(2-hydroxyethyl)-N-methylpiperidine-4-carboxamide |
| 30 | 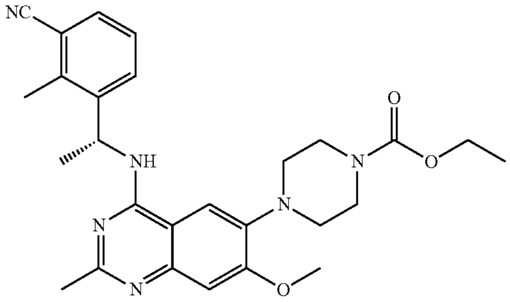 [SMILES: CCOC(=O)N1CCN(c2cc3c(N[C@H](C)c4cccc(C#N)c4C)nc(C)nc3cc2OC)CC1] | ethyl (R)-4-(4-((1-(3-cyano-2-methylphenyl)ethyl)amino)-7-methoxy-2-methylquinazolin-6-yl)piperazine-1-carboxylate |
| 31 | 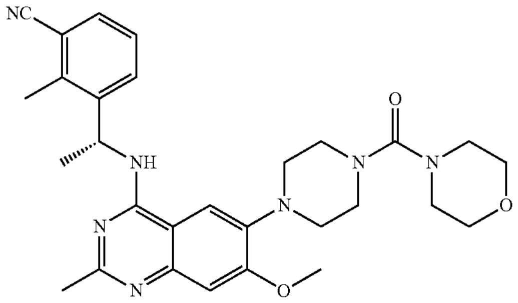 [SMILES: COc1cc2nc(C)nc(N[C@H](C)c3cccc(C#N)c3C)c2cc1N1CCN(C(=O)N2CCOCC2)CC1] | (R)-3-(1-((7-methoxy-2-methyl-6-(4-(morpholine-4-carbonyl)piperazin-1-yl)quinazolin-4-yl)amino)ethyl)-2-methylbenzonitrile |

-continued

| Compound number | Structure | Name |
| --- | --- | --- |
| 32 | 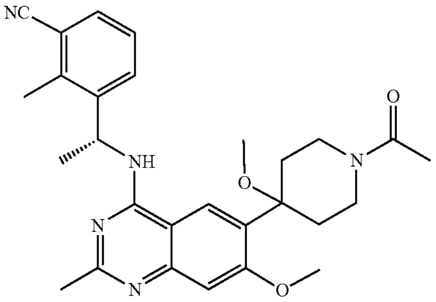 [SMILES: COc1cc2nc(C)nc(N[C@H](C)c3cccc(C#N)c3C)c2cc1C1(OC)CCN(C(C)=O)CC1] | (R)-3-(1-((6-(1-acetyl-4-methoxypiperidin-4-yl)-7-methoxy-2-methylquinazolin-4-yl)amino)ethyl)-2-methylbenzonitrile |
| 33 | 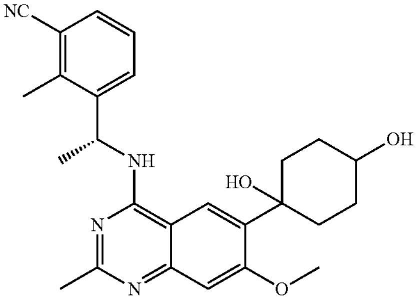 [SMILES: COc1cc2nc(C)nc(N[C@H](C)c3cccc(C#N)c3C)c2cc1C1(O)CCC(O)CC1] | (R)-3-(1-((6-(1,4-dihydroxycyclohexyl)-7-methoxy-2-methylquinazolin-4-yl)amino)ethyl)-2-methylbenzonitrile |
| 34 | 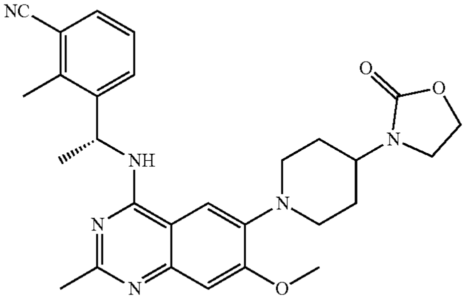 [SMILES: COc1cc2nc(C)nc(N[C@H](C)c3cccc(C#N)c3C)c2cc1N1CCC(N2CCOC2=O)CC1] | (R)-3-(1-((7-methoxy-2-methyl-6-(4-(2-oxooxazolidin-3-yl)piperidin-1-yl)quinazolin-4-yl)amino)ethyl)-2-methylbenzonitrile |
| 35 | 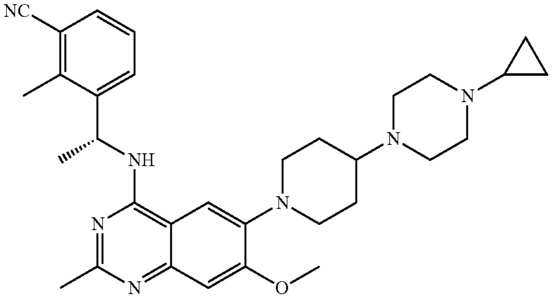 [SMILES: COc1cc2nc(C)nc(N[C@H](C)c3cccc(C#N)c3C)c2cc1N1CCC(N2CCN(C3CC3)CC2)CC1] | (R)-3-(1-((6-(4-(4-cyclopropylpiperazin-1-yl)piperidin-1-yl)-7-methoxy-2-methylquinazolin-4-yl)amino)ethyl)-2-methylbenzonitrile |
| 36 | 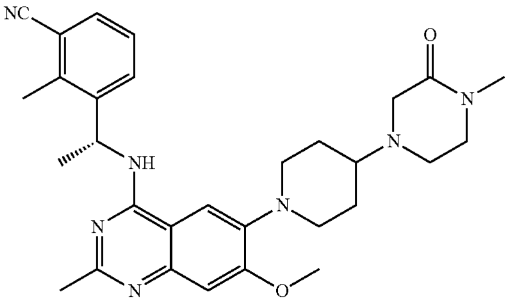 | (R)-3-(1-((7-methoxy-2-methyl-6-(4-(4-methyl-3-oxopiperazin-1-yl)piperidin-1-yl)quinazolin-4-yl)amino)ethyl)-2-methylbenzonitrile |

-continued

| Compound number | Structure | Name |
|---|---|---|
| 37 | 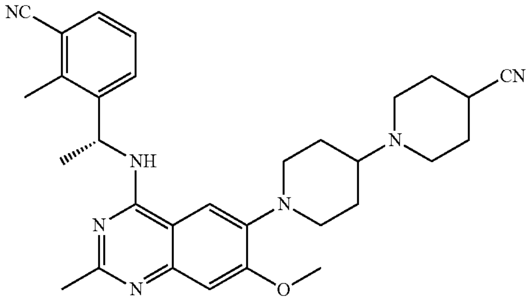 [SMILES: COc1cc2nc(C)nc(N[C@H](C)c3cccc(C#N)c3C)c2cc1N1CCC(N2CCC(C#N)CC2)CC1] | (R)-1'-(4-((1-(3-cyano-2-methylphenyl) ethyl)amino)-7-methoxy-2-methylquinazolin-6-yl)-[1,4'-bipiperidine]-4-carbonitrile |
| 38 | 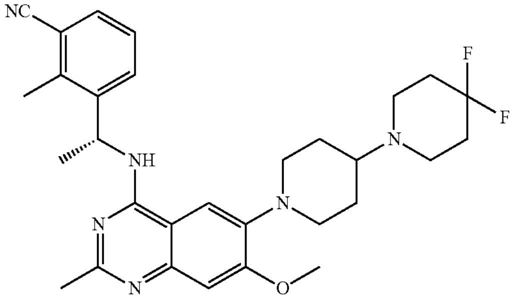 [SMILES: COc1cc2nc(C)nc(N[C@H](C)c3cccc(C#N)c3C)c2cc1N1CCC(N2CCC(F)(F)CC2)CC1] | (R)-3-(1-((6-(4,4-difluoro-[1,4'-bipiperidin]-1'-yl)-7-methoxy-2-methylquinazolin-4-yl) amino)ethyl)-2-methylbenzonitrile |
| 39 | 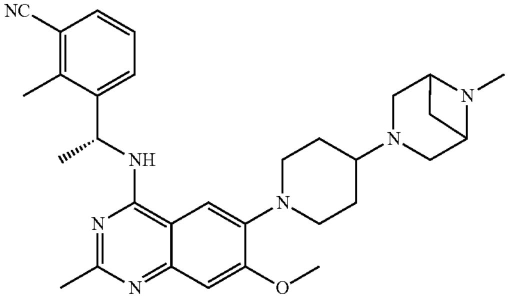 | 3-((1R)-1-((7-methoxy-2-methyl-6-(4-(6-methyl-3,6-diazabicyclo[3.1.1]heptan-3-yl) piperidin-1-yl)quinazolin-4-yl)amino)ethyl)-2-methylbenzonitrile |
| 40 | 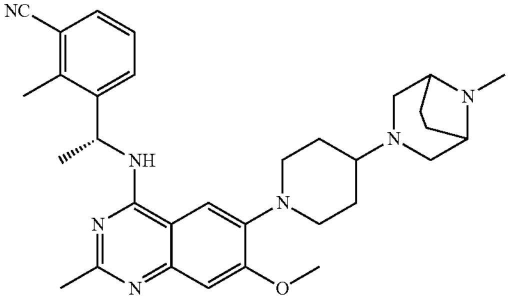 | 3-((1R)-1-((7-methoxy-2-methyl-6-(4-(8-methyl-3,8-diazabicyclo[3.2.1]octan-3-yl) piperidin-1-yl)quinazolin-4-yl)amino)ethyl)-2-methylbenzonitrile |
| 41 | 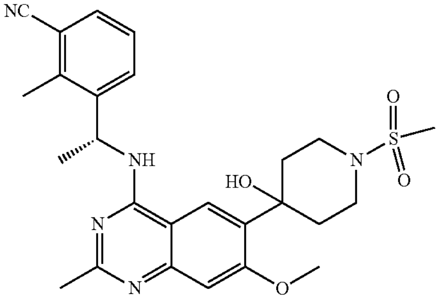 | (R)-3-(1-((6-(4-hydroxy-1-(methylsulfonyl) piperidin-4-yl)-7-methoxy-2-methylquinazolin-4-yl)amino)ethyl)-2-methylbenzonitrile |

-continued

| Compound number | Structure | Name |
|---|---|---|
| 42 | 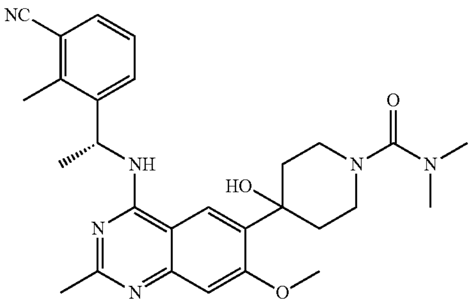 | (R)-4-(4-((1-(3-cyano-2-methylphenyl) ethyl)amino)-7-methoxy-2-methylquinazolin-6-yl)-4-hydroxy-N,N-dimethylpiperidine-1-carboxamide |
| 43 | 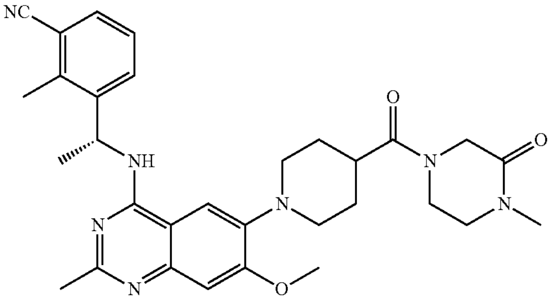 | (R)-3-(1-((7-methoxy-2-methyl-6-(4-(4-methyl-3-oxopiperazine-1-carbonyl)piperidin-1-yl)quinazolin-4-yl)amino)ethyl)-2-methyl benzonitrile |
| 44 | 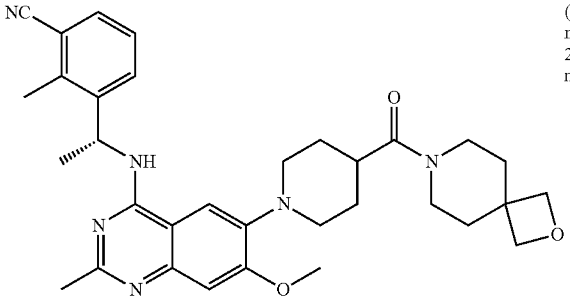 | (R)-3-(1-((6-(4-(2-oxa-7-azaspiro[3.5] nonane-7-carbonyl)piperidin-1-yl)-7-methoxy-2-methylquinazolin-4-yl)amino)ethyl)-2-methylbenzonitrile |
| 45 | 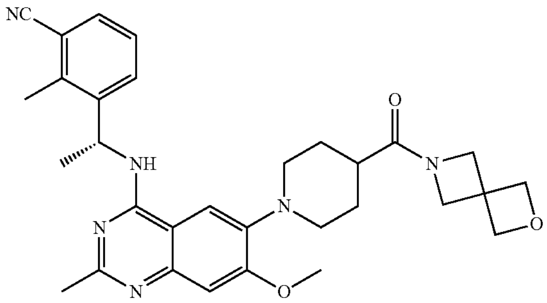 | (R)-3-(1-((6-(4-(2-oxa-6-azaspiro[3.3] heptane-6-carbonyl)piperidin-1-yl)-7-methoxy-2-methylquinazolin-4-yl)amino)ethyl)-2-methylbenzonitrile |

or a stereoisomer, a tautomer, or a pharmaceutically acceptable salt thereof.

NOTE: if there is a difference between a drawn structure and the name given to that structure, greater weight will be given to the drawn structure.

One or more embodiments of the present application provide a compound represented by general formula (I') or a stereoisomer, a tautomer, or a pharmaceutically acceptable salt thereof:

(I')

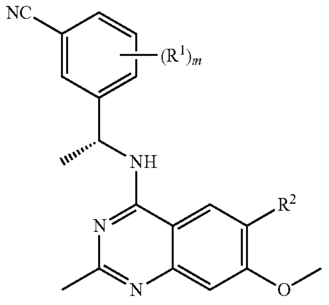

wherein:

$R^1$ are the same or different, and are each independently halogen, hydroxyl, amino, $C_1$-$C_6$ alkyl or $C_1$-$C_6$ alkoxy; wherein, the alkyl or alkoxy is optionally further substituted by one or more substituents selected from halogen, hydroxyl, cyano, amino, $C_1$-$C_6$ alkyl and $C_1$-$C_6$ alkoxy; $R^1$ is preferably $C_1$-$C_6$ alkyl; more preferably methyl;

$R^2$ is 3-6 membered monocyclic heterocyclyl, 6-11 membered spiroheterocyclyl, 6-11 membered bridged heterocyclyl, 6-11 membered fused heterocyclyl or 6-11 membered fused ring; wherein, the monocyclic heterocyclyl, spiroheterocyclyl, bridged heterocyclyl, fused heterocyclyl or fused ring is optionally further substituted by one or more $R^A$s;

$R^A$ is each independently halogen, cyano, $C_1$-$C_6$ alkyl, $C_1$-$C_6$ alkoxy, $C_3$-$C_6$ cycloalkyl, 3-6 membered heterocyclyl or —C(O)$R^3$, wherein, the alkyl, alkoxy, cycloalkyl or heterocyclyl is optionally further substituted by one or more substituents selected from halogen, nitro, cyano, hydroxyl, amino, $C_1$-$C_6$ alkyl and $C_1$-$C_6$ alkoxy;

or, two $R^A$s together with the same carbon atom to which they are bound form —C(═O)—;

$R^3$ is $C_1$-$C_6$ alkyl, $C_3$-$C_6$ cycloalkyl or 3-6 membered heterocyclyl, wherein, the alkyl, cycloalkyl or heterocyclyl is optionally further substituted by one or more substituents selected from hydroxyl, halogen, nitro, amino, cyano, $C_1$-$C_6$ alkyl, $C_1$-$C_6$ alkoxy, $C_1$-$C_6$ haloalkyl and $C_1$-$C_6$ haloalkoxy;

m is 0, 1, 2, 3 or 4;

One or more embodiments of the present application provide a compound represented by general formula (II') or a stereoisomer, a tautomer, or a pharmaceutically acceptable salt thereof:

(II')

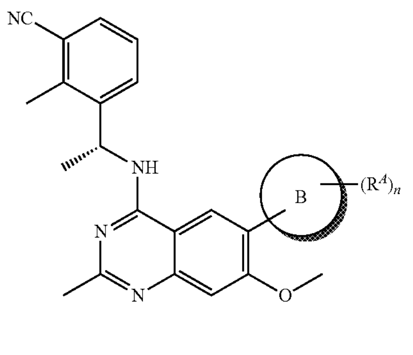

wherein:

ring B is 3-6 membered monocyclic heterocyclyl, 6-11 membered spiroheterocyclyl, 6-11 membered bridged heterocyclyl, 6-11 membered fused heterocyclyl or 6-11 membered fused ring;

$R^A$ is each independently $C_1$-$C_6$ alkyl, $C_1$-$C_6$ alkoxy, $C_1$-$C_6$ haloalkyl, 3-6 membered heterocyclyl or —C(O)$R^3$, $R^3$ is $C_1$-$C_6$ alkyl, $C_3$-$C_6$ cycloalkyl or 3-6 membered heterocyclyl; wherein, the alkyl, cycloalkyl or heterocyclyl is optionally further substituted by one or more substituents selected from halogen, cyano and $C_1$-$C_6$ alkyl;

n is 0, 1, 2 or 3.

One or more embodiments of the present application provide a compound represented by general formula (I") or a stereoisomer, a tautomer, or a pharmaceutically acceptable salt thereof:

(I")

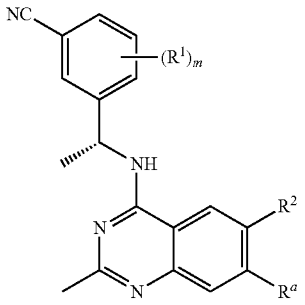

wherein:

$R^a$ is cyano or $C_1$-$C_6$ alkoxy;

$R^1$ are the same or different, and are each independently halogen, hydroxyl, amino, $C_1$-$C_6$ alkyl or $C_1$-$C_6$ alkoxy; wherein, the alkyl or alkoxy is optionally further substituted by one or more substituents selected from halogen, hydroxyl, cyano, amino, $C_1$-$C_6$ alkyl and $C_1$-$C_6$ alkoxy; $R^1$ is preferably $C_1$-$C_6$ alkyl; more preferably methyl;

$R^2$ is 3-6 membered monocyclic heterocyclyl, 6-11 membered spiroheterocyclyl, 6-11 membered bridged heterocyclyl, 6-11 membered fused heterocyclyl or 6-11 membered fused ring; wherein, the monocyclic heterocyclyl, spiroheterocyclyl, bridged heterocyclyl, fused heterocyclyl or fused ring is optionally further substituted by one or more $R^A$s;

$R^A$ is each independently halogen, cyano, $C_1$-$C_6$ alkyl, $C_1$-$C_6$ alkoxy, $C_3$-$C_6$ cycloalkyl, 3-6 membered heterocyclyl or —C(O)$R^3$, wherein, the alkyl, alkoxy, cycloalkyl or heterocyclyl is optionally further substituted by one or more substituents selected from halogen, nitro, cyano, hydroxyl, amino, $C_1$-$C_6$ alkyl and $C_1$-$C_6$ alkoxy;

or, two $R^A$s together with the same carbon atom to which they are bound form —C(═O)—;

$R^3$ is $C_1$-$C_6$ alkyl, $C_3$-$C_6$ cycloalkyl or 3-6 membered heterocyclyl, wherein, the alkyl, cycloalkyl or heterocyclyl is optionally further substituted by one or more substituents selected from hydroxyl, halogen, nitro, amino, cyano, $C_1$-$C_6$ alkyl, $C_1$-$C_6$ alkoxy, $C_1$-$C_6$ haloalkyl and $C_1$-$C_6$ haloalkoxy;

m is 0, 1, 2, 3 or 4.

One or more embodiments of the present application provide a compound represented by general formula (II") or a stereoisomer, a tautomer, or a pharmaceutically acceptable salt thereof:

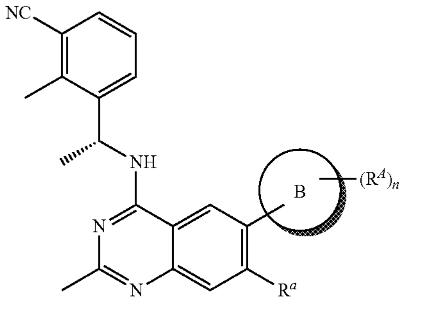

(II″)

wherein:

$R^a$ is cyano or methoxy;

ring B is 3-6 membered monocyclic heterocyclyl, 6-11 membered spiroheterocyclyl, 6-11 membered bridged heterocyclyl, 6-11 membered fused heterocyclyl or 6-11 membered fused ring;

$R^A$ is each independently $C_1$-$C_6$ alkyl, $C_1$-$C_6$ alkoxy, $C_1$-$C_6$ haloalkyl, 3-6 membered heterocyclyl or —C(O)$R^3$;

$R^3$ is $C_1$-$C_6$ alkyl, $C_3$-$C_6$ cycloalkyl or 3-6 membered heterocyclyl; wherein, the alkyl, cycloalkyl and heterocyclyl is optionally further substituted by one or more substituents selected from halogen, cyano and $C_1$-$C_6$ alkyl;

n is 0, 1, 2 or 3.

One or more embodiments of the present application provide a compound represented by general formula (I‴) or a stereoisomer, a tautomer, or a pharmaceutically acceptable salt thereof:

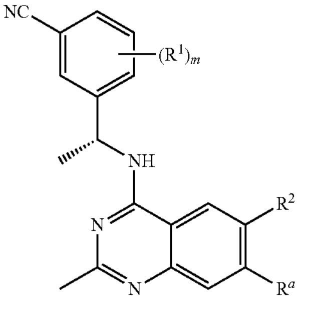

(I‴)

wherein:

$R^a$ is cyano, —C(O)$R^3$ or $C_1$-$C_6$ alkoxy;

$R^1$ are the same or different, and are each independently halogen, hydroxyl, amino, $C_1$-$C_6$ alkyl or $C_1$-$C_6$ alkoxy; wherein, the alkyl or alkoxy is optionally further substituted by one or more substituents selected from halogen, hydroxyl, cyano, amino, $C_1$-$C_6$ alkyl and $C_1$-$C_6$ alkoxy; $R^1$ is preferably $C_1$-$C_6$ alkyl; more preferably methyl;

$R^2$ is $C_3$-$C_6$ cycloalkyl, 3-6 membered monocyclic heterocyclyl, 6-11 membered spiroheterocyclyl, 6-11 membered bridged heterocyclyl, 6-11 membered fused heterocyclyl or 6-11 membered fused ring; wherein, the cycloalkyl, monocyclic heterocyclyl, spiroheterocyclyl, bridged heterocyclyl, fused heterocyclyl or fused ring is optionally further substituted by one or more RAS.

$R^A$ is each independently halogen, cyano, hydroxyl, amino, oxo, $C_1$-$C_6$ alkyl, $C_1$-$C_6$ alkoxy, $C_3$-$C_6$ cycloalkyl, 3-8 membered heterocyclyl, —C(O)$R^3$ or —$SO_2R^4$, wherein, the alkyl, alkoxy or cycloalkyl is optionally further substituted by one or more substituents selected from halogen, nitro, cyano, hydroxyl, amino, $C_1$-$C_6$ alkyl, $C_3$-$C_6$ cycloalkyl, $C_1$-$C_6$ alkoxy and —$SO_2R^4$; the heterocyclyl is optionally further substituted by one or more substituents selected from halogen, nitro, cyano, hydroxyl, amino, oxo, $C_1$-$C_6$ alkyl, $C_3$-$C_6$ cycloalkyl, $C_1$-$C_6$ alkoxy and —$SO_2R^4$;

$R^3$ is each independently $C_1$-$C_6$ alkyl, $C_3$-$C_6$ cycloalkyl, —$NR^5R^6$ or 3-6 membered heterocyclyl, wherein, the alkyl or cycloalkyl is optionally further substituted by one or more substituents selected from hydroxyl, halogen, nitro, amino, cyano, $C_1$-$C_6$ alkyl, $C_1$-$C_6$ alkoxy, $C_1$-$C_6$ haloalkyl and $C_1$-$C_6$ haloalkoxy; the heterocyclyl is optionally further substituted by one or more substituents selected from hydroxyl, halogen, nitro, amino, cyano, oxo, $C_1$-$C_6$ alkyl, $C_1$-$C_6$ alkoxy, $C_1$-$C_6$ haloalkyl and $C_1$-$C_6$ haloalkoxy;

$R^4$ is each independently amino, $C_1$-$C_6$ alkyl or $C_3$-$C_6$ cycloalkyl;

$R^5$ and $R^6$ are each independently a hydrogen atom or $C_1$-$C_6$ alkyl, or, $R^5$ and $R^6$ together with the N atom bound therewith form a 4-6 membered heterocyclic ring, the formed heterocyclic ring is optionally further substituted with a substituent selected from halogen, cyano, hydroxyl, amino, oxo, $C_1$-$C_6$ alkyl, $C_1$-$C_6$ alkoxy and $C_3$-$C_6$ cycloalkyl;

m is 0, 1, 2, 3 or 4.

One or more embodiments of the present application provide a compound represented by general formula (II‴) or a stereoisomer, a tautomer, or a pharmaceutically acceptable salt thereof:

(II‴)

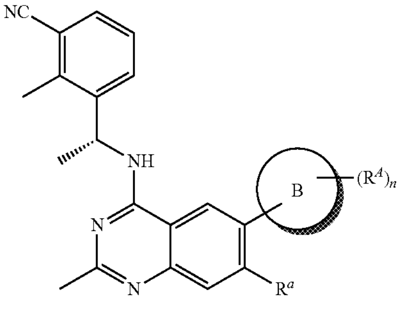

wherein:

$R^a$ is cyano, acetyl or methoxy;

ring B is $C_3$-$C_6$ cycloalkyl, 3-6 membered monocyclic heterocyclyl, 6-11 membered spiroheterocyclyl, 6-11 membered bridged heterocyclyl, 6-11 membered fused heterocyclyl or 6-11 membered fused ring;

$R^A$ is each independently halogen, cyano, hydroxyl, amino, oxo, $C_1$-$C_6$ alkyl, $C_1$-$C_6$ alkoxy, $C_3$-$C_6$ cycloalkyl, 3-8 membered heterocyclyl, —C(O)$R^3$ or —$SO_2R^4$, wherein, the alkyl, alkoxy or cycloalkyl is optionally further substituted by one or more substituents selected from halogen, nitro, cyano, hydroxyl, amino, $C_1$-$C_6$ alkyl, $C_3$-$C_6$ cycloalkyl, $C_1$-$C_6$ alkoxy and —$SO_2R^4$; the heterocyclyl is optionally further substituted by one or more substituents selected from halogen, nitro, cyano, hydroxyl, amino, oxo, $C_1$-$C_6$ alkyl, $C_3$-$C_6$ cycloalkyl, $C_1$-$C_6$ alkoxy and —$SO_2R^4$;

$R^3$ is $C_1$-$C_6$ alkyl, $C_3$-$C_6$ cycloalkyl, —$NR^5R^6$ or 3-6 membered heterocyclyl; wherein, the alkyl or cycloalkyl is optionally further substituted by one or more substituents selected from halogen, cyano and $C_1$-$C_6$ alkyl; the heterocyclyl is optionally further substituted by one or more substituents selected from halogen, cyano, oxo and $C_1$-$C_6$ alkyl;

$R^4$ is each independently amino, $C_1$-$C_6$ alkyl or $C_3$-$C_6$ cycloalkyl;

$R^5$ and $R^6$ are each independently a hydrogen atom or $C_1$-$C_6$ alkyl;

or, $R^5$ and $R^6$ together with the N atom bound therewith form a 4-6 membered heterocyclic ring, the formed heterocyclic ring is optionally further substituted with a substituent selected from halogen, cyano, hydroxyl, amino, oxo, $C_1$-$C_6$ alkyl, $C_1$-$C_6$ alkoxy and $C_3$-$C_6$ cycloalkyl;

n is 0, 1, 2 or 3.

One or more embodiments of the present application provide a compound represented by general formula (I'''') or a stereoisomer, a tautomer, or a pharmaceutically acceptable salt thereof:

(I'''')

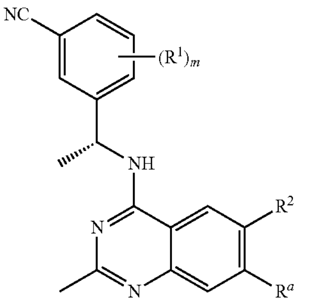

wherein:

$R^a$ is cyano, —$C(O)R^3$ or $C_1$-$C_6$ alkoxy;

$R^1$ are the same or different, and are each independently halogen, hydroxyl, amino, $C_1$-$C_6$ alkyl or $C_1$-$C_6$ alkoxy; wherein, the alkyl or alkoxy is optionally further substituted by one or more substituents selected from halogen, hydroxyl, cyano, amino, $C_1$-$C_6$ alkyl and $C_1$-$C_6$ alkoxy; $R^1$ is preferably $C_1$-$C_6$ alkyl; more preferably methyl;

$R^2$ is $C_3$-$C_6$ cycloalkyl, 3-6 membered monocyclic heterocyclyl, 6-11 membered spiroheterocyclyl, 6-11 membered bridged heterocyclyl, 6-11 membered fused heterocyclyl or 6-11 membered fused ring; wherein, the cycloalkyl, monocyclic heterocyclyl, spiroheterocyclyl, bridged heterocyclyl, fused heterocyclyl or fused ring is optionally further substituted by one or more $R^A$s;

$R^A$ is each independently halogen, cyano, hydroxyl, amino, oxo, $C_1$-$C_6$ alkyl, $C_1$-$C_6$ alkoxy, $C_3$-$C_6$ cycloalkyl, 3-8 membered heterocyclyl, —$C(O)R^3$ or —$SO_2R^4$, wherein, the alkyl, alkoxy or cycloalkyl is optionally further substituted by one or more substituents selected from halogen, nitro, cyano, hydroxyl, amino, $C_1$-$C_6$ alkyl, $C_3$-$C_6$ cycloalkyl, $C_1$-$C_6$ alkoxy and —$SO_2R^4$; the heterocyclyl is optionally further substituted by one or more substituents selected from halogen, nitro, cyano, hydroxyl, amino, oxo, $C_1$-$C_6$ alkyl, $C_3$-$C_6$ cycloalkyl, $C_1$-$C_6$ alkoxy and —$SO_2R^4$;

$R^3$ is each independently $C_1$-$C_6$ alkyl, $C_1$-$C_3$ alkoxy, $C_3$-$C_6$ cycloalkyl, —$NR^5R^6$ or 3-6 membered heterocyclyl, wherein, the alkyl or cycloalkyl is optionally further substituted by one or more substituents selected from hydroxyl, halogen, nitro, amino, cyano, $C_1$-$C_6$ alkyl, $C_1$-$C_6$ alkoxy, $C_1$-$C_6$ haloalkyl and $C_1$-$C_6$ haloalkoxy; the heterocyclyl is optionally further substituted by one or more substituents selected from hydroxyl, halogen, nitro, amino, cyano, oxo, $C_1$-$C_6$ alkyl, $C_1$-$C_6$ alkoxy, $C_1$-$C_6$ haloalkyl and $C_1$-$C_6$ haloalkoxy;

$R^4$ is each independently amino, $C_1$-$C_6$ alkyl or $C_3$-$C_6$ cycloalkyl;

$R^5$ and $R^6$ are each independently a hydrogen atom or $C_1$-$C_6$ alkyl, wherein, the alkyl is optionally further substituted by one or more substituents selected from hydroxyl, halogen, amino, cyano and $C_1$-$C_6$ alkoxy;

or, $R^5$ and $R^6$ together with the N atom bound therewith form a 4-10 membered heterocyclic ring, the formed heterocyclic ring is optionally further substituted with a substituent selected from halogen, cyano, hydroxyl, amino, oxo, $C_1$-$C_6$ alkyl, $C_1$-$C_6$ alkoxy, —$C(O)R^7$ and $C_3$-$C_6$ cycloalkyl;

$R^7$ is $C_1$-$C_3$ alkyl or $C_3$-$C_6$ cycloalkyl, the alkyl or cycloalkyl is optionally further substituted by one or more substituents selected from hydroxyl, halogen, amino, cyano and $C_1$-$C_6$ alkoxy;

m is 0, 1, 2, 3 or 4.

One or more embodiments of the present application provide a compound represented by general formula (II'''') or a stereoisomer, a tautomer, or a pharmaceutically acceptable salt thereof:

(II'''')

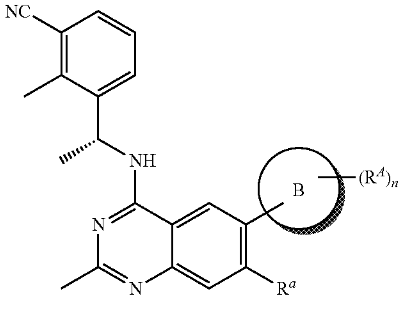

wherein:

$R^a$ is cyano, acetyl or methoxy;

ring B is $C_3$-$C_6$ cycloalkyl, 3-6 membered monocyclic heterocyclyl, 6-11 membered spiroheterocyclyl, 6-11 membered bridged heterocyclyl, 6-11 membered fused heterocyclyl or 6-11 membered fused ring;

$R^A$ is each independently halogen, cyano, hydroxyl, amino, oxo, $C_1$-$C_6$ alkyl, $C_1$-$C_6$ alkoxy, $C_3$-$C_6$ cycloalkyl, 3-8 membered heterocyclyl, —$C(O)R^3$ or —$SO_2R^4$, wherein, the alkyl, alkoxy or cycloalkyl is optionally further substituted by one or more substituents selected from halogen, nitro, cyano, hydroxyl, amino, $C_1$-$C_6$ alkyl, $C_3$-$C_6$ cycloalkyl, $C_1$-$C_6$ alkoxy and —$SO_2R^4$; the heterocyclyl is optionally further substituted by one or more substituents selected from halogen, nitro, cyano, hydroxyl, amino, oxo, $C_1$-$C_6$ alkyl, $C_3$-$C_6$ cycloalkyl, $C_1$-$C_6$ alkoxy and —$SO_2R^4$;

$R^3$ is $C_1$-$C_6$ alkyl, $C_1$-$C_3$ alkoxy, $C_3$-$C_6$ cycloalkyl, —$NR^5R^6$ or 3-6 membered heterocyclyl; wherein, the alkyl or cycloalkyl is optionally further substituted by one or more substituents selected from halogen, cyano and $C_1$-$C_6$ alkyl; the heterocyclyl is optionally further substituted by one or more substituents selected from halogen, cyano, oxo and $C_1$-$C_6$ alkyl;

$R^4$ is each independently amino, $C_1$-$C_6$ alkyl or $C_3$-$C_6$ cycloalkyl;

$R^5$ and $R^6$ are each independently a hydrogen atom or $C_1$-$C_6$ alkyl, wherein, the alkyl is optionally further substituted by one or more substituents selected from hydroxyl, halogen, amino, cyano and $C_1$-$C_6$ alkoxy;

or, $R^5$ and $R^6$ together with the N atom bound therewith form a 4-10 membered heterocyclic ring, the formed heterocyclic ring is optionally further substituted with a substituent selected from halogen, cyano, hydroxyl, amino, oxo, $C_1$-$C_6$ alkyl, $C_1$-$C_6$ alkoxy, —C(O)$R^7$ and $C_3$-$C_6$ cycloalkyl;

$R^7$ is $C_1$-$C_3$ alkyl or $C_3$-$C_6$ cycloalkyl, the alkyl or cycloalkyl is optionally further substituted by one or more substituents selected from hydroxyl, halogen, amino, cyano and $C_1$-$C_6$ alkoxy;

n is 0, 1, 2 or 3.

Furthermore, the present invention provides a pharmaceutical composition, the pharmaceutical composition comprises an effective amount of the compound represented by general formula (I), (II), (I'), (II'), (I"), (II"), (I'"), (II'"), (I"") or (II""), or a stereoisomer, a tautomer, or a pharmaceutically acceptable salt thereof, and a pharmaceutically acceptable carrier, an excipient or a combination thereof.

The present invention provides use of the compound represented by general formula (I), (II), (I'), (II'), (I"), (II"), (I'"), (II'"), (I"") or (II""), or a stereoisomer, a tautomer, or a pharmaceutically acceptable salt thereof, or a pharmaceutical composition thereof in the preparation of an SOS1 inhibitor.

The present invention also provides use of the compound represented by general formula (I), (II), (I'), (II'), (I"), (II"), (I'"), (II'"), (I"") or (II""), or a stereoisomer, a tautomer, or a pharmaceutically acceptable salt thereof, or a pharmaceutical composition thereof in the preparation of a medicament for treating a disease mediated by SOS1, wherein the disease mediated by SOS1 is preferably cancer related to signaling pathway dependence of RAS family proteins, cancer caused by SOS1 mutations, or hereditary disease caused by SOS1 mutations; wherein the disease mediated by SOS1 is preferably lung cancer, pancreatic cancer, colon cancer, bladder cancer, prostate cancer, bile duct cancer, gastric cancer, diffuse large B-cell lymphoma, neurofibroma, Noonan syndrome, cardio-facio-cutaneous syndrome, type I hereditary gingival fibromatosis, embryonal rhabdomyosarcoma, Sertoli cell testicular tumor or cutaneous granular cell tumor.

The present invention further provides use of the compound represented by general formula (I), (II), (I'), (II'), (I"), (II"), (I'"), (II'"), (I"") or (II""), or a stereoisomer, or a tautomer, or a pharmaceutically acceptable salt thereof, or a pharmaceutical composition thereof in the preparation of a medicament for treating cancer related to signaling pathway dependence of RAS family proteins, cancer caused by SOS1 mutations, or hereditary disease caused by SOS1 mutations.

The present invention provides use of the compound represented by general formula (I), (II), (I'), (II'), (I"), (II"), (I'"), (II'"), (I"") or (II""), or a stereoisomer, a tautomer, or a pharmaceutically acceptable salt thereof, or a pharmaceutical composition thereof in the preparation of a medicament for treating lung cancer, pancreatic cancer, colon cancer, bladder cancer, prostate cancer, bile duct cancer, gastric cancer, diffuse large B-cell lymphoma, neurofibroma, Noonan syndrome, cardio-facio-cutaneous syndrome, type I hereditary gingival fibromatosis, embryonal rhabdomyosarcoma, Sertoli cell testicular tumor or cutaneous granular cell tumor.

The present invention also provides a composition, which comprises the compound represented by the above general formula (I), (II), (I'), (II'), (I"), (II"), (I'"), (II'"), (I"") or (II""), or a stereoisomer, a tautomer, or a pharmaceutically acceptable salt thereof, or the above pharmaceutical composition and other medicaments the other medicaments are preferably KRAS G12C inhibitors.

The present invention also provides a compound represented by general formula (I), (II), (I'), (II'), (I"), (II"), (I'"), (II'"), (I"") or (II""), or a stereoisomer, a tautomer, or a pharmaceutically acceptable salt thereof, or a pharmaceutical composition thereof for use as a medicament.

The present invention also provides a compound represented by general formula (I), (II), (I'), (II'), (I"), (II"), (I'"), (II'"), (I"") or (II""), or a stereoisomer, a tautomer, or a pharmaceutically acceptable salt thereof, or a pharmaceutical composition thereof for use as an SOS1 inhibitor.

The present invention also provides a compound represented by general formula (I), (II), (I'), (II'), (I"), (II"), (I'"), (II'"), (I"") or (II""), or a stereoisomer, a tautomer, or a pharmaceutically acceptable salt thereof, or a pharmaceutical composition thereof for use in the prevention and/or treatment of a disease mediated by SOS1, wherein the disease mediated by SOS1 is preferably cancer related to signaling pathway dependence of RAS family proteins, cancer caused by SOS1 mutations, or hereditary disease caused by SOS1 mutations; wherein the disease mediated by SOS1 is preferably lung cancer, pancreatic cancer, colon cancer, bladder cancer, prostate cancer, bile duct cancer, gastric cancer, diffuse large B-cell lymphoma, neurofibroma, Noonan syndrome, cardio-facio-cutaneous syndrome, type I hereditary gingival fibromatosis, embryonal rhabdomyosarcoma, Sertoli cell testicular tumor or cutaneous granular cell tumor.

The present invention also provides a compound represented by general formula (I), (II), (I'), (II'), (I"), (II"), (I'"), (II'"), (I"") or (II""), or a stereoisomer, a tautomer, or a pharmaceutically acceptable salt thereof, or a pharmaceutical composition thereof for use in the prevention and/or treatment of cancer related to signaling pathway dependence of RAS family proteins, cancer caused by SOS1 mutations, or hereditary disease caused by SOS1 mutations.

The present invention also provides a compound represented by general formula (I), (II), (I'), (II'), (I"), (II"), (I'"), (II'"), (I"") or (II""), or a stereoisomer, a tautomer, or a pharmaceutically acceptable salt thereof, or a pharmaceutical composition thereof for use in the prevention and/or treatment of lung cancer, pancreatic cancer, colon cancer, bladder cancer, prostate cancer, bile duct cancer, gastric cancer, diffuse large B-cell lymphoma, neurofibroma, Noonan syndrome, cardio-facio-cutaneous syndrome, type I hereditary gingival fibromatosis, embryonal rhabdomyosarcoma, Sertoli cell testicular tumor or cutaneous granular cell tumor.

The invention also provides a method for preventing and/or treating cancer, which comprises administering to a subject in need thereof the compound represented by general formula (I), (II), (I'), (II'), (I"), (II"), (I'"), (II'"), (I"") or (II""), or a stereoisomer, a tautomer, or a pharmaceutically acceptable salt thereof, or a pharmaceutical composition thereof.

The invention also provides a method for inhibiting SOS1 in a subject, which comprises administering to a subject in need thereof the compound represented by general formula (I), (II), (I'), (II'), (I''), (II''), (I'''), (II'''), (I'''') or (II''''), or a stereoisomer, a tautomer, or a pharmaceutically acceptable salt thereof, or a pharmaceutical composition thereof.

DETAILED DESCRIPTION

Unless otherwise stated, some of the terms used in the specification and claims of the present invention are defined as follows:

“Alkyl” when used as a group or part of a group refers to include $C_1$-$C_{20}$ linear chain or branched aliphatic hydrocarbon groups (including, for example, 1, 2, 3, 4, 5, 6, 7, 8, 9, 10, 11, 12, 13, 14, 15, 16, 17, 18, 19, 20 carbon atoms). It is preferably $C_1$-$C_{10}$ alkyl, and more preferably $C_1$-$C_6$ alkyl. Examples of alkyls include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, or the like. The alkyl may be substituted or unsubstituted.

“Alkenyl” refers to an alkyl as defined above consisting of at least two carbon atoms and at least one carbon-carbon double bond, representative examples of which include but are not limited to ethenyl, 1-propenyl, 2-propenyl, 1-butenyl, 2-butenyl or 3-butenyl, or the like. (including, for example, 1, 2, 3, 4, 5, 6, 7, 8, 9, 10, 11, 12, 13, 14, 15, 16, 17, 18, 19, 20 carbon atoms). The alkenyl may be substituted or unsubstituted.

“Alkynyl” refers to an aliphatic hydrocarbon group with one carbon-carbon triple bond, which may be a linear chain or branched chain. Preferably, $C_2$-$C_{10}$ alkynyl, more preferably $C_2$-$C_6$ alkynyl, and most preferably $C_2$-$C_4$ alkynyl (including, for example, 1, 2, 3, 4, 5, 6, 7, 8, 9, 10, 11, 12, 13, 14, 15, 16, 17, 18, 19, 20 carbon atoms). Examples of alkynyl groups include, but are not limited to, ethynyl, 1-propynyl, 2-propynyl, 1-butynyl, 2-butynyl or 3-butynyl, or the like. The alkynyl may be substituted or unsubstituted.

“Cycloalkyl” refers to saturated or partially saturated monocyclic, fused, bridged and spirocyclic carbocycles (including, for example, 3, 4, 5, 6, 7, 8, 9, 10, 11, 12 carbons atom). Preferably $C_3$-$C_{12}$ cycloalkyl, more preferably $C_3$-$C_8$ cycloalkyl, and most preferably $C_3$-$C_6$ cycloalkyl. Examples of monocyclic cycloalkyl include, but are not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl, or the like, and cyclopropyl and cyclohexenyl are preferred. The cycloalkyl may be substituted or unsubstituted.

“Spirocycloalkyl” refers to a 5 to 18 membered (for example, 5, 6, 7, 8, 9, 10, 11, 12, 13, 14, 15, 16, 17, 18 membered) polycyclic group with two or more cyclic structures, and single rings share one carbon atom (called a spiro atom) with each other. The ring contains one or more double bonds, but none of the rings has a completely conjugated π-electron aromatic system. Preferably 6 to 14 membered, and more preferably 7 to 10 membered. According to the number of spiro atoms shared between rings, the spirocycloalkyl is classified into mono-spiro, di-spiro or multi-spiro-cycloalkyls, preferably mono-spiro and di-spiro-cycloalkyls, and preferably 4 membered/5 membered, 4 membered/6 membered, 5 membered/5 membered or 5 membered/6 membered. Non-limiting examples of “spirocycloalkyl” include, but are not limited to, spiro[4.5]decyl, spiro[4.4]nonyl, spiro[3.5]nonyl, spiro[2.4]heptyl.

“Fused cycloalkyl” refers to a 5 to 18 membered (for example, 5, 6, 7, 8, 9, 10, 11, 12, 13, 14, 15, 16, 17, 18 membered) all-carbon polycyclic group with two or more cyclic structures sharing a pair of carbon atoms, and one or more rings may contain one or more double bonds, but none of the rings has a completely conjugated r-electron aromatic system. Preferably 6 to 12 membered, more preferably 7 to 10 membered. According to the number of constituent rings, fused cycloalkys may be classified into bicyclic, tricyclic, tetracyclic or polycyclic fused cycloalkyls, preferably bicyclic or tricyclic, more preferably 5 membered/5 membered or 5 membered/6 membered bicyclic cycloalkyl. Non-limiting examples of “fused cycloalkyl” include, but are not limited to, bicyclo[3.1.0]hexyl, bicyclo[3.2.0]hept-1-enyl, bicyclo[3.2.0]heptyl, decalinyl or tetradecahydrophenanthryl.

“Bridged cycloalkyl” refers to a 5 to 18 membered (for example, 5, 6, 7, 8, 9, 10, 11, 12, 13, 14, 15, 16, 17, 18 membered) all-carbon polycyclic group with two or more cyclic structures sharing two carbon atoms that are not directly bound with each other, one or more rings may contain one or more double bonds, but none of the rings has a completely conjugated r-electron aromatic system. Preferably 6 to 12 membered, more preferably 7 to 10 membered. According to the number of constituent rings, bridged cycloalkyls may be classified into bicyclic, tricyclic, tetracyclic or polycyclic bridged cycloalkyls, preferably bicyclic, tricyclic or tetracyclic, and more preferably bicyclic or tricyclic. Non-limiting examples of “bridged cycloalkyl” include, but are not limited to, (1s,4s)-bicyclo[2.2.1]heptyl, bicyclo[3.2.1]octyl, (1s,5s)-bicyclo[3.3.1]nonyl, bicyclo[2.2.2]octyl, (1 r,5r)-bicyclo[3.3.2]decyl, bicyclo[2.2.1]heptyl or adamantyl.

“Heterocyclyl”, “heterocycle” or “heterocyclic” are used interchangeably herein to refer to a non-aromatic heterocyclic group wherein one or more (e.g. 1, 2, 3 or 4) of the ring-forming atoms are heteroatoms, such as oxygen, nitrogen, sulfur, phosphorus atoms, etc., including monocyclic, polycyclic, fused, bridged and spiro rings. Heterocyclyl preferably has a 5- to 7-membered monocyclic ring or a 7- to 10-membered (for example, 4, 5, 6, 7, 8, 9, 10 membered) bicyclic- or tricyclic ring which may contain 1, 2 or 3 heteroatoms selected from nitrogen, oxygen, $P(O)_n$ or $S(O)_n$ (wherein n is selected from 0, 1 or 2).

Examples of “monocyclic heterocyclyl” include, but are not limited to morpholinyl, oxetan, thiomorpholinyl, tetrahydrofuryl, tetrahydropyranyl, 1,1-dioxo-thiomorpholinyl, piperidinyl, pyrrolidinyl, piperazinyl, hexahydropyrimidinyl,

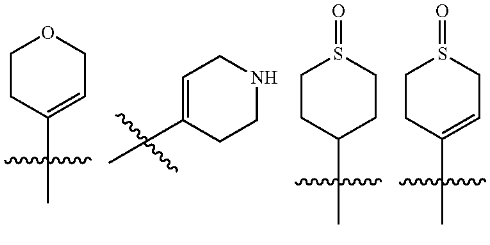

-continued

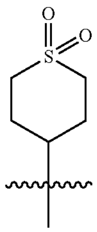 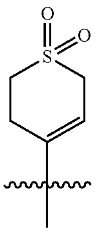 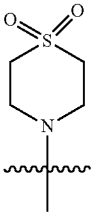 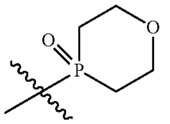 or

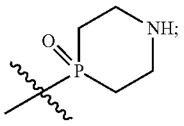

the monocyclic heterocyclyl may be substituted or unsubstituted.

"Spiroheterocyclyl" refers to a 5 to 18 membered (for example, 5, 6, 7, 8, 9, 10, 11, 12, 13, 14, 15, 16, 17, 18 membered) polycyclic group with two or more cyclic structures, and single rings share one atom with each other. The ring contains one or more double bonds, but none of the rings has a completely conjugated π-electron aromatic system, wherein one or more (for example, 1, 2, 3, 4) ring atoms are selected from the heteroatoms of nitrogen, oxygen, $P(O)_n$ or $S(O)_n$ (wherein n is selected from 0, 1 or 2), and the remaining ring atoms are carbon. Spiroheterocyclyl is preferably 6- to 14-membered, more preferably 7- to 10-membered. According to the number of spiro atoms shared between rings, the spirocycloalkyl may be classified into mono-spiroheterocyclyl, bi-spiroheterocyclyl or multi-spiroheterocyclyl, preferably mono-spiroheterocyclyl and bi-spiroheterocyclyl. More preferably, a 4 membered/4 membered, 4 membered/5 membered, 4 membered/6 membered, 5 membered/5 membered or 5 membered/6 membered mono-spiroheterocyclyl. Non-limiting examples of "spiroheterocyclyl" include, but are not limited to: 1,7-dioxaspiro[4.5]decyl, 2-oxa-7-azaspiro[4.4]nonyl, 7-oxaspiro[3.5]nonyl, 5-oxaspiro[2.4]heptyl,

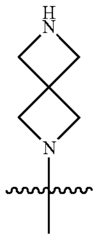 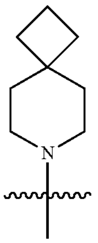 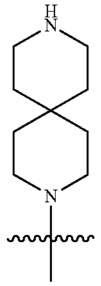 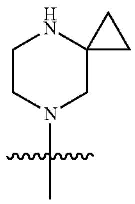

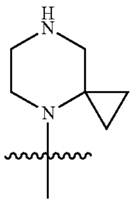 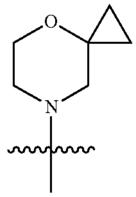 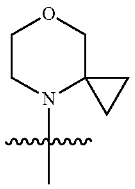

-continued

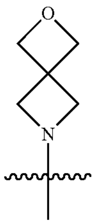 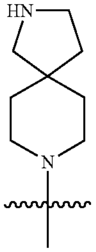 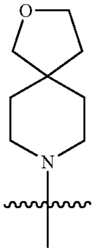 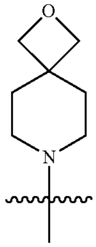

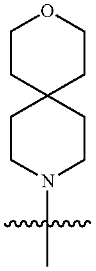 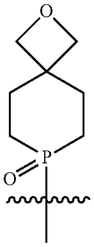 or 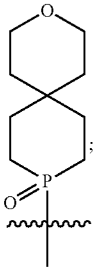 ;

the spiroheterocyclyl may be substituted or unsubstituted.

"Fused heterocyclyl" refers to a polycyclic group with two or more cyclic structures sharing a pair of atoms, and one or more rings may contain one or more double bonds, but none of the rings has a completely conjugated π-electron aromatic system, wherein one or more (for example, 1, 2, 3, 4) ring atoms are selected from heteroatoms of nitrogen, oxygen, $P(O)_n$ or $S(O)_n$ (wherein n is selected from 0, 1 or 2), and the remaining ring atoms are carbon. Preferably 6 to 14 membered, more preferably 7 to 10 membered (for example, 6, 7, 8, 9, 10, 11, 12, 13, 14 membered). According to the number of constituent rings, fused heterocyclyl may be classified into bicyclic, tricyclic, tetracyclic or polycyclic fused heterocyclyls, preferably bicyclic or tricyclic, and more preferably 5 membered/5 membered or 5 membered/6 membered bicyclic fused heterocyclyl. Non-limiting examples of "fused heterocyclyl" include, but are not limited to: octahydropyrro[3,4-c]pyrrolyl, octahydro-1H-isoindolyl, 3-azabicyclo[3.1.0]hexyl, octahydrobenzo[b][1,4]dioxine,

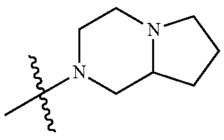 or 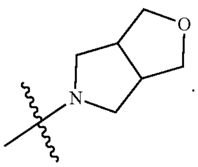 .

"Bridged heterocyclyl" refers to a 5 to 14 membered, or 5 to 18 membered (for example, 5, 6, 7, 8, 9, 10, 11, 12, 13, 14, 15, 16, 17, 18 membered) polycyclic group with two or more cyclic structures sharing two atoms that are not directly bound with each other. One or more rings may contain one or more double bonds, but none of the rings has a completely conjugated π-electron aromatic system, wherein one or more (for example, 1, 2, 3, 4) ring atoms are selected from heteroatoms of nitrogen, oxygen, $P(O)_n$ or $S(O)_n$ (where n is selected from 0, 1 or 2), and the remaining ring atoms are carbon. Bridged heterocyclyl is preferably 6 to 14 membered, and more preferably 7 to 10 membered. According to the number of constituent rings, bridged heterocyclyl may be classified into bicyclic, tricyclic, tetracyclic or polycyclic bridged heterocyclyls, preferably bicyclic, tricyclic or tetracyclic, and more preferably bicyclic or tricyclic. Non-limiting examples of "bridged heterocyclyl" include, but are not limited to: 2-azabicyclo[2.2.1]heptyl, 2-azabicyclo[2.2.2]octyl, 2-azabicyclo[3.3.2]decyl,

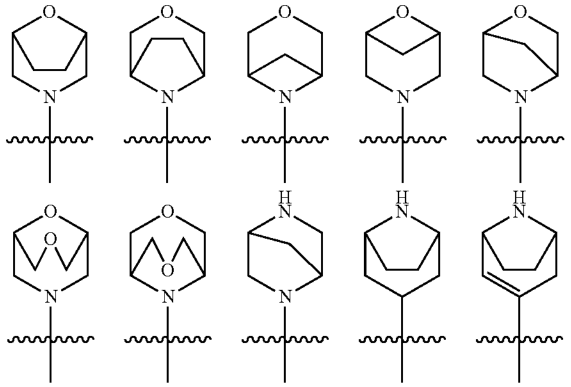

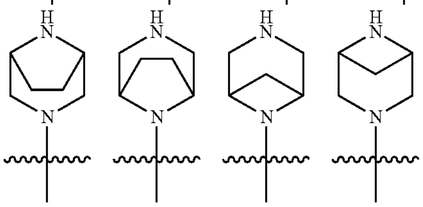

or

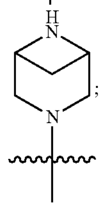

;

the bridged heterocyclyl may be substituted or unsubstituted.

"Aryl" refers to a carbocyclic aromatic system containing one or two rings, wherein the rings may be bound together in a fused manner. The term "aryl" includes monocyclic or bicyclic aryls, such as aromatic groups of phenyl, naphthyl, and tetrahydronaphthyl. Preferably the aryl is a $C_6$-$C_{10}$ aryl, more preferably the aryl is a phenyl and a naphthyl, and most preferably a naphthyl. The aryl may be substituted or unsubstituted.

"Heteroaryl" refers to an aromatic 5- to 6-membered monocyclic ring or an 8- to 10-membered (e.g., 8, 9, 10-membered) bicyclic ring, which may include 1 to 4 (e.g. 1, 2, 3, 4) atoms selected from nitrogen, oxygen and/or sulfur. Preferred is bicyclic heteroaryl. Examples of "heteroaryl" include, but are not limited to, furyl, pyridyl, 2-oxo-1,2-dihydropyridyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzothienyl, benzimidazolyl, indolyl, isoindolyl, 1,3-dioxo-isoindolyl, quinolyl, indazolyl, benzoisothiazolyl, benzoxazolyl, benzoisoxazolyl.

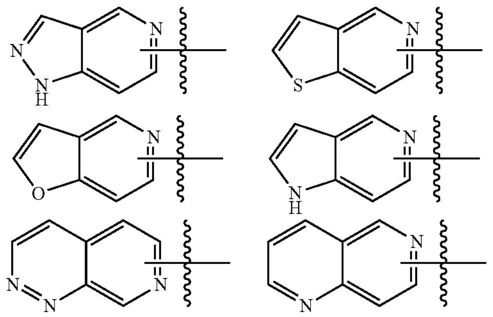

-continued

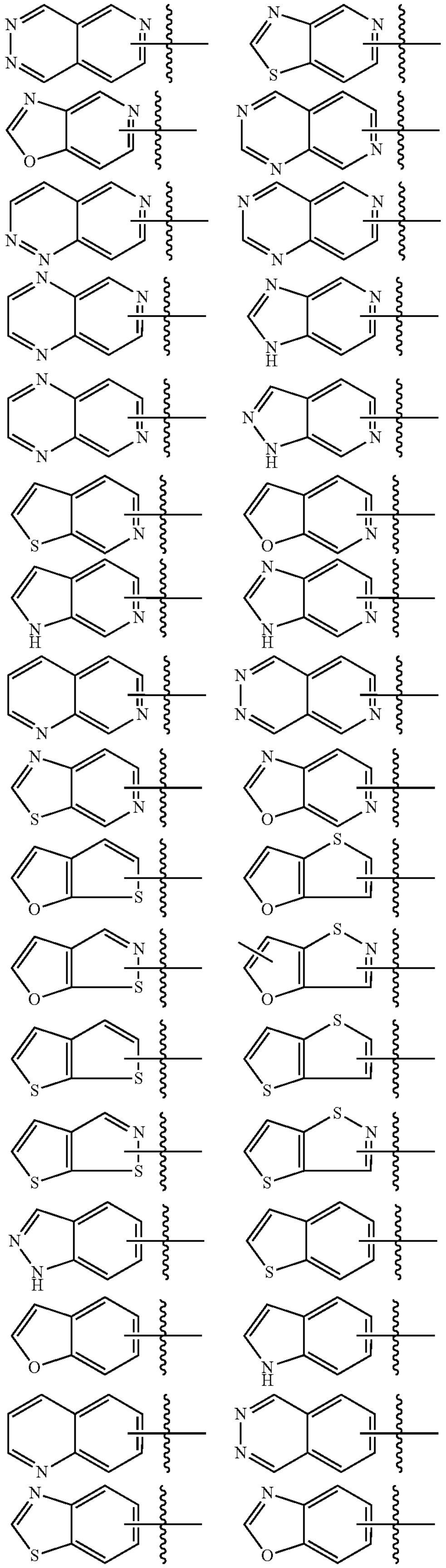

-continued

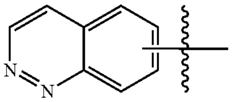
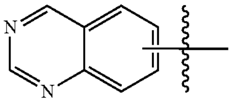
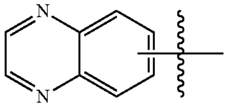
or
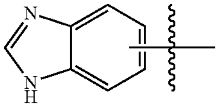
;

the heteroaryl may be substituted or unsubstituted.

"Fused ring" refers to a polycyclic group with two or more cyclic structures sharing a pair of atoms with each other. One or more rings may contain one or more double bonds, but at least one ring does not have a completely conjugated π-electron aromatic system, wherein ring atoms are selected from zero, one or more (for example, 1, 2, 3, 4) heteroatoms selected from nitrogen, oxygen, $P(O)_n$ or $S(O)_n$ (wherein n is selected from 0, 1 or 2), and the remaining ring atoms are carbon. The fused ring is preferably a bicyclic or tricyclic fused ring, wherein the bicyclic fused ring is preferably a fused ring of aryl or heteroaryl and monocyclic heterocyclyl or monocyclic cycloalkyl. Preferably 7 to 14 membered (for example, 7, 8, 9, 10, 11, 12, 13, 14 membered), and more preferably 8 to 10 membered. Examples of "fused ring" include, but are not limited to:

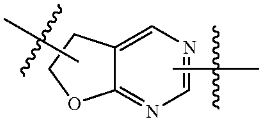
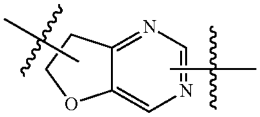
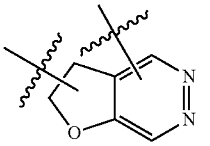
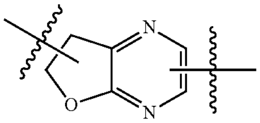
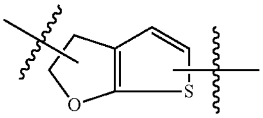
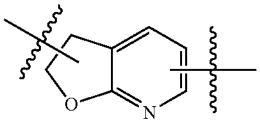
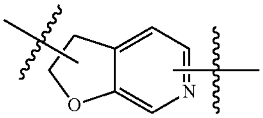
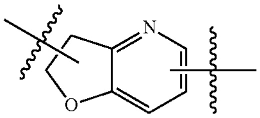
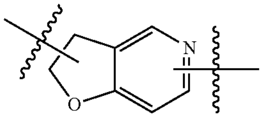
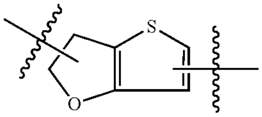
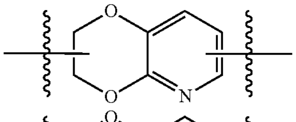
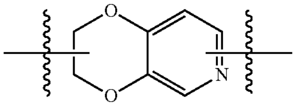
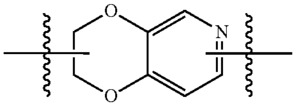

-continued

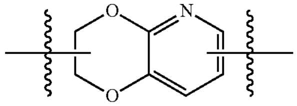
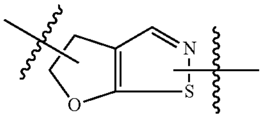
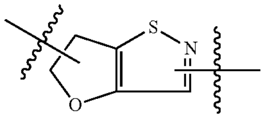
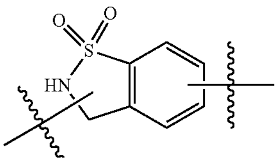
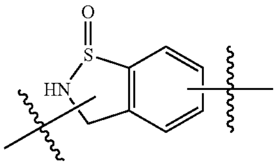
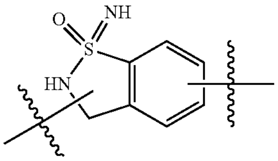
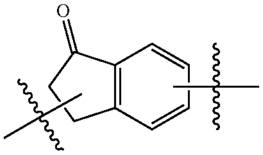
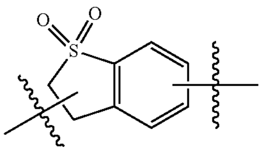
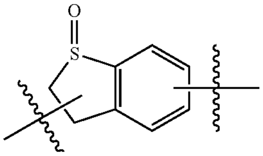
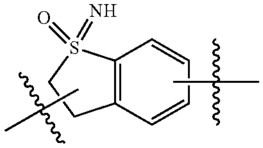
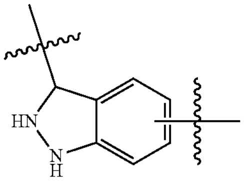
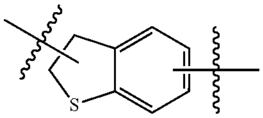
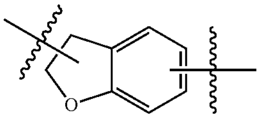
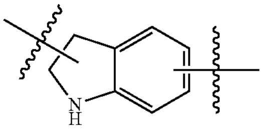
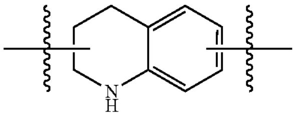
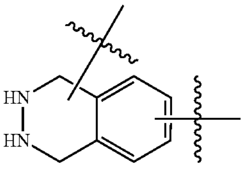
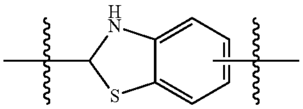
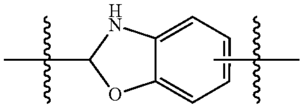
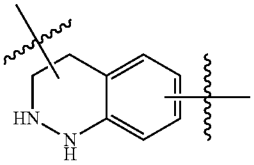
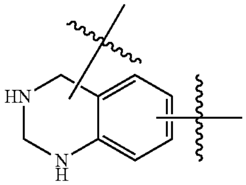
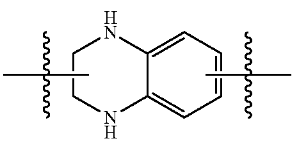

-continued

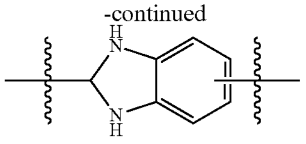

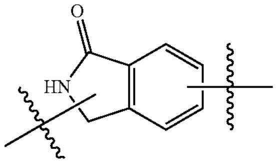

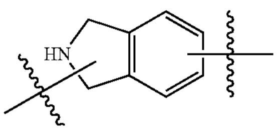

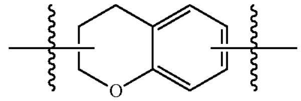

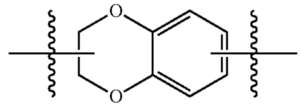

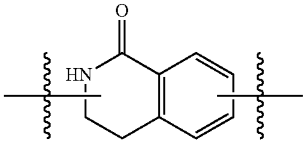

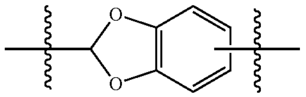

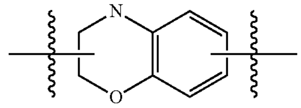

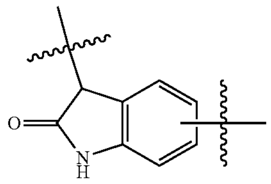

or

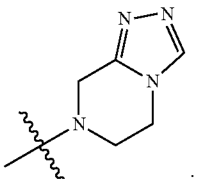

.

"Alkoxy" refers to a group of (alkyl-O—), wherein, the alkyl is defined herein. $C_1$-$C_6$ alkoxy is preferred. Examples include, but are not limited to: methoxy, ethoxy, n-propoxy, isopropoxy, n-butoxy, isobutoxy, tert-butoxy, and the like.

"Acyl" refers to the monovalent atomic group remaining after removing the hydroxyl from an organic or inorganic oxygen-containing acid, preferably $C_1$-$C_6$ alkyl-C(O)-alkyl, $C_3$-$C_6$ cycloalkyl-C(O)—. Examples include, but are not limited to: formyl, acetyl, n-propionyl, isopropionyl, cyclopropionyl, cyclobutyryl, etc.

"Oxo" refers to ═O.

"Hydroxyalkyl" refers to hydroxyl-substituted alkyl.

"Haloalkyl" refers to halogen-substituted alkyl.

"Hydroxy" refers to —OH group.

"Halogen" refers to fluorine, chlorine, bromine and iodine.

"Amino" refers to —$NH_2$.

"Cyano" refers to —CN.

"Nitro" refers to —$NO_2$.

"Benzyl" refers to —$CH_2$-phenyl.

"DMSO" refers to dimethyl sulfoxide.

"HATU" refers to 2-(7-azabenzotriazole)-N,N,N',N'-tetramethylurea hexafluorophosphate.

"BOP Reagent" refers to benzotriazole-1-bis(trimethylamino)phosphonium-hexafluorophosphate.

"Leaving group", also known as leaving group, is an atom or functional group separated from a larger molecule in a chemical reaction, which is a term used in nucleophilic substitution reaction and elimination reaction. In nucleophilic substitution reaction, a reactant attacked by a nucleophilic reagent is called substrate, while an atom or atomic group broken away with a pair of electrons in the substrate molecule is called leaving group. A Group that accepts electrons easily and has strong ability of bearing negative charges is a good leaving group. When the pKa of a conjugated acid of the leaving group is smaller, it is easier for the leaving group to separate from other molecules. The reason is that when the pKa of the conjugated acid of the leaving group is smaller, the corresponding leaving group does not need to be combined with other atoms, and the tendency to exist in the form of anions (or electrically neutral leaving group) is enhanced. Common leaving groups include but are not limited to, halogen, mesyl, —OTs, or —OH.

"Substituted" means that one or more hydrogen atoms in a group, preferably at most 5, more preferably 1 to 3 hydrogen atoms, are independently substituted by a corresponding number of substituents. It goes without saying that the substituents are only in their possible chemical positions, and those skilled in the art will be able to determine (by experiment or theory) substitutions that may or may not be possible without undue effort. For example, the combination of an amino or hydroxyl group having free hydrogen(s) with a carbon atom having an unsaturated (e.g., olefinic) bond may be unstable.

As used in this specification, "substitute" or "substituted", unless otherwise specified, means that a group may be substituted by one or more substituents.

As used in this specification, "substitute" or "substituted", unless otherwise specified, means that a group may be substituted by one or more substituents selected from the following: alkyl, alkenyl, alkynyl, alkoxy, alkylthio, alkylamino, halogen, mercapto, hydroxyl, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, carboxylate, ═O, —C(O)$R^{5'}$, —C(O)O$R^{5'}$, —NHC(O)$R^{5'}$, —NHC(O)O$R^{5'}$, —N$R^{6'}R^{7'}$, —C(O)N$R^{6'}R^{7'}$, —$CH_2$NHC(O)O$R^{5'}$, —$CH_2$N$R^{6'}R^{7'}$ or —$S(O)_rR^{5'}$, wherein:

$R^{5'}$ is selected from hydrogen atom, alkyl, cycloalkyl, heterocyclyl, aryl or heteroaryl, wherein the alkyl, cycloalkyl, heterocyclyl, aryl or heteroaryl is optionally further substituted by one or more substituents selected from the following groups: hydroxy, halogen, nitro, cyano, alkyl, alkoxy, haloalkyl, haloalkoxy, cycloalkyl, heterocyclyl, aryl, heteroaryl, ═O, —C(O)$R^{8'}$, —C(O)O$R^{8'}$, —OC(O)$R^{8'}$, —N$R^{9'}R^{10'}$, —C(O)N$R^{9'}R^{10'}$, —$SO_2$N$R^{9'}R^{10'}$ or —N$R^{9'}$C(O)$R^{10'}$;

$R^{6'}$ and $R^{7'}$ are each independently selected from hydrogen atoms, hydroxyl, halogen, alkyl, alkoxy, cycloalkyl, heterocyclyl, aryl or heteroaryl, wherein the alkyl, alkoxy, cycloalkyl, heterocyclyl, aryl or heteroaryl is optionally further substituted by one or more substituents selected from the following groups: hydroxy, halogen, nitro, cyano, alkyl, alkoxy, cycloalkyl, heterocyclyl, aryl, heteroaryl, ═O, —C(O)$R^{8'}$, —C(O)O$R^{8'}$, —OC(O)$R^{8'}$, —N$R^{9'}R^{10'}$, —C(O)N$R^{9'}R^{10'}$, —$SO_2$N$R^{9'}R^{10'}$ or —N$R^{9'}$C(O)$R^{10'}$;

Alternatively, $R_6$ and $R_7$ together with the atoms to which they are bound form a 4- to 8-membered heterocyclyl, wherein the 4- to 8-membered heterocyclyl includes one or more N, O or $S(O)_r$, and the 4- to 8-membered heterocyclyl is optionally further substituted by one or more substituents selected from the following groups: hydroxyl, halogen, nitro, cyano, alkyl, alkoxy, cycloalkyl, heterocyclyl, aryl, heteroaryl, =O, —C(O)$R^{8'}$, —C(O)O$R^{8'}$, —OC(O)$R^{8'}$, —N$R^{9'}R^{10'}$, —C(O)N$R^{9'}R^{10'}$, —$SO_2$N$R^{9'}R^{10'}$ or —N$R^{9'}$C(O)$R^{10'}$;

$R^1$, $R^{9'}$ and $R^{10'}$ are each independently selected from hydrogen atoms, alkyl, amino, cycloalkyl, heterocyclyl, aryl or heteroaryl, wherein the alkyl, cycloalkyl, heterocyclyl, aryl or heteroaryl is optionally further substituted by one or more substituents selected from the following groups: hydroxy, halogen, nitro, amino, cyano, alkyl, alkoxy, cycloalkyl, heterocyclyl, aryl, heteroaryl, carboxyl or carboxylate;

r is 0, 1 or 2.

The compounds of the present invention may include asymmetric centers or chiral centers and therefore exist in different stereoisomeric forms. It is contemplated that all stereoisomeric forms of the compounds of the present invention, including, but not limited to, a diastereoisomer, an enantiomer, an atropisomer and a geometric (conformational) isomer, as well as mixtures thereof (such as a mixture of racemates), are within the scope of the invention.

Unless otherwise specified, the structures described herein also include all isomers of this structure (e.g., diastereoisomer, enantiomer, atropisomer and geometric (conformational) isomer forms); For example, R and S configurations of each asymmetric center, (Z) and (E) double bond isomers, and (Z) and (E) conformational isomers. Therefore, an individual stereoisomer, mixtures of enantiomers, mixtures of diastereomers, and mixtures of geometric (conformational) isomers of the compounds of the present invention are within the scope of the present invention.

"Pharmaceutically acceptable salts" refer to some salts of the above compounds which retain their original biological activity and are suitable for pharmaceutical use. The pharmaceutically acceptable salt of a compound represented by general formula (I) may be a metal salt, an amine salt formed with a suitable acid.

"Pharmaceutical composition" represents a mixture containing one or more compounds described herein, or physiologically acceptable salts or prodrugs thereof, and other chemical components, as well as other components such as physiologically acceptable carriers and excipients. The object of the pharmaceutical composition is to promote the administration to organisms and facilitate the absorption of active ingredients to exert biological activity.

Synthesis Methods of the Compounds of the Present Invention

In order to achieve the objects of the present invention, the following technical solutions are adopted by the present invention:

The preparation method of a compound represented by general formula (I) of the present invention or a stereoisomer, a tautomer, or a pharmaceutically acceptable salt thereof, the method comprises the following steps:

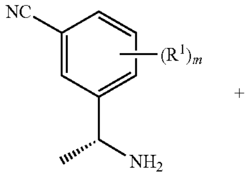

(IA)

-continued

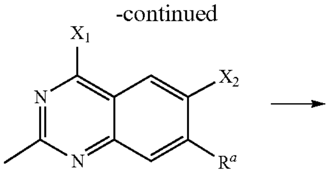

(IB)

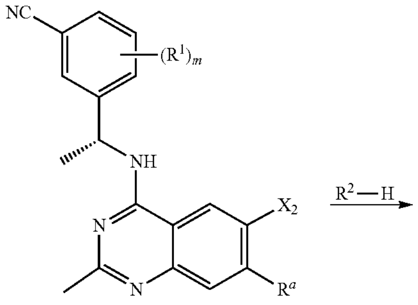

(IC)

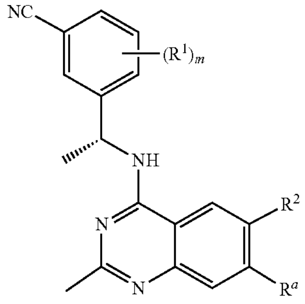

(I)

subjecting the compound represented by general formula (IA) and the compound represented by general formula (IB) to a condensation reaction to obtain the compound represented by general formula (IC); and subjecting the compound represented by general formula (IC) and $R^2$—H to a Buckward coupling reaction, and optionally further removing a protecting group and subjecting the obtained compound to an amino substitution reaction to obtain the compound represented by general formula (I);

wherein:

$X^1$ is a leaving group, preferably hydroxyl;

$X^2$ is a leaving group, preferably halogen, more preferably bromine;

$R^1$, $R^2$, $R^a$ and m are defined as in general formula (I).

DESCRIPTION OF THE DRAWINGS

FIG. 1 shows the changes in tumor volume of each group of mice in the NCI-H2122 model with the compounds of the present invention.

EMBODIMENTS

The following examples are used to further describe the present invention, but these examples do not limit the scope of the present invention.

EXAMPLES

The examples show the preparation of representative compounds represented by formula (I) and related structural identification data. It should be noted that the following examples are only used to illustrate the present invention, but not to limit the present invention. $^1$H NMR spectrum was determined by Bruker instrument (400 MHz), and chemical shift was expressed in ppm. Tetramethylsilane internal standard (0.00 ppm) was used. $^1$H NMR was expressed as follows: s=singlet, d=doublet, t=triplet, m=multiplet, br=broadened, dd=doublet of doublets, and dt=doublet of triplets. If a coupling constant was provided, it was in the unit of Hz.

A mass spectrum was determined by LC/MS, and an ionization method may be ESI or APCI.

Yantai Huanghai HSGF254 or Qingdao GF254 silica gel plates were used as silica gel plates for thin layer chromatography. The specifications of silica gel plates used in thin layer chromatography (TLC) were 0.15 mm-0.2 mm. The specifications used for the separation and purification of products by thin layer chromatography were 0.4 mm-0.5 mm.

Yantai Huanghai Silica Gel (200-300 mesh) was generally used as column chromatography carrier.

In the following examples, all temperatures were in degrees Celsius unless otherwise specified, and the various starting materials and reagents were commercially available or synthesized according to known methods unless otherwise specified, and the commercially available materials and reagents were used directly without further purification. Unless otherwise specified, commercially available manufacturers, including but not limited to, Shanghai Haohong Biomedical Technology Co., Ltd., Shanghai Shaoyuan Reagent Co., Ltd., Shanghai Bide Pharmaceutical Technology Co., Ltd., Sanen Chemical Technology (Shanghai) Co., Ltd. and Shanghai Lingkai Pharmaceutical Technology Co., Ltd.

$CD_3OD$: deuterated methanol.

$CDCl_3$: deuterated chloroform.

DMSO-$d_6$: deuterated dimethyl sulfoxide.

The nitrogen atmosphere refers to that the reaction flask is equipped with a nitrogen balloon with a volume of about 1 L.

Unless otherwise specified, the solution in the reaction used in examples refers to an aqueous solution.

The compounds were purified using a silica gel column chromatography and thin layer chromatography eluent/developing agent system, wherein the system was selected from: A: petroleum ether and ethyl acetate system; B: dichloromethane and methanol system; C: dichloromethane and ethyl acetate system, and D: dichloromethane and ethanol system. The volume ratios of the solvents varied according to the polarity of the compounds, and a small amount of acidic or basic reagents such as acetic acid or triethylamine may also be added.

Example 1

(R)-3-(1-((7-methoxy-2-methyl-6-morpholinoquinazolin-4-yl)amino)ethyl)-2-methylbenzonitrile

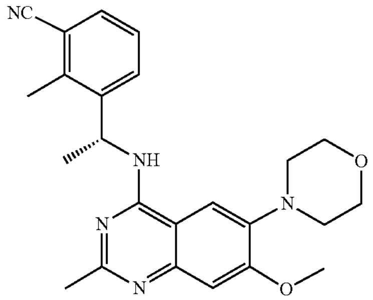

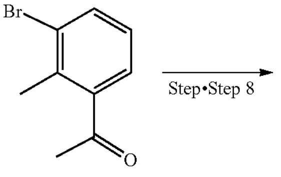

1a

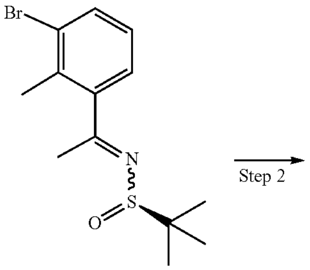

1b

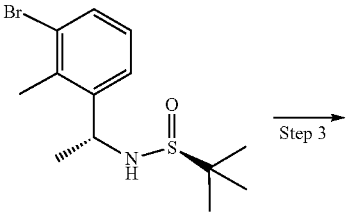

1c

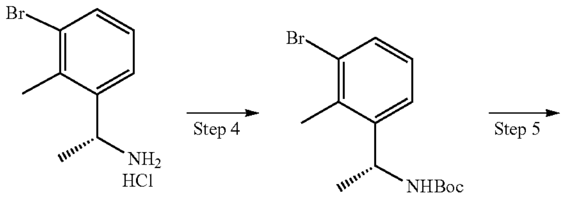

1d 1e

-continued

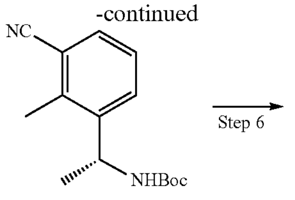

1f

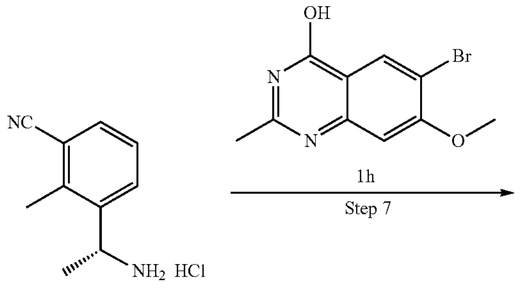

1h

1g

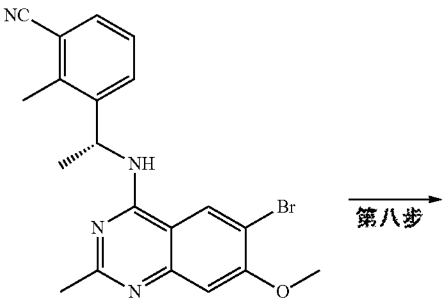

1i

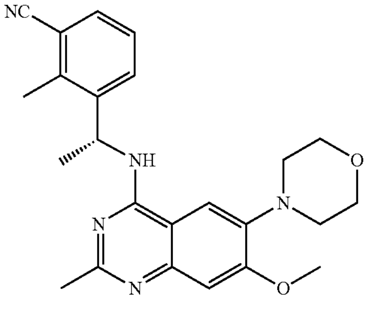

1

Step 1

Synthesis of N-(1-(3-bromo-2-methylphenyl)ethylidene)-2-methylpropane-2-sulfinamide 1-(3-bromo-2-methylphenyl)ethane-1-one 1a (12 g, 56.32 mmol), (R)-2-methylpropane-2-sulfonimide (8.87 g, 73.22 mmol), tetraethyl titanate (19.27 g, 84.48 mmol), 100 mL of tetrahydrofuran were added to a 250 mL flask, nitrogen was replaced three times, and the above mixture reacted at 80 degrees for 7 hours. After returning to room temperature, 30 mL of water was added. The reaction solution was filtered with diatomite, washed with ethyl acetate, washed three times with water, dried over anhydrous sodium sulfate, filtered and concentrated, mixed with silica gel, and passed through a column passing machine to obtain 14 g of N-(1-(3-bromo-2-methylphenyl)ethylidene)-2-methylpropane-2-sulfinamide 1b, yield 79%.

MS m/z (ESI): 316.1[M+1]$^+$

Step 2

Synthesis of (S)-N-((R)-1-(3-bromo-2-methylphenyl)ethyl)-2-methylpropane-2-sulfinamide N-(1-(3-bromo-2-methylphenyl)ethylidene)-2-methylpropane-2-sulfinamide 1b (7 g, 22.13 mmol), 30 mL of tetrahydrofuran was added to a 250 mL reaction flask, 80 mL of 0.5 M 9-BBN in tetrahydrofuran was slowly added under ice bath, and the reaction was continued for 5 hours after the system was returned to room temperature. The reaction solution was sent to LC-MS to detect the disappearance of raw materials, quenched by adding saturated ammonium chloride solution, concentrated to remove tetrahydrofuran, ethyl acetate was added, the obtained system was washed three times with water, and dried over anhydrous sodium sulfate. The mixture was purified through a column passing machine to obtain 6.0 g of (S)-N-((R)-1-(3-bromo-2-methylphenyl)ethyl)-2-methylpropane-2-sulfinamide 1c, yield 85%.

MS m/z (ESI): 318.2[M+1]$^+$

Step 3

Synthesis of (R)-1-(3-bromo-2-methylphenyl)ethane-1-amine hydrochloride (S)-N-((R)-1-(3-bromo-2-methylphenyl)ethyl)-2-methylpropane-2-sulfinamide 1c (4 g, 12.57 mmol) was added to a 25 mL reaction flask, 10 mL of hydrogen chloride/dioxane solution was added and the obtained system was stirred at room temperature. LC-MS detected that the raw materials had reacted completely, the solvent was concentrated, and diethyl ether was added and stirred to precipitate 1.8 g of (R)-1-(3-bromo-2-methylphenyl)ethane-1-amine hydrochloride 1d, yield 58%.

MS m/z (ESI): 214.0[M+1]$^+$

Step 4

Synthesis of tert-butyl (R)-(1-(3-bromo-2-methylphenyl)ethyl)carbamate (R)-1-(3-bromo-2-methylphenyl)ethane-1-amine hydrochloride 1d (1.3 g, 5.2 mmol), di-tert-butyl dicarbonate (1.19 g, 10.90 mmol) and dichloromethane (8 mL) were added to a 100 mL flask, diisopropylethylamine (1.34 g, 10.4 mmol) was slowly added under ice bath, and the above mixture reacted at room temperature for 3 hours. 300 mL of dichloromethane was added to the reaction solution, and the reaction solution was washed three times with water, dried over anhydrous sodium sulfate, and purified through a column passing machine to obtain 3.0 g of tert-butyl (R)-(1-(3-bromo-2-methylphenyl)ethyl)carbamate 1e, yield 93%.

MS m/z (ESI): 314.1[M+1]$^+$

Step 5

Synthesis of tert-butyl (R)-(1-(3-cyano-2-methylphenyl)ethyl)carbamate tert-butyl (R)-(1-(3-bromo-2-methylphenyl)ethyl)carbamate 1e (2 g, 6.37 mmol), $Zn(CN)_2$ (1.49 g, 12.73 mmol), $Pd(PPh_3)_4$ (735.52 mg, 636.50 μmol), DMF (8 mL) were added to a 50 mL flask, nitrogen was replaced three times, and the above mixture reacted at 140 degrees for 8 hours. After returning to room temperature, ethyl acetate was added to the reaction solution, the reaction solution was washed three times with water, dried over anhydrous sodium sulfate, and passed through a column passing machine to obtain 0.8 g of tert-butyl (R)-(1-(3-cyano-2-methylphenyl)ethyl)carbamate if, yield 49%.

MS m/z (ESI): 261.2[M+1]$^+$

Step 6

Synthesis of (R)-3-(1-aminoethyl)-2-methylbenzonitrile hydrochloride tert-butyl (R)-(1-(3-cyano-2-methylphenyl)ethyl)carbamate if (4.5 g, 17.29 mmol) and 20 mL of 4M hydrogen chloride/dioxane solution were added to a 100 mL flask, the above mixture reacted at room temperature for 5 hours, and a white solid precipitated. Diethyl ether was added to the reaction solution, and the reaction solution was filtered to obtain 3.0 g of (R)-3-(1-aminoethyl)-2-methylbenzonitrile hydrochloride 1g, yield 89%.

MS m/z (ESI): 161.1[M+1]$^+$

Step 7

(R)-3-(1-((6-bromo-7-methoxy-2-methylquinazolin-4-yl)amino)ethyl)-2-methylbenzonitrile 6-bromo-7-methoxy-2-methylquinazolin-4-ol 1h (500 mg, 1.86 mmol, prepared according to published patent WO 2018115380), (R)-3-(1-aminoethyl)-2-methylbenzonitrile hydrochloride 1g (562.3 mg, 2.42 mmol), BOP Reagent (1.07 g, 2.42 mmol), 1,8-diazabicyclo[5.4.0]undec-7-ene (848.62 mg, 5.57 mmol) and N,N-dimethylformamide (5 mL) were added sequentially into a 15 mL reaction flask, the above mixture was stirred at room temperature overnight. LC-MS showed that the reaction was completed. Ethyl acetate (30 mL) was added to the reaction solution, and the reaction solution was washed with water (30 mL×3). The organic phase of the reaction solution was dried over anhydrous sodium sulfate, filtered, and concentrated under reduced pressure. The obtained residue was separated and purified by silica gel column chromatography (eluent: system A) to obtain 502 mg of (R)-3-(1-((6-bromo-7-methoxy-2-methylquinazolin-4-yl)amino)ethyl)-2-methylbenzonitrile 1i, yield 66%.

MS m/z (ESI): 411.0 [M+H]$^+$

Step 8

(R)-3-(1-((7-methoxy-2-methyl-6-morpholinoquinazolin-4-yl)amino)ethyl)-2-methylbenzonitrile (R)-3-(1-((6-bromo-7-methoxy-2-methylquinazolin-4-yl)amino)ethyl)-2-methylbenzonitrile 1i (115.00 mg, 0.28 mmol), morpholine (48.72 mg, 0.56 mmol), tris(dibenzylideneacetone)dipalladium (25.58 mg, 0.028 mmol), sodium tert-butoxide (80.61 mg, 0.84 mmol) and 4,5-bisdiphenylphosphine-9,9-dimethylxanthene (32.36 mg, 0.056 mmol) were added sequentially to 1,4-dioxane (5 mL). Under nitrogen atmosphere, the above mixture was heated to 90° C. and stirred continuously for 5 hours. LC-MS showed that the reaction was completed. The reaction solution was cooled to room temperature and concentrated under reduced pressure. The obtained residue was separated and purified sequentially by silica gel column chromatography (eluent: system B) and thin layer chromatography (developing agent: system B) to obtain 24 mg of (R)-3-(1-((7-methoxy-2-methyl-6-morpholinequinazolin-4-yl)amino)ethyl)-2-methylbenzonitrile 1, yield 20%.

MS m/z (ESI): 418.2 [M+H]$^+$ $^1$H NMR (400 MHz, DMSO-$d_6$) δ 8.51 (s, 1H), 7.83 (dd, J=8.0, 1.4 Hz, 1H), 7.71 (s, 1H), 7.63 (dd, J=7.7, 1.4 Hz, 1H), 7.37 (t, J=7.8 Hz, 1H), 7.03 (s, 1H), 5.68 (m, 1H), 3.89 (s, 3H), 3.79 (t, J=4.5 Hz, 4H), 3.09 (q, J=3.8 Hz, 4H), 2.72 (s, 3H), 2.35 (s, 3H), 1.57 (d, J=7.0 Hz, 3H) ppm.

Example 2

(R)-3-(1-((6-(4-acetylpiperazin-1-yl)-7-methoxy-2-methylquinazolin-4-yl)amino)ethyl)-2-methylbenzonitrile

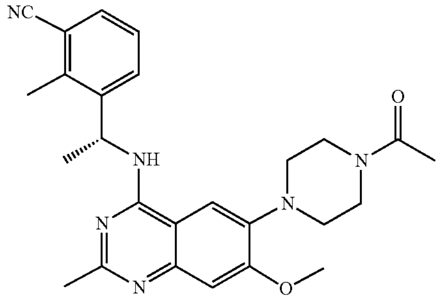

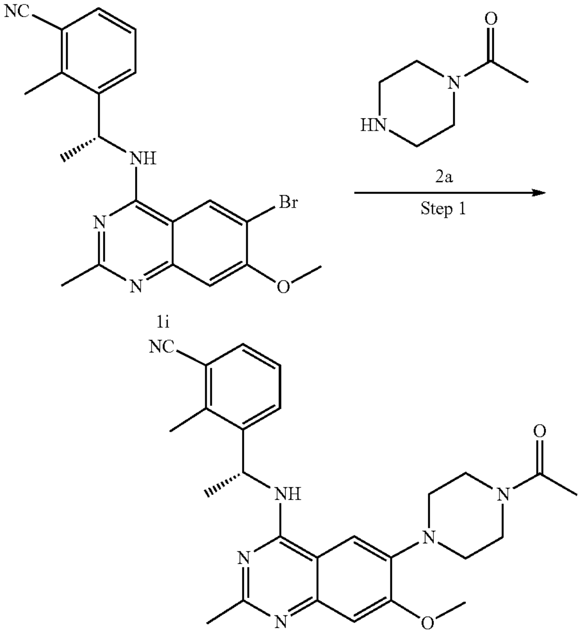

1i

2

(R)-3-(1-((6-bromo-7-methoxy-2-methylquinazolin-4-yl)amino)ethyl)-2-methylbenzonitrile 1i (30 mg, 0.073 mmol), 1-(piperazin-1yl)ethan-1-one 2a (9.35 mg, 0.073 mmol, commercially available), tris(dibenzylideneacetone)dipalladium (10 mg, 0.011 mmol), sodium tert-butoxide (14.02 mg, 0.146 mmol) and 4,5-bisdiphenylphosphine-9,9-dimethylxanthene (42.20 mg, 0.073 mmol) were added sequentially to 1,4-dioxane (5 mL). Under nitrogen atmosphere, the above mixture was heated to 90° C. and reacted for 5 hours. LC-MS showed that the reaction was completed. The reaction solution was cooled to room temperature and concentrated under reduced pressure. The obtained residue was purified by silica gel column chromatography (eluent: system B) to obtain mg of (R)-3-(1-((6-(4-acetylpiperazin-1-yl)-7-methoxy-2-methylquinazolin-4-yl)amino) ethyl)-2-methylbenzonitrile 2, yield 60%.

MS m/z (ESI): 459.5 $[M+H]^+$ $^1$H NMR (400 MHz, DMSO-$d_6$) δ 9.79 (s, 1H), 7.90 (s, 1H), 7.81 (d, J=7.9 Hz, 1H), 7.70 (d, J=7.6 Hz, 1H), 7.43 (t, J=7.8 Hz, 1H), 7.09 (s, 1H), 5.80 (t, J=7.0 Hz, 1H), 3.99 (s, 3H), 3.65 (d, J=9.2 Hz, 4H), 3.16-2.98 (m, 4H), 2.68 (s, 3H), 2.53 (s, 3H), 2.06 (s, 3H), 1.63 (d, J=6.9 Hz, 3H) ppm.

Example 3

3-((1R)-1-((7-methoxy-2-methyl-6-(6-oxohexahydropyrrolo[1,2-a]pyrazin-2(1H)-yl)quinazolin-4-yl)amino)ethyl)-2-methylbenzonitrile

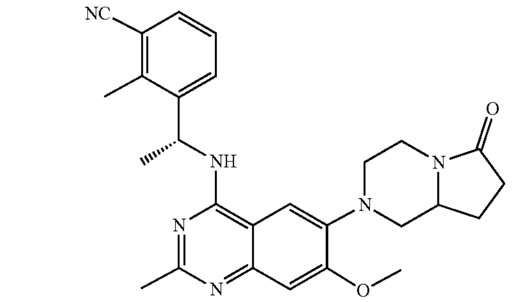

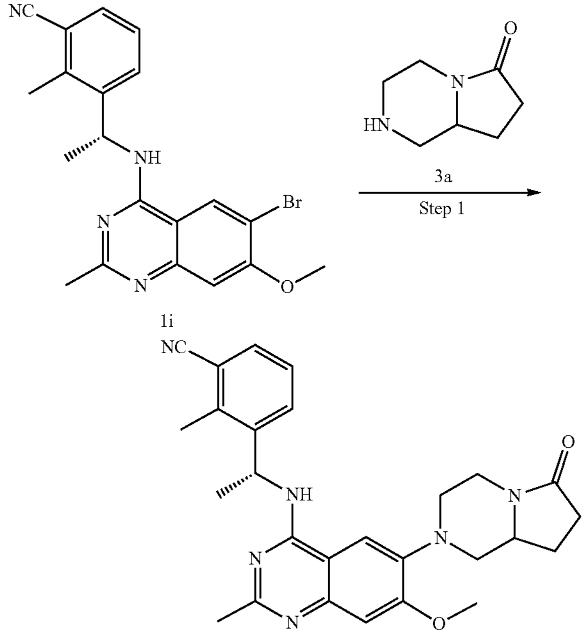

1i

3

(R)-3-(1-((6-bromo-7-methoxy-2-methylquinazolin-4-yl)amino)ethyl)-2-methylbenzonitrile 1i (100 mg, 0.243 mmol), hexahydropyrrolo[1,2-a]pyrazin-6-one 3a (51.12 mg, 0.367 mmol, commercially available), methanesulfonic acid (2-dicyclohexylphosphino-2',6'-diisopropoxy-1,1'-biphenyl) (2-amino-1,1'-biphenyl-2-yl) palladium(II)(40.72 mg, 0.049 mmol) and sodium tert-butoxide (116.83 mg, 1.22 mmol) were added sequentially to 1,4-dioxane (5 mL). Under nitrogen atmosphere, the above mixture was heated to 100° C. and stirred continuously for 5 hours. LC-MS showed that the reaction was completed. The reaction solution was cooled to room temperature and concentrated under reduced pressure. The obtained residue was purified by silica gel column chromatography (eluent: system B) to obtain 18 mg of 3-((1R)-1-((7-methoxy-2-methyl-6-(6-oxohexahydropyrrolo[1,2-a]pyrazin-2(1H)-yl) quinazolin-4-yl)amino) ethyl)-2-methylbenzonitrile 3, yield 15%.

MS m/z (ESI): 471.3 $[M+H]^+$ $^1$H NMR (400 MHz, DMSO-$d_6$) δ 8.19 (d, J=7.0 Hz, 1H), 7.81 (d, J=8.0 Hz, 1H), 7.68 (s, 1H), 7.64 (d, J=7.6 Hz, 1H), 7.37 (t, J=7.8 Hz, 1H), 7.03 (s, 1H), 5.66 (t, J=7.0 Hz, 1H), 3.95 (d, J=12.6 Hz, 1H), 3.91 (s, 3H), 3.79 (d, J=7.1 Hz, 1H), 3.62 (d, J=11.4 Hz, 1H), 3.46 (d, J=11.6 Hz, 1H), 3.01 (dd, J=13.2, 10.0 Hz, 1H), 2.73 (s, 3H), 2.60 (d, J=10.0 Hz, 1H), 2.46-2.35 (m, 2H), 2.32 (s, 4H), 2.20 (d, J=10.2 Hz, 1H), 1.74-1.63 (m, 1H), 1.56 (d, J=7.0 Hz, 3H) ppm.

Example 4

(R)-3-(1-((7-methoxy-2-methyl-6-(3-oxa-9-azaspiro[5.5]undecan-9-yl)quinazolin-4-yl)amino)ethyl)-2-methylbenzonitrile

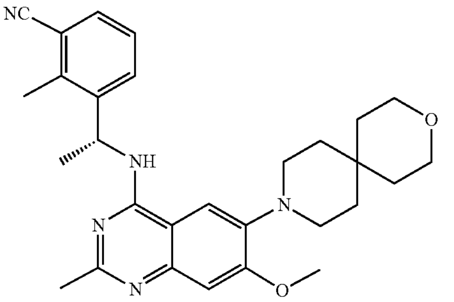

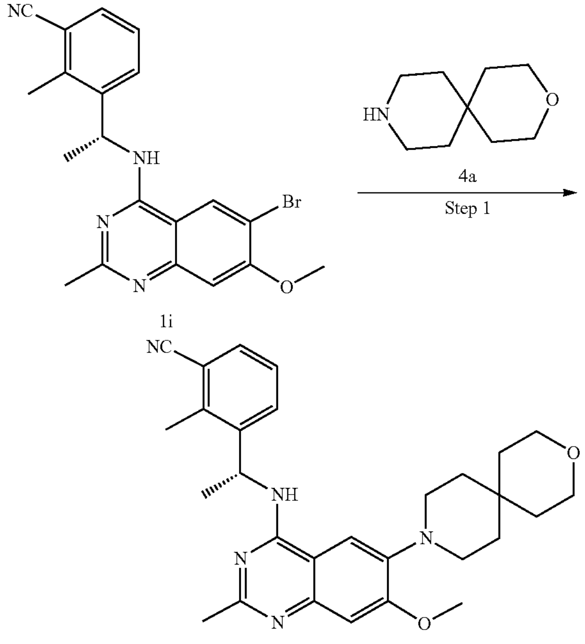

1i

4

(R)-3-(1-((6-bromo-7-methoxy-2-methylquinazolin-4-yl)amino)ethyl)-2-methylbenzonitrile 1i (100 mg, 0.243 mmol), 3-oxa-9-azaspiro[5.5]undecane 4a (69.91 mg, 0.365 mmol, commercially available), tris(dibenzylideneacetone) dipalladium (44.53 mg, 0.049 mmol), sodium tert-butoxide (93.46 mg, 0.973 mmol), and 4,5-bisdiphenylphosphine-9,9-dimethylxanthene (60.56 mg, 0.097 mmol) were added sequentially to 1,4-dioxane (5 mL). Under nitrogen atmosphere, the above mixture was heated to 125° C. under microwave conditions and stirred continuously for 1 hour. LC-MS showed that the reaction was completed. The reaction solution was cooled to room temperature and concentrated under reduced pressure. The obtained residue was purified by silica gel column chromatography (eluent: system B) to obtain 60 mg of (R)-3-(1-((7-methoxy-2-methyl-6-(3-oxa-9-azaspiro[5.5]undecan-9-yl)quinazoline-4-yl)amino)ethyl)-2-methylbenzonitrile 4, yield 51%.

MS m/z (ESI): 486.3 $[M+H]^+$ $^1$H NMR (400 MHz, DMSO-$d_6$) δ 8.24 (d, J=7.0 Hz, 1H), 7.82 (d, J=7.9 Hz, 1H), 7.71-7.60 (m, 2H), 7.38 (t, J=7.8 Hz, 1H), 6.99 (s, 1H), 5.68 (q, J=7.1 Hz, 1H), 3.89 (s, 3H), 3.62 (t, J=5.3 Hz, 4H), 3.05 (q, J=4.3 Hz, 4H), 2.73 (s, 3H), 2.32 (s, 3H), 1.70 (t, J=5.5 Hz, 3H), 1.54 (q, J=6.2, 5.2 Hz, 8H) ppm.

Example 5

(R)-3-(1-((7-methoxy-2-methyl-6-(2-oxa-7-azaspiro[3.5]nonan-7-yl)quinazolin-4-yl)amino)ethyl)-2-methylbenzonitrile

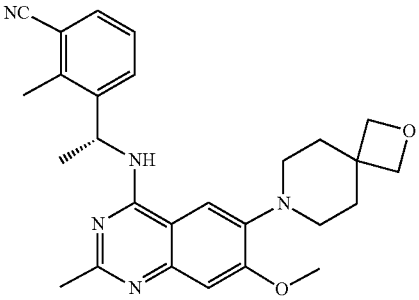

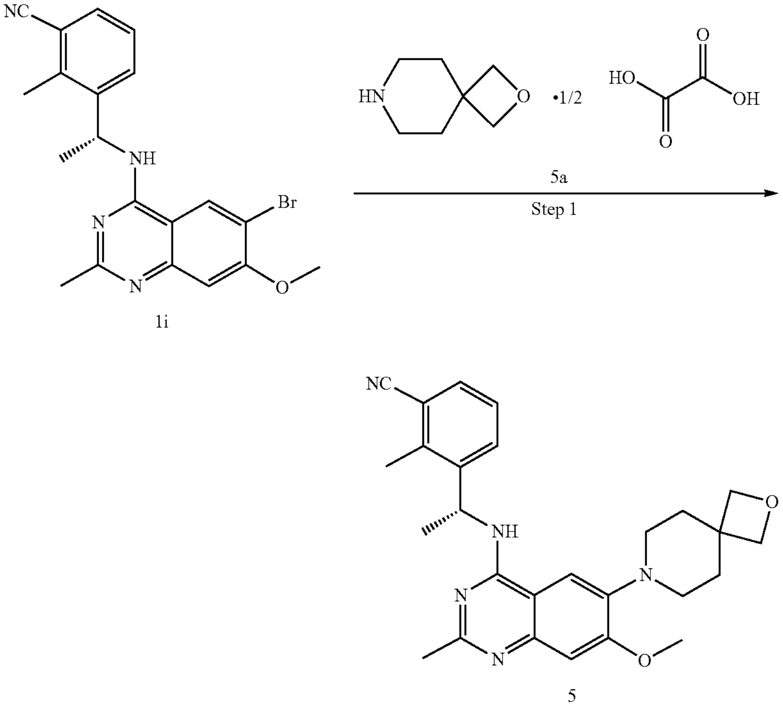

1i

5

(R)-3-(1-((6-bromo-7-methoxy-2-methylquinazolin-4-yl)amino)ethyl)-2-methylbenzonitrile 1i (300 mg, 0.73 mmol), 2-oxa-7-azaspiro[3.5]nonane hemioxalate 5a (200 mg, 1.16 mmol, commercially available), tris(dibenzylideneacetone)dipalladium (66.0 mg, 0.072 mmol), sodium tert-butoxide (280 mg, 2.92 mmol) and 4,5-bisdiphenylphosphine-9,9-dimethylxanthene (91.0 mg, 0.146 mmol) were added sequentially to 1,4-dioxane (15 mL). Under nitrogen atmosphere, the above mixture was heated to 125° C. under microwave conditions and stirred continuously for 1 hour. LC-MS showed that the reaction was completed. The reaction solution was cooled to room temperature and concentrated under reduced pressure. The obtained residue was purified by silica gel column chromatography (eluent: system B) to obtain 120 mg of (R)-3-(1-((7-methoxy-2-methyl-6-(2-oxa-7-azaspiro[3.5]nonan-7-yl)quinazolin-4-yl)amino)ethyl)-2-methylbenzonitrile 5, yield 36%.

MS m/z (ESI): 458.3 $[M+H]^+$ $^1$H NMR (400 MHz, DMSO-$d_6$) δ 8.22-8.15 (m, 1H), 7.81 (d, J=7.9 Hz, 1H), 7.63 (d, J=6.8 Hz, 2H), 7.37 (t, J=7.8 Hz, 1H), 6.99 (s, 1H), 5.66 (t, J=7.0 Hz, 1H), 4.40 (s, 4H), 3.89 (s, 3H), 3.05-2.88 (m, 4H), 2.73 (s, 3H), 2.31 (s, 3H), 1.99 (q, J=5.6, 4.7 Hz, 4H), 1.55 (d, J=7.0 Hz, 3H) ppm.

Example 6

(R)-3-(1-((7-methoxy-2-methyl-6-(4-morpholinopiperidin-1-yl)quinazolin-4-yl)amino)ethyl)-2-methylbenzonitrile

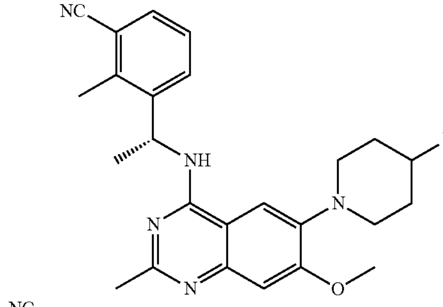

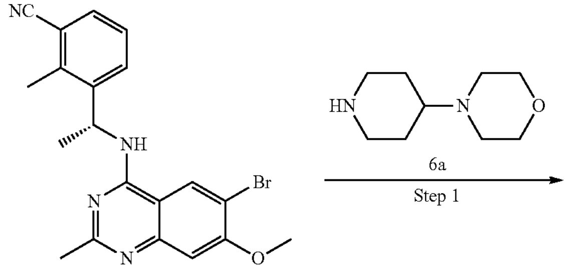

1i

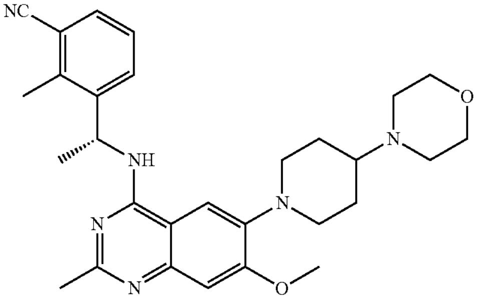

6

(R)-3-(1-((6-bromo-7-methoxy-2-methylquinazolin-4-yl)amino)ethyl)-2-methylbenzonitrile 1i (120 mg, 0.292 mmol), 4-(piperidin-4-yl)morpholine 6a (49.67 mg, 0.292 mmol, commercially available), tris(dibenzylideneacetone)dipalladium (26.73 mg, 0.0292 mmol), sodium tert-butoxide (56.08 mg, 0.584 mmol) and 4,5-bisdiphenylphosphine-9,9-dimethylxanthene (36.33 mg, 0.0584 mmol) were added sequentially to 1,4-dioxane (5 mL). Under nitrogen atmosphere, the above mixture was heated to 100° C. and stirred continuously for 5 hours. LC-MS showed that the reaction was completed. The reaction solution was cooled to room temperature and concentrated under reduced pressure. The obtained residue was purified by silica gel column chromatography (eluent: system B) to obtain 30 mg of (R)-3-(1-((7-methoxy-2-methyl-6-(4-morpholinopiperidin-1-yl)quinazolin-4-yl)amino)ethyl)-2-methylbenzonitrile 6, yield 21%.

MS m/z (ESI): 501.5 $[M+H]^+$ $^1$H NMR (400 MHz, DMSO-$d_6$) δ 8.21 (d, J=7.1 Hz, 1H), 7.82 (d, J=7.9 Hz, 1H), 7.63 (d, J=8.2 Hz, 2H), 7.37 (t, J=7.8 Hz, 1H), 6.99 (s, 1H), 5.71-5.61 (m, 1H), 3.89 (s, 3H), 3.62 (t, J=4.5 Hz, 4H), 3.52 (d, J=10.8 Hz, 3H), 2.73 (s, 3H), 2.66 (q, J=11.2 Hz, 2H), 2.55 (d, J=4.5 Hz, 3H), 2.36 (d, J=11.5 Hz, 1H), 2.32 (s, 3H), 1.91 (d, J=12.0 Hz, 2H), 1.70-1.60 (m, 2H), 1.55 (d, J=7.0 Hz, 3H) ppm.

Example 7

(R)-3-(1-((7-methoxy-2-methyl-6-(2-methyl-1-oxo-2,8-diazaspiro[4.5]decan-8-yl)quinazolin-4-yl)amino)ethyl)-2-methylbenzonitrile

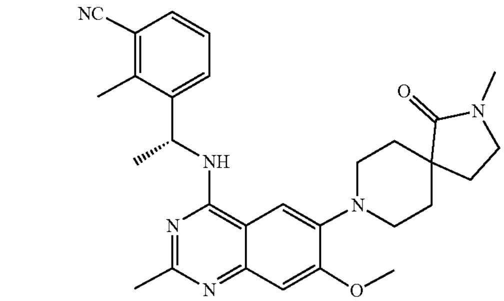

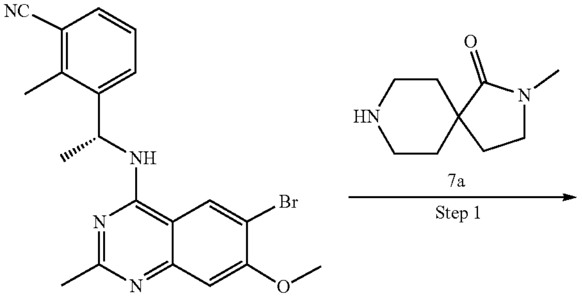

1i

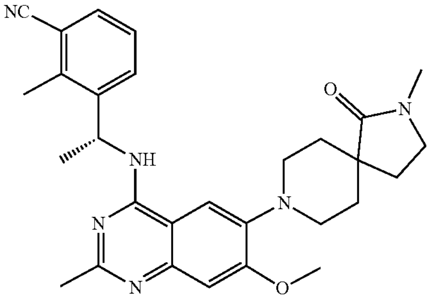

7

(R)-3-(1-((6-bromo-7-methoxy-2-methylquinazolin-4-yl)amino)ethyl)-2-methylbenzonitrile 1i (200 mg, 0.486 mmol), 2-methyl-2,8-diazaspiro[4.5]decan-1-one 7a (81.81 mg, 0.486 mmol, commercially available), tris(dibenzylideneacetone)dipalladium (44.52 mg, 0.0486 mmol), sodium tert-butoxide (93.46 mg, 0.973 mmol) and 4,5-bisdiphenylphosphine-9,9-dimethylxanthene (60.56 mg, 0.097 mmol) were added sequentially to 1,4-dioxane (5 mL). Under nitrogen atmosphere, the above mixture was heated to 100° C. and stirred continuously for 5 hours. LC-MS showed that the reaction was completed. The reaction solution was cooled to room temperature and concentrated under reduced pressure. The obtained residue was purified by silica gel column chromatography (eluent: system B) to obtain 30 mg of (R)-3-(1-((7-methoxy-2-methyl-6-(2-methyl-1-oxo-2,8-diazaspiro[4.5]decan-8-yl)quinazolin-4-yl)amino)ethyl)-2-methylbenzonitrile 7, yield 12%.

MS m/z (ESI): 499.5 [M+H]$^+$ $^1$H NMR (400 MHz, DMSO-$d_6$) δ 9.42 (s, 1H), 7.91-7.78 (m, 2H), 7.70 (d, J=7.7 Hz, 1H), 7.43 (t, J=7.8 Hz, 1H), 7.02 (s, 1H), 5.88-5.72 (m, 1H), 3.98 (s, 3H), 3.53-3.40 (m, 3H), 2.84 (d, J=11.8 Hz, 2H), 2.78 (s, 3H), 2.71 (s, 3H), 2.50 (s, 4H), 2.01 (t, J=6.9 Hz, 2H), 1.97-1.87 (m, 2H), 1.63 (d, J=7.0 Hz, 3H), 1.54 (d, J=13.1 Hz, 2H) ppm.

Example 8

(R)-1-(4-((1-(3-cyano-2-methylphenyl)ethyl)amino)-7-methoxy-2-methylquinazolin-6-yl)piperidine-4-carbonitrile

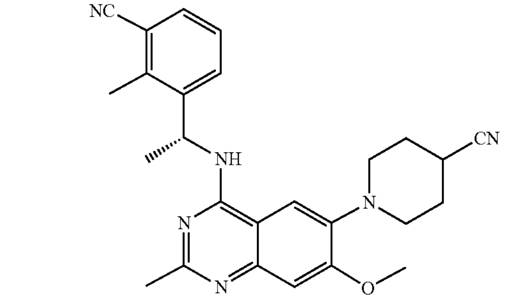

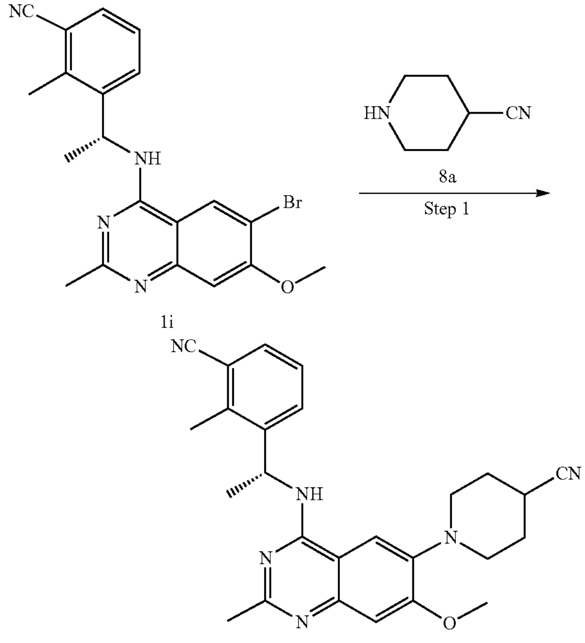

1i

8

(R)-3-(1-((6-bromo-7-methoxy-2-methylquinazolin-4-yl)amino)ethyl)-2-methylbenzonitrile 1i (240 mg, 0.58 mmol), piperidine-4-carbonitrile 8a (96.4 mg, 0.88 mmol, commercially available), $Pd_2(dba)_3$ (80.2 mg, 0.088 mmol), BINAP (109.0 mg, 0.175 mmol) and sodium tert-butoxide (168.2 mg, 1.75 mmol) were added sequentially to the microwave tube. 1,4-dioxane (12 mL) was added, and the above mixture reacted under microwave conditions at 125° C. for 1 hour under nitrogen atmosphere. LC-MS showed that the reaction was completed. The reaction solution was cooled to room temperature and concentrated under reduced pressure. The obtained residue was purified by silica gel column chromatography (eluent: system B) to obtain 65 mg of (R)-1-(4-((1-(3-cyano-2-methylphenyl)ethyl)amino)-7-methoxy-2-methylquinazolin-6-yl)piperidine-4-carbonitrile 8, yield 23%.

MS m/z (ESI): 441.3 [M+H]$^+$ $^1$H NMR (400 MHz, DMSO-$d_6$) δ 8.26 (d, J=6.9 Hz, 1H), 7.81 (d, J=7.9 Hz, 1H), 7.69 (s, 1H), 7.64 (d, J=7.6 Hz, 1H), 7.38 (t, J=7.8 Hz, 1H), 7.01 (s, 1H), 5.66 (t, J=7.0 Hz, 1H), 3.89 (s, 3H), 3.20-3.02 (m, 5H), 2.74 (s, 3H), 2.32 (s, 3H), 2.08-2.04 (m, 2H), 1.96-1.88 (m, 2H), 1.56 (d, J=7.0 Hz, 3H) ppm.

Example 9

3-((1R)-1-((7-methoxy-2-methyl-6-(tetrahydro-1H-furo[3,4-c]pyrrol-5(3H)-yl)quinazolin-4-yl)amino)ethyl)-2-methylbenzonitrile

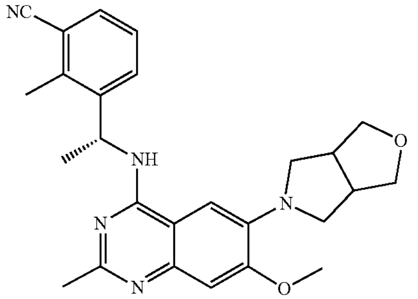

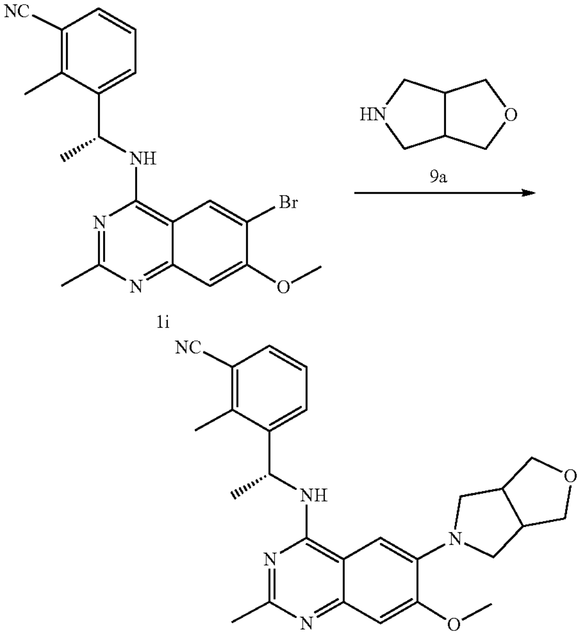

1i

9

(R)-3-(1-((6-bromo-7-methoxy-2-methylquinazolin-4-yl)amino)ethyl)-2-methylbenzonitrile 1i (100 mg, 0.243 mmol), hexahydro-1H-furo[3,4-c]pyrrole 9a (27.51 mg, 0.243 mmol, commercially available), tris(dibenzylideneacetone)dipalladium (22.26 mg, 0.024 mmol), sodium tert-butoxide (46.73 mg, 0.486 mmol) and 4,5-bisdiphenylphosphine-9,9-dimethylxanthene (30.28 mg, 0.049 mmol) were added sequentially to 1,4-dioxane (5 mL). Under nitrogen atmosphere, the above mixture was heated to 100° C. and stirred continuously for 5 hours. LC-MS showed that the reaction was completed. The reaction solution was cooled to room temperature and concentrated under reduced pressure. The obtained residue was purified by silica gel column chromatography (eluent: system B) to obtain 20 mg of 3-((1R)-1-((7-methoxy-2-methyl-6-(tetrahydro-1H-furo[3,4-c]pyrrol-5(3H)-yl)quinazolin-4-yl)amino)ethyl)-2-methylbenzonitrile 9, yield 18%.

MS m/z (ESI): 444.3 [M+H]$^+$ $^1$H NMR (400 MHz, DMSO-$d_6$) δ 9.00 (s, 1H), 7.88 (d, J=7.9 Hz, 1H), 7.72-7.52 (m, 2H), 7.40 (t, J=7.8 Hz, 1H), 7.07 (s, 1H), 5.75 (t, J=7.1 Hz, 1H), 3.94 (s, 3H), 3.88 (t, J=7.4 Hz, 2H), 3.66-3.54 (m, 3H), 3.21 (s, 1H), 3.12 (dd, J=14.5, 6.9 Hz, 2H), 2.97 (s, 2H), 2.72 (s, 3H), 2.42 (s, 3H), 1.61 (d, J=7.0 Hz, 3H) ppm.

Example 10

(R)-3-(1-((7-methoxy-2-methyl-6-(4-methylpiperazin-1-yl)quinazolin-4-yl)amino)ethyl)-2-methylbenzonitrile

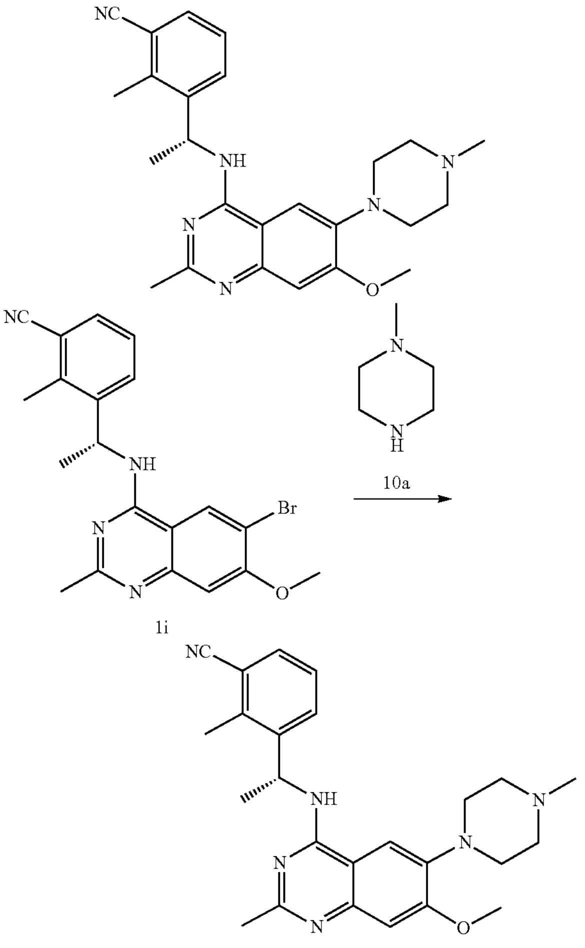

1i

10

(R)-3-(1-((6-bromo-7-methoxy-2-methylquinazolin-4-yl)amino)ethyl)-2-methylbenzonitrile 1i (100 mg, 0.243 mmol), 1-methylpiperazine 10a (48.71 mg, 0.486 mmol, commercially available), tris(dibenzylideneacetone)dipalladium (22.25 mg, 0.024 mmol), sodium tert-butoxide (70.10 mg, 0.729 mmol) and 4,5-bisdiphenylphosphine-9,9-dimethylxanthene (30.28 mg, 0.049 mmol) were added sequentially to 1,4-dioxane (5 mL). Under nitrogen atmosphere, the above mixture was heated to 90° C. and stirred continuously for 5 hours. LC-MS showed that the reaction was completed. The reaction solution was cooled to room temperature and concentrated under reduced pressure. The obtained residue was purified by silica gel column chromatography (eluent: system B) to obtain 30 mg of (R)-3-(1-((7-methoxy-2-methyl-6-(4-methylpiperazin-1-yl)quinazolin-4-yl)amino)ethyl)-2-methylbenzonitrile 10, yield 27%.

MS m/z (ESI): 431.3 [M+H]$^+$ $^1$H NMR (400 MHz, DMSO-$d_6$) δ 9.42 (s, 1H), 7.90-7.80 (m, 2H), 7.70 (d, J=7.7 Hz, 1H), 7.43 (t, J=7.8 Hz, 1H), 7.02 (s, 1H), 5.84-5.73 (m, 1H), 3.98 (s, 3H), 3.54-3.42 (m, 3H), 2.84 (d, J=11.8 Hz, 2H), 2.78 (s, 3H), 2.71 (s, 3H), 2.01 (t, J=6.9 Hz, 2H), 1.96-1.88 (m, 2H), 1.63 (d, J=7.0 Hz, 3H), 1.54 (d, J=13.1 Hz, 2H).

Example 11

(R)-3-(1-((6-(4-hydroxy-4-methylpiperidin-1-yl)-7-methoxy-2-methylquinazolin-4-yl)amino)ethyl)-2-methylbenzonitrile

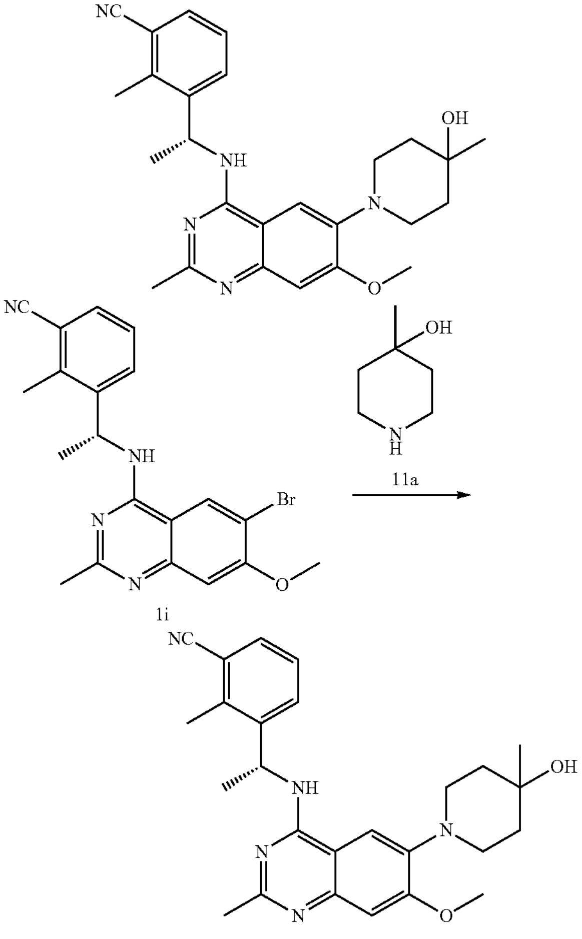

1i

11

(R)-3-(1-((6-bromo-7-methoxy-2-methylquinazolin-4-yl)amino)ethyl)-2-methylbenzonitrile 1i (100 mg, 0.243 mmol), 4-methylpiperidin-4-ol 11a (56.01 mg, 0.486 mmol, commercially available), tris(dibenzylideneacetone)dipalladium (22.25 mg, 0.024 mmol), sodium tert-butoxide (70.10 mg, 0.729 mmol), and 4,5-bisdiphenylphosphine-9,9-dimethylxanthene (30.28 mg, 0.049 mmol) were added sequentially to 1,4-dioxane (5 mL). Under nitrogen atmosphere, the above mixture was heated to 90° C. and stirred continuously for 5 hours. LC-MS showed that the reaction was completed. The reaction solution was cooled to room temperature and concentrated under reduced pressure. The obtained residue was purified by silica gel column chromatography (eluent: system B) to obtain 25 mg of (R)-3-(1-((6-(4-hydroxy-4-methylpiperidin-1-yl)-7-methoxy-2-methylquinazolin-4-yl)amino)ethyl)-2-methylbenzonitrile 11, yield 23%.

MS m/z (ESI): 446.3 $[M+H]^+$ $^1$H NMR (400 MHz, DMSO-$d_6$) δ 8.39 (s, 1H), 7.80 (d, J=7.9 Hz, 1H), 7.70 (s, 1H), 7.63 (d, J=7.6 Hz, 1H), 7.37 (t, J=7.8 Hz, 1H), 6.96 (s, 1H), 5.65 (q, J=7.0 Hz, 1H), 4.29 (s, 1H), 3.87 (s, 3H), 3.11-2.97 (m, 4H), 2.72 (s, 3H), 2.33 (s, 3H), 1.66 (d, J=10.3 Hz, 4H), 1.55 (d, J=7.0 Hz, 3H), 1.21 (s, 3H) ppm.

Example 12

(R)-1-(4-((1-(3-cyano-2-methylphenyl)ethyl)amino)-7-methoxy-2-methylquinazolin-6-yl)azetidine-3-carbonitrile

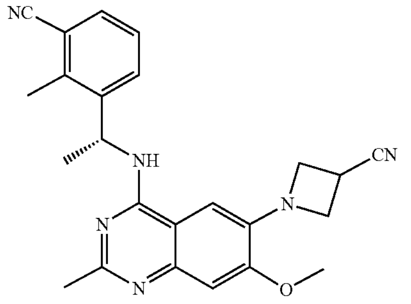

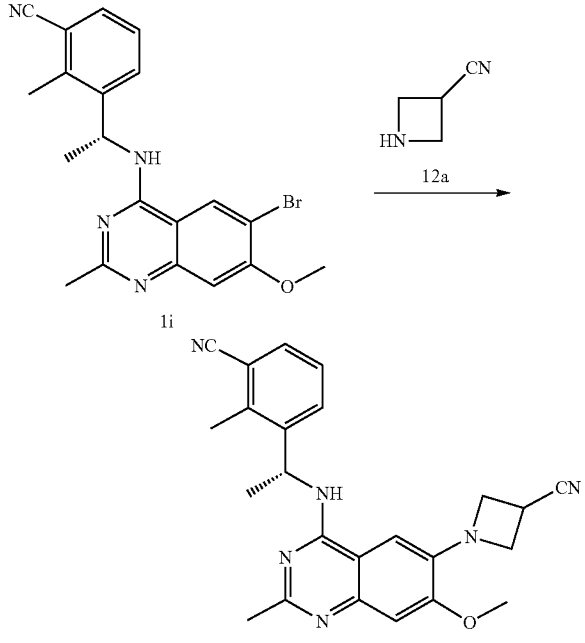

12

(R)-3-(1-((6-bromo-7-methoxy-2-methylquinazolin-4-yl)amino)ethyl)-2-methylbenzonitrile 1i (80 mg, 0.195 mmol), azetidine-3-carbonitrile 12a (41.5 mg, 0.35 mmol, commercially available), tris(dibenzylideneacetone)dipalladium (17.8 mg, 0.019 mmol), sodium tert-butoxide (74.77 mg, 0.778 mmol) and 4,5-bisdiphenylphosphine-9,9-dimethylxanthene (18.54 mg, 0.039 mmol) were added sequentially to 1,4-dioxane (5 mL). Under nitrogen atmosphere, the above mixture was heated to 100° C. and stirred continuously for 6 hours. LC-MS showed that the reaction was completed. The reaction solution was cooled to room temperature, filtered through diatomite, washed with ethyl acetate, and washed three times with water. The organic phase of the reaction solution was dried over anhydrous sodium sulfate, filtered, and concentrated under reduced pressure. The obtained residue was purified by silica gel column chromatography (eluent: system B) to obtain 39 mg of (R)-1-(4-((1-(3-cyano-2-methylphenyl)ethyl)amino)-7-methoxy-2-methylquinazolin-6-yl)azetidine-3-carbonitrile 12, yield 49%.

MS m/z (ESI): 413.2 $[M+H]^+$ $^1$H NMR (400 MHz, DMSO-$d_6$) δ 8.07 (d, J=7.1 Hz, 1H), 7.78 (d, J=7.8 Hz, 1H), 7.62 (d, J=7.6 Hz, 1H), 7.35 (t, J=7.7 Hz, 1H), 7.18 (s, 1H), 6.94 (s, 1H), 5.64 (t, J=7.0 Hz, 1H), 4.23 (q, J=8.4 Hz, 2H), 4.15-3.98 (m, 2H), 3.84 (s, 4H), 2.71 (s, 3H), 2.29 (s, 3H), 1.53 (d, J=7.0 Hz, 3H) ppm.

Example 13

(R)-3-(1-((7-methoxy-2-methyl-6-(4-(methylsulfonyl)piperazin-1-yl)quinazolin-4-yl)amino)ethyl)-2-methylbenzonitrile

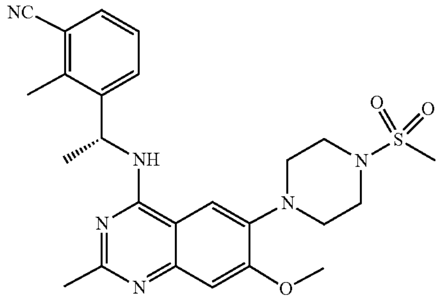

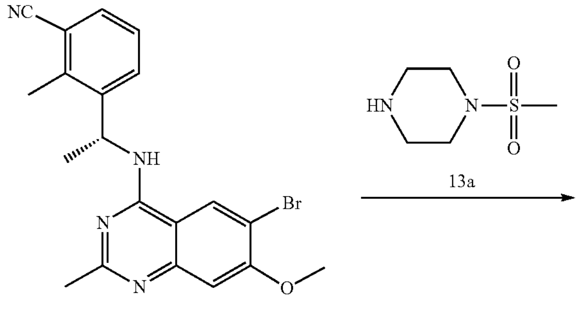

1i

-continued

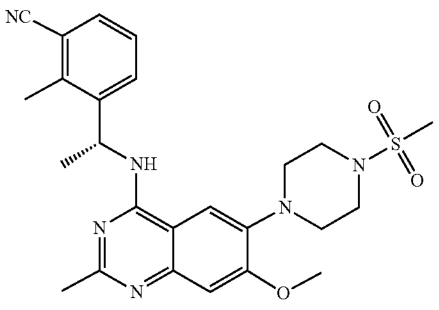

13

(R)-3-(1-((6-bromo-7-methoxy-2-methylquinazolin-4-yl) amino)ethyl)-2-methylbenzonitrile 1i (0.44 mmol, 180 mg), 1-(methylsulfonyl)piperazine 13a (0.66 mmol, 108 mg), tris(dibenzylideneacetone)dipalladium (0.09 mmol, 80 mg), 1,1'-binaphthyl-2,2'-bisdiphenylphosphine (0.18 mmol, 108 mg) and sodium tert-butoxide (1.76 mmol, 168 mg) were added to the microwave tube. 1,4-dioxane (6 mL) was added, and the above mixture reacted under microwave conditions at 125° C. for 1 hour under nitrogen atmosphere. LC-MS showed that the reaction was completed. The reaction solution was cooled to room temperature, filtered through diatomite, and washed with ethyl acetate. The organic phase of the reaction solution was collected, washed three times with water, and once with saturated salt solution, dried over anhydrous sodium sulfate, filtered, and concentrated under reduced pressure. The obtained residue was purified by silica gel column chromatography (eluent: system B) to obtain 37 mg of (R)-3-(1-((7-methoxy-2-methyl-6-(4-(methylsulfonyl)piperazin-1-yl)quinazolin-4-yl) amino)ethyl)-2-methylbenzonitrile 13, yield 17%.

MS m/z (ESI): 495.3 $[M+1]^+$ $^1$H NMR (400 MHz, DMSO-$d_6$) δ 8.23 (s, 1H), 7.82 (d, J=7.9 Hz, 1H), 7.73 (d, J=3.5 Hz, 1H), 7.64 (d, J=7.7 Hz, 1H), 7.38 (t, J=7.8 Hz, 1H), 7.04 (s, 1H), 5.67 (q, J=7.0 Hz, 1H), 3.90 (s, 3H), 3.19 (s, 6H), 2.98 (s, 3H), 2.74 (s, 3H), 2.33 (s, 3H), 1.56 (d, J=7.0 Hz, 3H) ppm.

Example 14

(R)-3-(1-((7-methoxy-2-methyl-6-(4-oxido-1,4-oxaphosphinan-4-yl)quinazolin-4-yl)amino)ethyl)-2-methylbenzonitrile

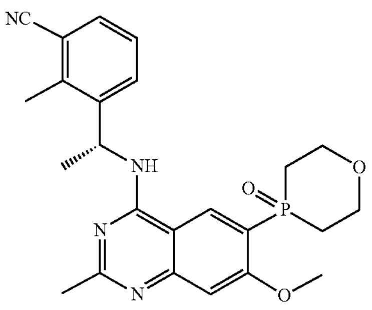

-continued

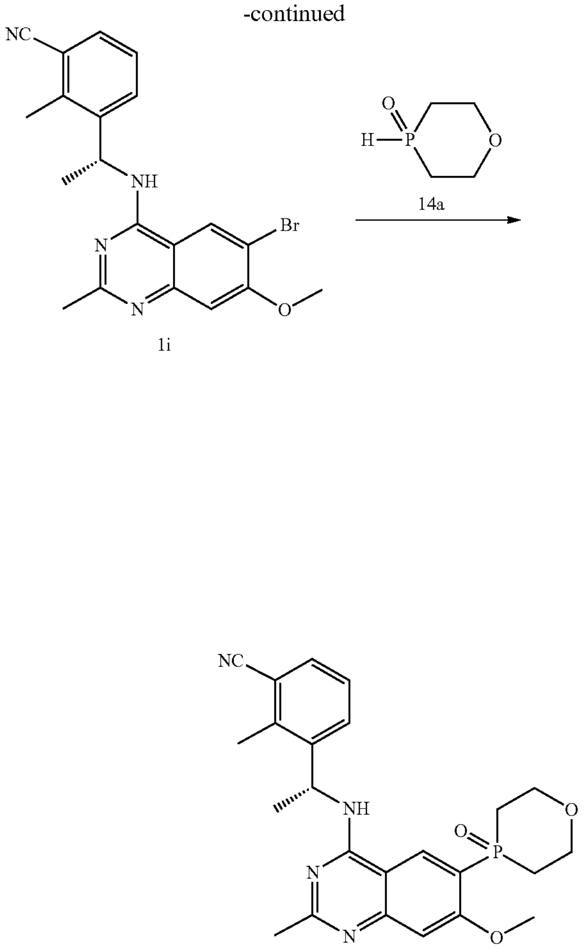

1i

14

(R)-3-(1-((6-bromo-7-methoxy-2-methylquinazolin-4-yl) amino)ethyl)-2-methylbenzonitrile 1i (150.0 mg, 0.36 mmol), 1,4-oxaphosphinane 4-oxide 14a (87.6 mg, 0.73 mmol), $Pd_2(dba)_3$ (33.4 mg, 0.036 mmol), XantPhos (42.20 mg, 0.073 mmol), triethylamine (110.7 mg, 1.1 mmol) and 1,4-dioxane (6 mL) were added to a 25 mL flask. Under nitrogen atmosphere, the above mixture reacted at 110 degrees for 6 hours. LC-MS showed that the reaction was completed. The reaction solution was cooled to room temperature, filtered through diatomite, and washed with ethyl acetate. The organic phase of the reaction solution was collected, washed three times with water, and once with saturated salt solution, dried over anhydrous sodium sulfate, filtered, and concentrated under reduced pressure. The obtained residue was purified by silica gel column chromatography (eluent: system B) to obtain 25 mg of (R)-3-(1-((7-methoxy-2-methyl-6-(4-oxido-1,4-oxaphosphinan-4-yl) quinazolin-4-yl)amino)ethyl)-2-methylbenzonitrile 14, yield 16%.

MS m/z (ESI): 451.2$[M+1]^+$ $^1$H NMR (400 MHz, DMSO-$d_6$) δ 8.93 (s, 1H), 8.74 (d, J=13.8 Hz, 1H), 7.84 (d, J=7.9 Hz, 1H), 7.62 (d, J=7.6 Hz, 1H), 7.35 (t, J=7.8 Hz, 1H), 7.12 (d, J=4.7 Hz, 1H), 5.65 (q, J=7.1 Hz, 1H), 4.13-3.98 (m, 4H), 3.95 (s, 3H), 2.71 (s, 3H), 2.56-2.51 (m, 2H), 2.35 (s, 3H), 1.97-1.83 (m, 2H), 1.54 (d, J=7.0 Hz, 3H) ppm.

Example 15

(R)-3-(1-((7-methoxy-2-methyl-6-(4-(4-methylpiperazin-1-yl)piperidin-1-yl) quinazolin-4-yl)amino) ethyl)-2-methylbenzonitrile

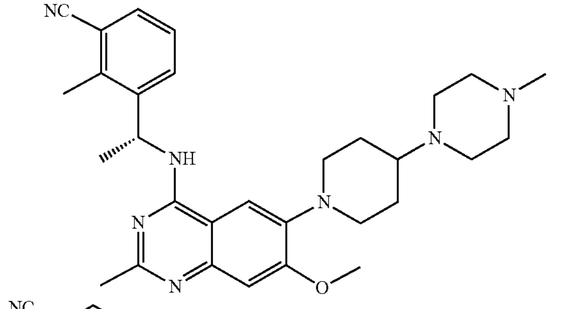

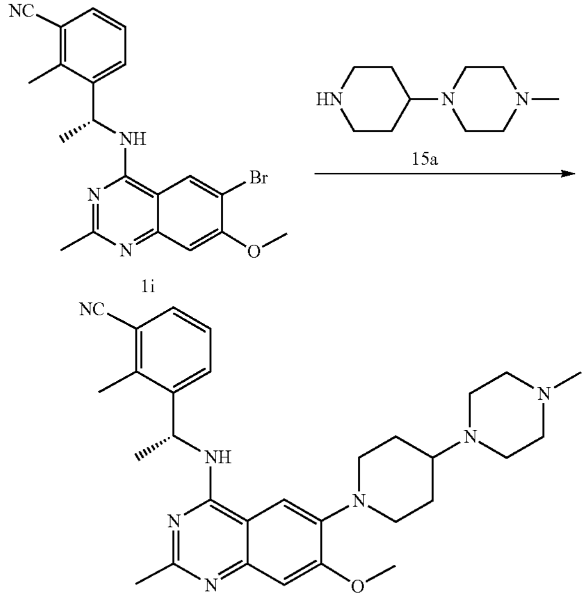

1i

15

(R)-3-(1-((6-bromo-7-methoxy-2-methylquinazolin-4-yl) amino)ethyl)-2-methylbenzonitrile 1i (100 mg, 0.24 mmol), 1-methyl-4-(piperidin-4-yl)piperazine 15a (89.1 mg, 0.48 mmol), $Pd_2(dba)_3$ (44.5 mg, 0.048 mmol), BINAP (60.6 mg, 0.096 mmol) and 1,4-dioxane (6 mL) were added to a 25 mL microwave tube. Under nitrogen atmosphere, the above mixture reacted under microwave conditions at 125° C. for 1 hour. LC-MS showed that the reaction was completed. The reaction solution was cooled to room temperature, filtered through diatomite, and washed with ethyl acetate. The organic phase of the reaction solution was collected, washed three times with water, and once with saturated salt solution, dried over anhydrous sodium sulfate, filtered, and concentrated under reduced pressure. The obtained residue was purified by silica gel column chromatography (eluent: system B) to obtain 45 mg of (R)-3-(1-((7-methoxy-2-methyl-6-(4-(4-methylpiperazin-1-yl)piperidin-1-yl)quinazolin-4-yl)amino)ethyl)-2-methylbenzonitrile 15, yield 35%.

$^1H$ NMR (400 MHz, DMSO-$d_6$) δ 8.20 (s, 1H), 7.80 (d, J=7.9, 1H), 7.62 (s, 1H), 7.61 (d, J=6.2 Hz, 1H), 7.35 (t, J=7.7 Hz, 1H), 6.97 (s, 1H), 5.64 (p, J=7.0 Hz, 1H), 3.87 (s, 2H), 3.61-3.44 (m, 2H), 2.71 (s, 3H), 2.68-2.54 (m, 5H), 2.39-2.36 (m, 4H), 2.30 (s, 3H), 2.19 (s, 3H), 1.92-1.78 (m, 2H), 1.65-1.59 (m, 2H), 1.53 (d, J=7.0 Hz, 3H) ppm.

MS m/z (ESI): 514.4 $[M+1]^+$

Example 16

(R)-3-(1-((7-methoxy-2-methyl-6-(2-(methylsulfonyl)-2,7-diazaspiro[3.5]nonan-7-yl)quinazolin-4-yl) amino)ethyl)-2-methylbenzonitrile

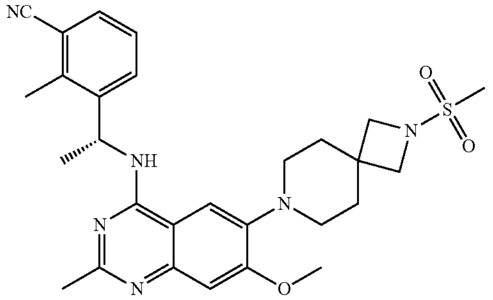

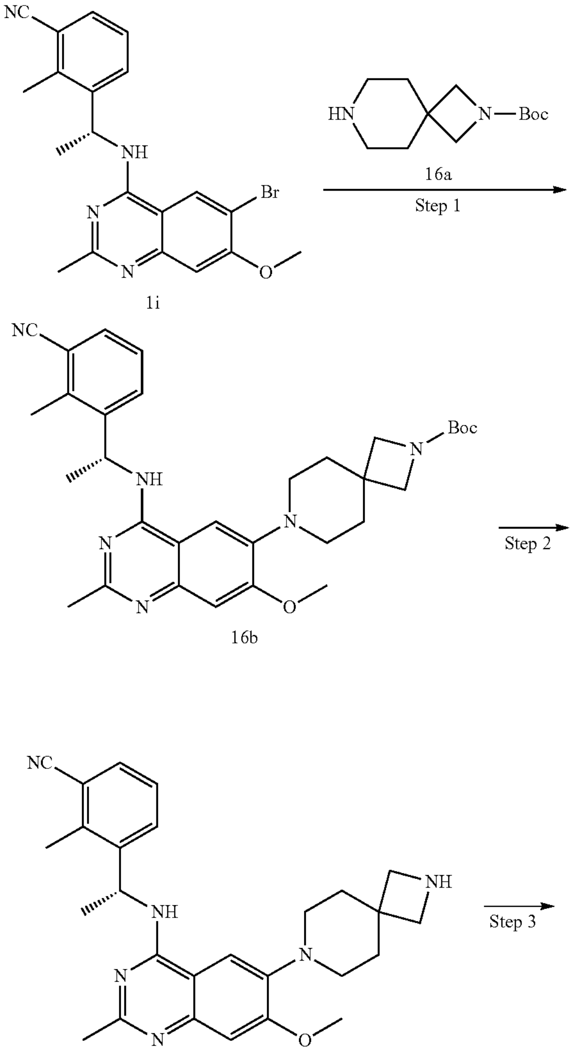

1i

16b

16c

-continued

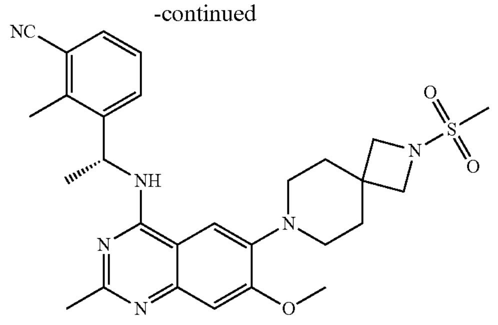

16

Step 1

Synthesis of tert-butyl (R)-7-(4-((1-(3-cyano-2-methylphenyl)ethyl)amino)-7-methoxy-2-methylquinazolin-6-yl)-2,7-diazaspiro[3.5]nonane-2-carboxylate (R)-3-(1-((6-bromo-7-methoxy-2-methylquinazolin-4-yl)amino)ethyl)-2-methylbenzonitrile 1i (411 mg, 1 mmol), tert-butyl 2,7-diazaspiro[3.5]nonane-2-carboxylate 16a (347 mg, 1.5 mmol), tris(dibenzylideneacetone)dipalladium (84 mg, 0.1 mmol), 1,1'-binaphthyl-2,2'-bisdiphenylphosphine (127 mg, 0.2 mmol) and sodium tert-butoxide (294 mg, 3 mmol) were added to a microwave tube. 1,4-dioxane (15 mL) was added, and the above mixture reacted under microwave conditions at 125° C. for 1 hour under nitrogen atmosphere. LC-MS showed that the reaction was completed. The reaction solution was cooled to room temperature, filtered through diatomite, and washed with ethyl acetate. The organic phase of the reaction solution was collected, washed three times with water, and once with saturated salt solution, dried over anhydrous sodium sulfate, filtered, and concentrated under reduced pressure. The obtained residue was purified by silica gel column chromatography (eluent: system B) to obtain 391 mg of tert-butyl (R)-7-(4-((1-(3-cyano-2-methylphenyl)ethyl)amino)-7-methoxy-2-methylquinazolin-6-yl)-2,7-diazaspiro[3.5]nonane-2-carboxylate 16b, yield 69%.

MS m/z (ESI): 557.4[M+1]$^+$

Step 2

(R)-3-(1-((7-methoxy-2-methyl-6-(2,7-diazaspiro[3.5]nonan-7-yl)quinazolin-4-yl)amino)ethyl)-2-methylbenzonitrile tert-butyl (R)-7-(4-((1-(3-cyano-2-methylphenyl)ethyl)amino)-7-methoxy-2-methylquinazolin-6-yl)-2,7-diazaspiro[3.5]nonane-2-carboxylate 16b (390 mg, 0.7 mmol) was added to a 25 mL round-bottom flask, 1,4-dioxane (10 mL) was added, 4M hydrogen chloride/dioxane solution (2 mL) was added, and the above mixture was stirred at room temperature for 3 hours. LC-MS showed that the reaction was completed. Ethyl acetate and water were added to the reaction solution, and the pH of the aqueous phase of the reaction solution was adjusted to basic with anhydrous sodium carbonate, and liquid separation was conducted. The organic phase of the reaction solution was washed twice with water, dried over anhydrous sodium sulfate, and the solvent was removed under reduced pressure to obtain 248 mg of (R)-3-(1-((7-methoxy-2-methyl-6-(2,7-diazaspiro[3.5]nonan-7-yl)quinazolin-4-yl)amino)ethyl)-2-methylbenzonitrile 16c crude product, yield 78%.

MS m/z (ESI): 457.3[M+1]$^+$

Step 3

(R)-3-(1-((7-methoxy-2-methyl-6-(2-(methylsulfonyl)-2,7-diazaspiro[3.5]nonan-7-yl)quinazolin-4-yl)amino)ethyl)-2-methylbenzonitrile (R)-3-(1-((7-methoxy-2-methyl-6-(2,7-diazaspiro[3.5]nonan-7-yl)quinazolin-4-yl)amino)ethyl)-2-methylbenzonitrile 16c (47 mg, 0.1 mmol) was added to a 10 mL round-bottom flask, dichloromethane (3 mL), triethylamine (0.2 mL), and methanesulfonyl chloride (25 mg, 0.2 mmol) were added, and the above mixture was stirred at room temperature for 2 hours. LC-MS showed that the reaction was completed. Dichloromethane was added to the reaction solution, and the reaction solution was washed three times with water and once with saturated salt solution. The organic phase of the reaction solution was dried over anhydrous sodium sulfate. The obtained residue was purified by silica gel column chromatography (eluent: system B) to obtain 37 mg of (R)-3-(1-((7-methoxy-2-methyl-6-(2-(methylsulfonyl)-2,7-diazaspiro[3.5]nonan-7-yl)quinazolin-4-yl)amino)ethyl)-2-methylbenzonitrile 16, yield 64%.

MS m/z (ESI): 535.3[M+1]$^+$ $^1$H NMR (400 MHz, DMSO-$d_6$) δ 8.35 (s, 1H), 7.82 (d, J=7.9 Hz, 1H), 7.65 (s, 1H), 7.64 (d, J=8.1 Hz, 1H), 7.38 (t, J=7.8 Hz, 1H), 7.00 (s, 1H), 5.67 (t, J=7.1 Hz, 1H), 3.90 (s, 3H), 3.70 (s, 4H), 3.05 (s, 3H), 3.00 (s, 4H), 2.73 (s, 3H), 2.33 (s, 3H), 1.92 (s, 4H), 1.56 (d, J=7.0 Hz, 3H) ppm.

Example 17

(R)-3-(1-((7-methoxy-6-(4-methoxypiperidin-1-yl)-2-methylquinazolin-4-yl) amino)ethyl)-2-methylbenzonitrile

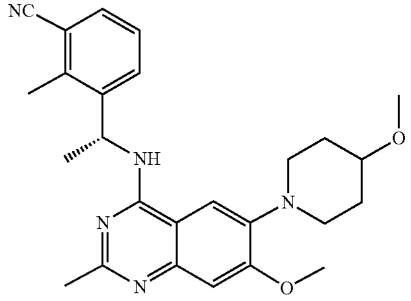

1i

17a

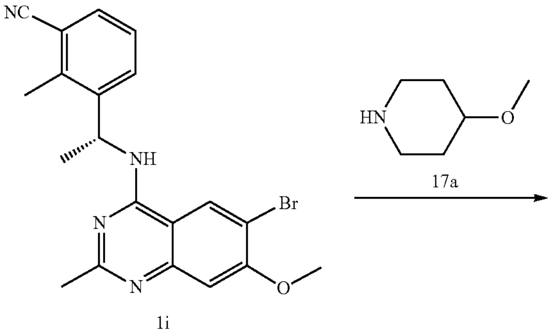

-continued

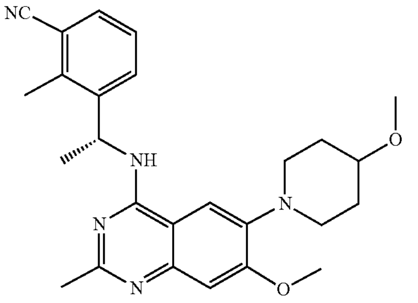

17

(R)-3-(1-((6-bromo-7-methoxy-2-methylquinazolin-4-yl)amino)ethyl)-2-methylbenzonitrile 1i (120 mg, 0.29 mmol), 4-methoxypiperidine 17a (67.2 mg, 0.58 mmol), $Pd_2(dba)_3$ (53.4 mg, 0.058 mmol), BINAP (72.7 mg, 0.12 mmol) were added to a microwave tube. 1,4-dioxane (3 mL) was added, and the above mixture was stirred under microwave conditions at 125° C. for 1 hour under nitrogen atmosphere. LC-MS showed the reaction was completed. The reaction solution was cooled to room temperature, filtered through diatomite, washed with ethyl acetate. The organic phase of the reaction solution was collected, washed three times with water and once with saturated salt solution, dried over anhydrous sodium sulfate, filtered, and concentrated under reduced pressure. The obtained residue was purified by silica gel column chromatography (eluent: system B) to obtain 32.1 mg of (R)-3-(1-((7-methoxy-6-(4-methoxypiperidin-1-yl)-2-methylquinazolin-4-yl)amino)ethyl)-2-methylbenzonitrile 17, yield 25%.

MS m/z (ESI): 446.3[M+1]$^+$ $^1$H NMR (400 MHz, DMSO-$d_6$) δ 8.38 (s, 1H), 7.83 (d, J=7.9 Hz, 1H), 7.70 (s, 1H), 7.64 (d, J=7.7 Hz, 1H), 7.38 (t, J=7.8 Hz, 1H), 7.00 (s, 1H), 5.68 (t, J=7.2 Hz, 1H), 3.90 (s, 3H), 3.41-3.31 (m, 3H), 3.32 (s, 3H), 2.89-2.81 (m, 2H), 2.73 (s, 3H), 2.34 (s, 3H), 2.02-1.97 (m, 2H), 1.69-1.65 (m, 2H), 1.56 (d, J=6.9 Hz, 3H) ppm.

Example 18

(R)-3-(1-((6-(9-acetyl-3,9-diazaspiro[5.5]undecan-3-yl)-7-methoxy-2-methylquinazolin-4-yl)amino)ethyl)-2-methylbenzonitrile

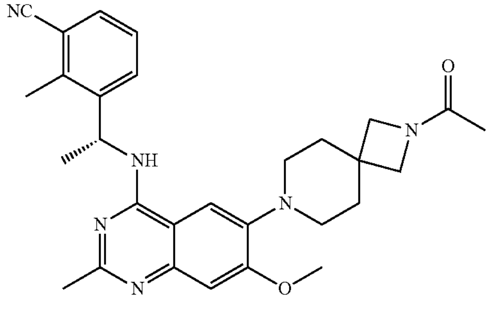

-continued

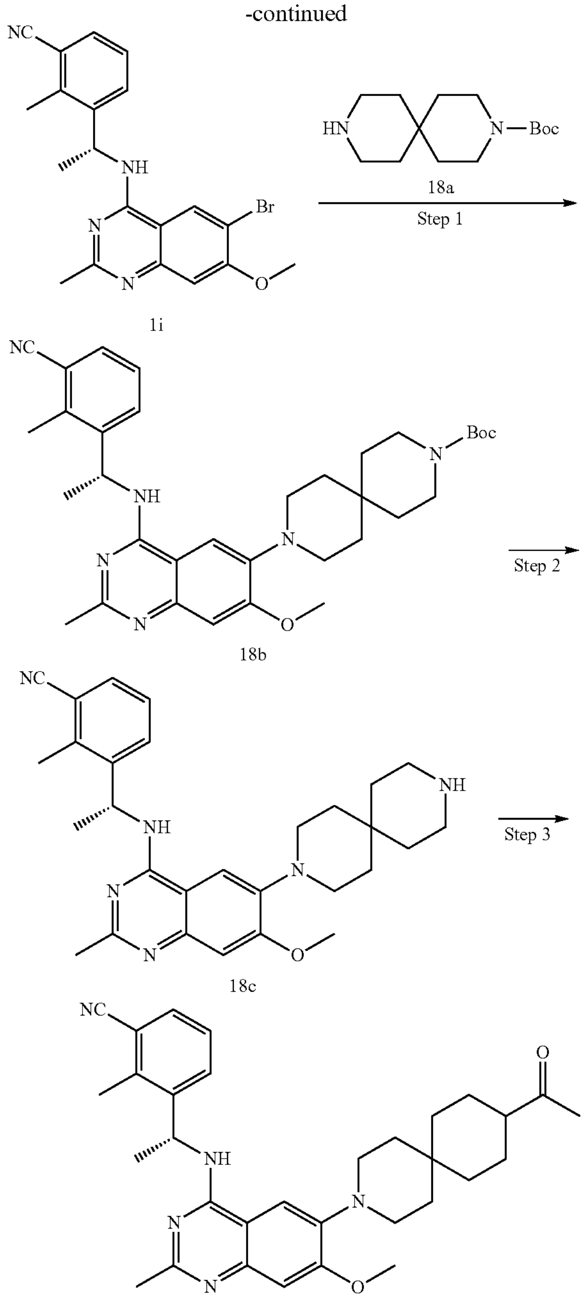

1i 18a 18b 18c 18

Step 1

Tert-butyl (R)-9-(4-((1-(3-cyano-2-methylphenyl)ethyl)amino)-7-methoxy-2-methylquinazolin-6-yl)-3,9-diazaspiro[5.5]undecane-3-carboxylate (R)-3-(1-((6-bromo-7-methoxy-2-methylquinazolin-4-yl)amino)ethyl)-2-methylbenzonitrile 1i (250 mg, 0.608 mmol), tert-butyl 3,9-diazaspiro[5.5]undecane-3-carboxylate 18a (231.9 mg, 0.912 mmol, commercially available), $Pd_2(dba)_3$ (111.3 mg, 0.122 mmol), BINAP (151.4 mg, 0.243 mmol), sodium tert-butoxide (175.2 mg, 1.82 mmol) were added to a microwave tube. 1,4-dioxane (10 mL) was added, and the above mixture was stirred under microwave conditions at 125° C. for 1 hour under nitrogen atmosphere. LC-MS showed that the reaction was completed. The reaction solution was cooled to room temperature, filtered through diatomite, washed with ethyl acetate. The organic phase of the reaction solution was collected, washed three times with water and once with saturated salt solution, dried over anhydrous sodium sulfate, filtered, and concentrated under reduced pressure. The obtained residue was purified by silica gel column chromatography (eluent: system B) to obtain 203 mg of tert-butyl (R)-9-(4-((1-(3-cyano-2-methylphenyl)ethyl)amino)-7-methoxy-2-methylquinazolin-6-yl)-3,9-diazaspiro[5.5]undecane-3-carboxylate 18b, yield 58%

MS m/z (ESI): 585.4[M+1]$^+$

Step 2

(R)-3-(1-((7-methoxy-2-methyl-6-(3,9-diazaspiro[5.5]undecan-3-yl)quinazolin-4-yl)amino)ethyl)-2-methylbenzonitrile tert-butyl (R)-9-(4-((1-(3-cyano-2-methylphenyl)ethyl)amino)-7-methoxy-2-methylquinazolin-6-yl)-3,9-diazaspiro[5.5]undecane-3-carboxylate 18b (203 mg, 0.347 mmol) was added to a round-bottom flask, 1,4-dioxane (6 mL) was added, 4 M hydrogen chloride-1,4-dioxane solution (3 mL) was added, and the above mixture reacted at room temperature for 2 hours. LC-MS showed that the reaction was completed. The reaction solution was removed by rotary evaporation, dichloromethane and water were added, saturated sodium carbonate solution was added to adjust the pH of the aqueous phase to basic, and dichloromethane/methanol mixed solvent (10:1) was added for extraction. The organic phase of the reaction solution was collected, dried over anhydrous sodium sulfate, filtered, and the solvent was removed under reduced pressure to obtain 147 mg of (R)-3-(1-((7-methoxy-2-methyl-6-(3,9-diazaspiro[5.5]undecan-3-yl)quinazolin-4-yl)amino)ethyl)-2-methylbenzonitrile 18c, the above product was directly used in the next reaction.

MS m/z (ESI): 485.4[M+1]$^+$

Step 3

(R)-3-(1-((6-(9-acetyl-3,9-diazaspiro[5.5]undecan-3-yl)-7-methoxy-2-meth ylquinazolin-4-yl)amino)ethyl)-2-methylbenzonitrile (R)-3-(1-((7-methoxy-2-methyl-6-(3,9-diazaspiro[5.5]undecan-3-yl)quinazolin-4-yl)amino)ethyl)-2-methylbenzonitrile 18c (147 mg, 0.303 mmol) was added to a round-bottom flask, dichloromethane (5 mL), triethylamine (0.2 mL), and acetyl chloride (35.7 mg, 0.455 mmol) were added, and the above mixture reacted at room temperature for 2 hours. LC-MS showed that the reaction was completed. Dichloromethane was added to the reaction solution, and the reaction solution was washed three times with water and once with saturated salt solution. The organic phase of the reaction solution was dried over anhydrous sodium sulfate, filtered, and concentrated under reduced pressure. The obtained residue was purified by silica gel column chromatography (eluent: system B) to obtain 54.4 mg of (R)-3-(1-((6-(9-acetyl-3,9-diazaspiro[5.5]undecan-3-yl)-7-methoxy-2-methylquinazolin-4-yl)amino)ethyl)-2-methylbenzonitrile 18, yield 33%.

MS m/z (ESI): 527.3 [M+1]$^+$ $^1$H NMR (400 MHz, DMSO-$d_6$) δ 8.21 (d, J=7.0 Hz, 1H), 7.82 (d, J=7.9 Hz, 1H), 7.67 (s, 1H), 7.63 (d, J=7.7 Hz, 1H), 7.37 (t, J=7.8 Hz, 1H), 6.98 (s, 1H), 5.67 (t, J=7.0 Hz, 1H), 3.88 (s, 3H), 3.50-3.40 (m, 4H), 3.07-3.02 (m, 4H), 2.73 (s, 3H), 2.32 (s, 3H), 2.01 (s, 3H), 1.69-1.65 (m, 4H), 1.55 (d, J=7.1 Hz, 3H), 1.54-1.51 (m, 2H), 1.48-1.44 (m, 2H) ppm.

Example 19

(R)-3-(1-((6-(2-acetyl-2,7-diazaspiro[3.5]nonan-7-yl)-7-methoxy-2-methylquinazolin-4-yl)amino)ethyl)-2-methylbenzonitrile

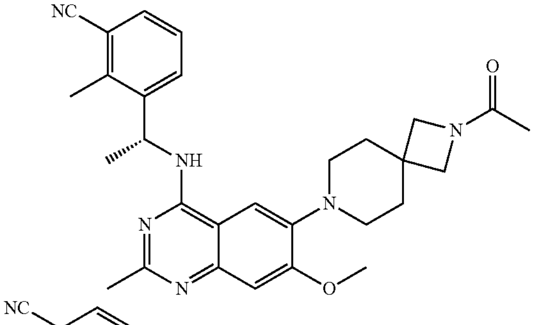

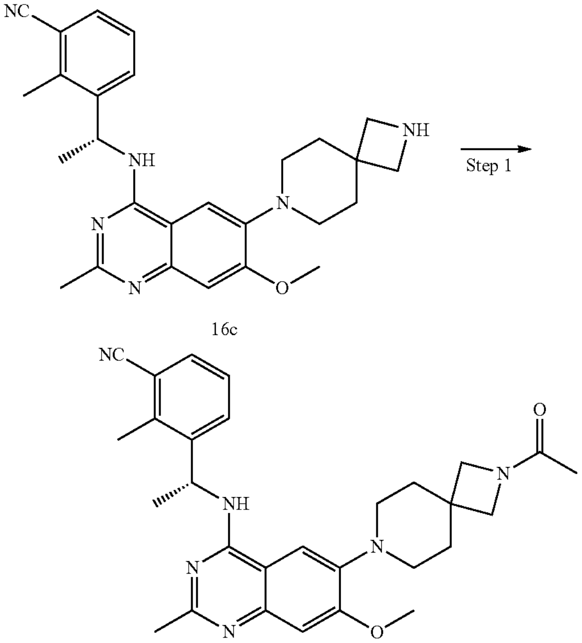

19

(R)-3-(1-((7-methoxy-2-methyl-6-(2,7-diazaspiro[3.5]nonan-7-yl)quinazolin-4-yl)amino)ethyl)-2-methylbenzonitrile 16c (135 mg, 0.296 mmol) was added to a round-bottom flask, dichloromethane (10 mL), triethylamine (0.3 mL), acetic anhydride (90.6 mg, 0.887 mmol), 4-dimethylaminopyridine (7.2 mg, 0.059 mmol) were added, the above mixture reacted at room temperature overnight. LC-MS showed the reaction was completed. Dichloromethane was added to the reaction solution, and the reaction solution was washed three times with water and once with saturated salt solution. The organic phase of the reaction solution was dried over anhydrous sodium sulfate, filtered, and concentrated under reduced pressure. The obtained residue was purified by silica gel column chromatography (eluent: system B) to obtain 34.2 mg of (R)-3-(1-((6-(2-acetyl-2,7-diazaspiro[3.5]nonan-7-yl)-7-methoxy-2-methylquinazolin-4-yl)amino)ethyl)-2-methylbenzonitrile 19, yield 21%.

MS m/z (ESI): 499.4 [M+1]$^+$ $^1$H NMR (400 MHz, DMSO-$d_6$) δ 8.42 (s, 1H), 7.80 (d, J=8.0 Hz, 1H), 7.66 (s, 1H), 7.63 (d, J=7.7 Hz, 1H), 7.37 (t,

J=7.8 Hz, 1H), 6.99 (s, 1H), 5.67 (t, J=7.0 Hz, 1H), 3.89 (s, 3H), 3.87 (s, 2H), 3.61 (s, 2H), 2.99 (s, 4H), 2.71 (s, 3H), 2.33 (s, 3H), 1.89-1.86 (m, 4H), 1.78 (s, 3H), 1.55 (d, J=7.0 Hz, 3H) ppm.

Example 20

(R)-3-(1-((6-(4-(2-hydroxyethyl)piperazin-1-yl)-7-methoxy-2-methylquinazolin-4-yl)amino)ethyl)-2-methylbenzonitrile

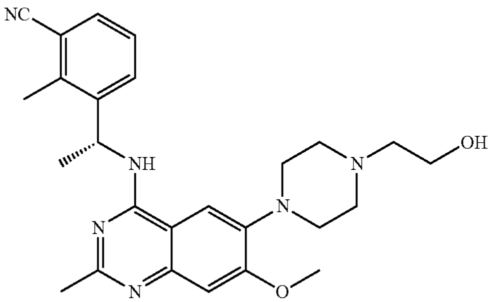

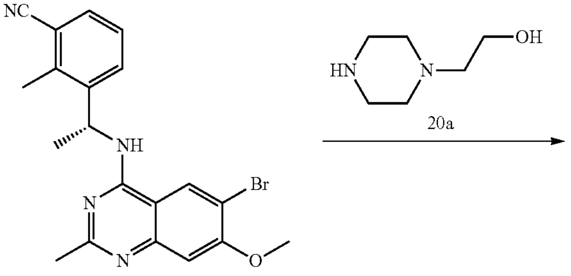

1i

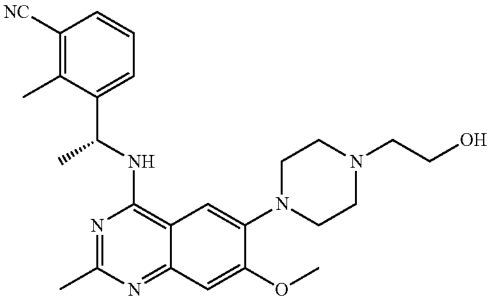

20

(R)-3-(1-((6-bromo-7-methoxy-2-methylquinazolin-4-yl)amino)ethyl)-2-methylbenzonitrile 1i (100 mg, 0.243 mmol), 2-(piperazin-1-yl)ethan-1-ol 20a (57.0 mg, 0.438 mmol), $Pd_2(dba)_3$ (22.3 mg, 0.024 mmol), BINAP (30.3 mg, 0.049 mmol), sodium tert-butoxide (70.1 mg, 0.729 mmol) and 1,4-dioxane (5 mL) were added to a reaction flask, nitrogen was replaced, and the above mixture reacted at 100 degrees for 6 hours. LC-MS showed that the reaction was completed. The reaction solution was cooled to room temperature, filtered through diatomite, and washed with ethyl acetate. The organic phase of the reaction solution was collected, washed three times with water, and once with saturated salt solution, dried over anhydrous sodium sulfate, filtered, and concentrated under reduced pressure. The obtained residue was purified by silica gel column chromatography (eluent: system B) to obtain 16 mg of (R)-3-(1-((6-(4-(2-hydroxyethyl)piperazin-1-yl)-7-methoxy-2-methylquinazolin-4-yl)amino)ethyl)-2-methylbenzonitrile 20, yield 14%.

MS m/z (ESI): 461.3 [M+1]$^+$ $^1$H NMR (400 MHz, DMSO-$d_6$) δ 8.20 (d, J=7.2 Hz, 1H), 7.80 (d, J=7.9 Hz, 1H), 7.63 (s, 1H), 7.62 (d, J=8.5 Hz, 1H), 7.35 (t, J=7.8 Hz, 1H), 6.98 (s, 1H), 5.65 (q, J=7.0 Hz, 1H), 3.87 (s, 3H), 3.57 (t, J=6.3 Hz, 2H), 3.09 (s, 4H), 2.72 (s, 3H), 2.66 (s, 4H), 2.54-2.50 (m, 2H), 2.30 (s, 3H), 1.54 (d, J=7.0 Hz, 3H) ppm.

Example 21

(R)-3-(1-((7-methoxy-2-methyl-6-(4-(2-oxopyrrolidin-1-yl)piperidin-1-yl)quinazolin-4-yl)amino)ethyl)-2-methyl benzonitrile

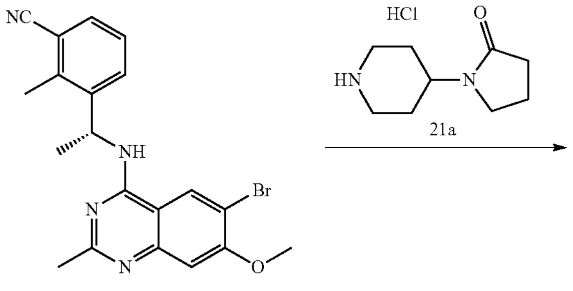

1i

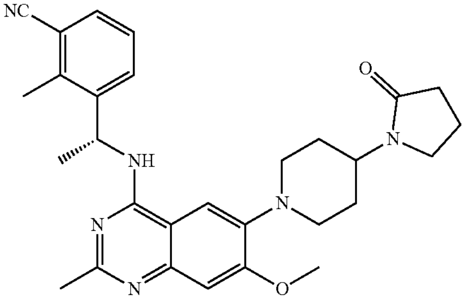

21

(R)-3-(1-((6-bromo-7-methoxy-2-methylquinazolin-4-yl)amino)ethyl)-2-methylbenzonitrile 1i (150.0 mg, 0.365 mmol), 1-(piperidin-4-yl)pyrrolin-2-one hydrochloride 21a (149.3 mg, 0.73 mmol), sodium tert-butoxide (140.2 mg, 1.46 mmol), 1,4-dioxane (6 mL), $Pd_2(dba)_3$ (66.8 mg, 0.073 μmol), BINAP (45.4 mg, 0.073 mmol) were added to a 10 mL microwave reaction tube, the above mixture reacted at 130 degrees for 1 hour under nitrogen atmosphere. LC-MS showed that the reaction was completed. The reaction solution was cooled to room temperature, filtered through diatomite, and washed with ethyl acetate. The organic phase of the reaction solution was collected, washed three times with water, and once with saturated salt solution, dried over anhydrous sodium sulfate, filtered, and concentrated under reduced pressure. The obtained residue was purified by silica gel column chromatography (eluent: System B) to obtain 45 mg of (R)-3-(1-((7-methoxy-2-methyl-6-(4-(2-oxopyrrolidin-1-yl)piperidin-1-yl)quinazolin-4-yl)amino)ethyl)-2-methylbenzonitrile 21, yield 24%.

MS m/z (ESI): 499.4 [M+1]$^+$ $^1$H NMR (400 MHz, DMSO-$d_6$) δ 8.20 (d, J=7.1 Hz, 1H), 7.80 (d, J=7.9 Hz, 1H), 7.66 (s, 1H), 7.62 (d, J=7.6 Hz, 1H), 7.36 (t, J=7.8 Hz, 1H), 6.98 (s, 1H), 5.64 (p, J=7.0 Hz, 1H), 3.96-3.90 (m, 1H), 3.88 (s, 3H), 3.54 (d, J=11.5 Hz, 2H), 3.38 (t, J=6.9 Hz, 2H), 2.74-2.68 (m, 2H), 2.72 (s, 3H), 2.30 (s, 3H), 2.25 (t, J=8.1 Hz, 2H), 1.96-1.82 (m, 4H), 1.69-1.65 (m, 2H), 1.54 (d, J=7.0 Hz, 3H) ppm.

Example 22

(R)-1-(4-((1-(3-cyano-2-methylphenyl)ethyl)amino)-7-methoxy-2-methylquinazolin-6-yl)-N,N-dimethylpiperidine-4-carboxamide

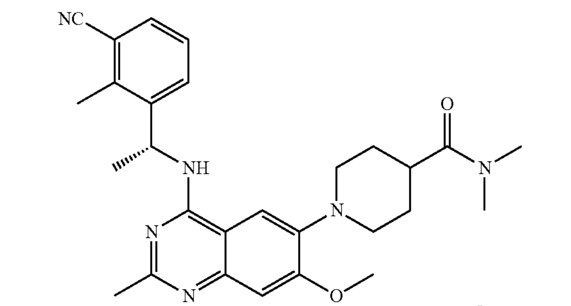

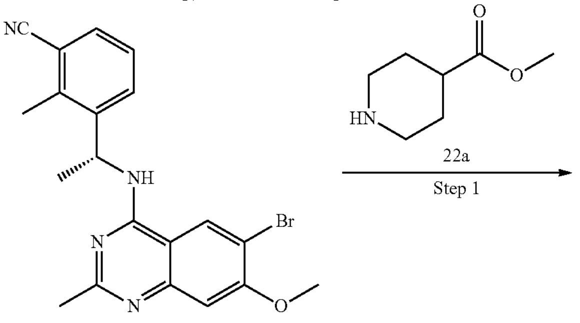

1i

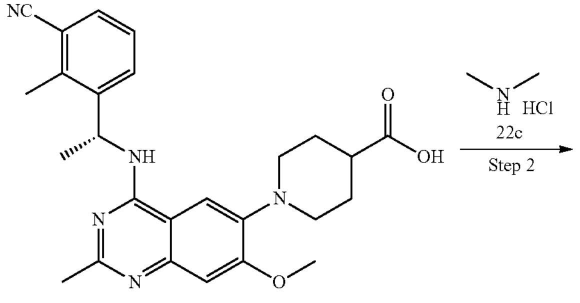

22b

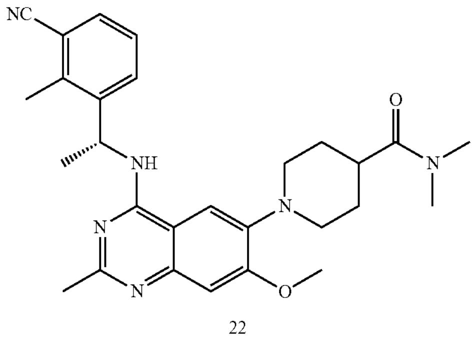

22

Step 1

(R)-1-(4-((1-(3-cyano-2-methylphenyl)ethyl)amino)-7-methoxy-2-methylquinazolin-6-yl)piperidine-4-carboxylic acid (R)-3-(1-((6-bromo-7-methoxy-2-methylquinazolin-4-yl)amino)ethyl)-2-methylbenzonitrile 1i (400 mg, 0.97 mmol), methyl piperidine-4-carboxylate 22a (280.0 mg, 1.96 mmol), $Pd_2(dba)_3$ (178.0 mg, 0.195 mmol), BINAP (242 mg, 0.389 mmol), sodium tert-butoxide (841.2 mg, 8.75 mmol) and 1,4-dioxane (10 mL) were added to a reaction flask, nitrogen was replaced, and the above mixture reacted at 100 degrees for 5 hours. LC-MS showed that the reaction was completed. The reaction solution was cooled to room temperature, filtered through diatomite, and washed with ethyl acetate. The organic phase of the reaction solution was collected and extracted with water. The aqueous phase of the reaction solution was collected, washed once with ethyl acetate, the pH of the aqueous phase was adjusted to weak acidity, and extracted three times with ethyl acetate. The organic phases were combined, dried over anhydrous sodium sulfate, and concentrated to obtain 375 mg of (R)-1-(4-((1-(3-cyano-2-methylphenyl)ethyl)amino)-7-methoxy-2-methylquinazolin-6-yl)piperidine-4-carboxylic acid 22b, yield 84%.

MS m/z (ESI): 460.3 $[M+1]^+$

Step 2

(R)-1-(4-((1-(3-cyano-2-methylphenyl)ethyl)amino)-7-methoxy-2-methylquinazolin-6-yl)-N,N-dimethylpiperidine-4-carboxamide (R)-1-(4-((1-(3-cyano-2-methylphenyl)ethyl)amino)-7-methoxy-2-methylquinazolin-6-yl)piperidine-4-carboxylic acid 22b (119 mg, 0.26 mmol) was added to a 25 ml flask, dimethylamine hydrochloride (27.7 mg, 0.34 mmol), HATU (148.9 mg, 0.39 mmol), DMF (2 mL), and triethylamine (79.3 mg, 0.78 mmol) were added, and the above mixture reacted at room temperature for 2 hours. LC-MS showed that the reaction was completed. The reaction solution was cooled to room temperature, washed with ethyl acetate, washed with water for three times, and once with saturated salt solution. The organic phase of the reaction solution was dried over anhydrous sodium sulfate, filtered, and concentrated under reduced pressure. The obtained residue was purified by silica gel column chromatography (eluent: system B) to obtain 13 mg of (R)-1-(4-((1-(3-cyano-2-methylphenyl)ethyl)amino)-7-methoxy-2-methylquinazolin-6-yl)-N,N-dimethylpiperidine-4-carboxamide 22, yield 11%.

$^1H$ NMR (400 MHz, DMSO-$d_6$) δ 8.20 (d, J=7.0 Hz, 1H), 7.79 (d, J=7.9 Hz, 1H), 7.63 (s, 1H), 7.62 (d, J=8.8 Hz, 1H), 7.36 (t, J=7.7 Hz, 1H), 6.97 (s, 1H), 5.65 (t, J=7.1 Hz, 1H), 3.87 (s, 3H), 3.50-3.46 (m, 2H), 3.06 (s, 3H), 2.84 (s, 3H), 2.80-2.75 (m, 1H), 2.72 (s, 3H), 2.30 (s, 3H), 1.78-1.74 (m, 4H), 1.54 (d, J=7.0 Hz, 3H) ppm.

MS m/z (ESI): 487.3 $[M+1]^+$

Example 23

(R)-3-(1-((7-methoxy-2-methyl-6-(4-(4-(methylsulfonyl)piperazin-1-yl)piperidin-1-yl)quinazolin-4-yl)amino)ethyl)-2-methylbenzonitrile

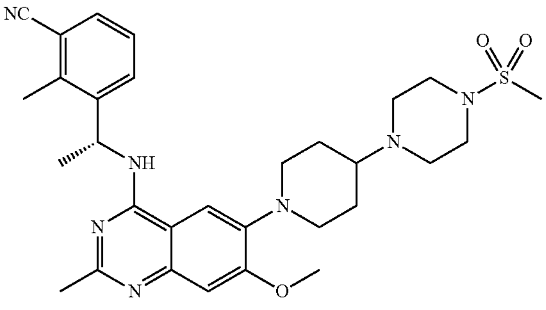

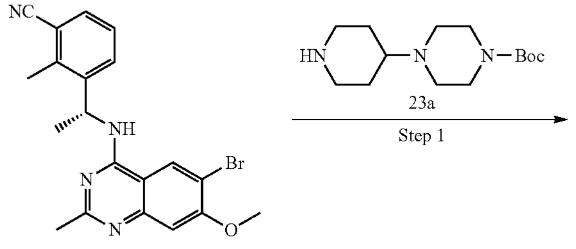

1i

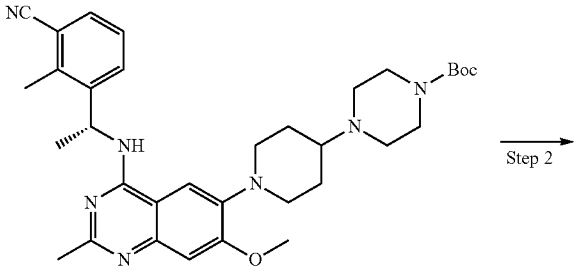

23b

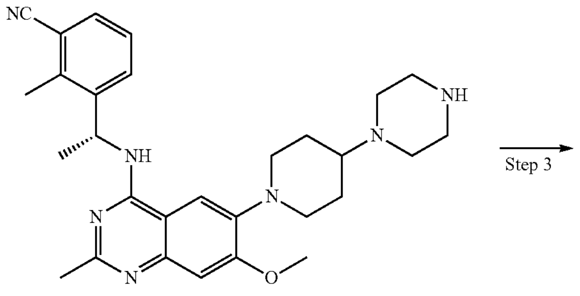

23c

-continued

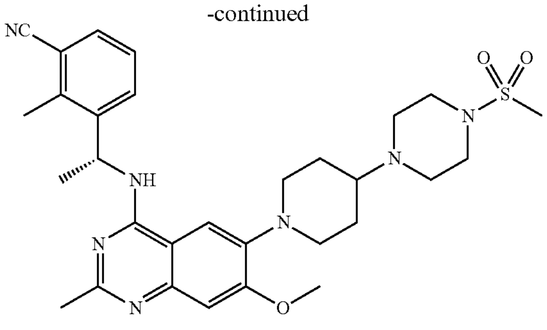

23

Step 1

Tert-butyl (R)-4-(1-(4-((1-(3-cyano-2-methylphenyl)ethyl)amino)-7-methoxy-2-methylquinazolin-6-yl)piperidin-4-yl)piperazine-1-carboxylate (R)-3-(1-((6-bromo-7-methoxy-2-methylquinazolin-4-yl)amino)ethyl)-2-methylbenzonitrile 1i (200 mg, 0.486 mmol), tert-butyl 4-(piperidin-4-yl)piperazine-1-carboxylate 23a (235.8 mg, 0.875 mmol), $Pd_2(dba)_3$ (44.6 mg, 0.048 mmol), BINAP (60.6 mg, 0.097 mmol), sodium tert-butoxide (140.2 mg, 1.46 mmol) and 1,4-dioxane (6 mL) were added to the microwave tube, nitrogen was replaced, and the above mixture reacted at 125 degrees for 1 hour. LC-MS showed that the reaction was completed. The reaction solution was cooled to room temperature, filtered through diatomite, and washed with ethyl acetate. The organic phase of the reaction solution was collected, washed three times with water, and once with saturated salt solution, dried over anhydrous sodium sulfate, filtered, and concentrated under reduced pressure. The obtained residue was purified by silica gel column chromatography (eluent: system B) to obtain 160 mg of tert-butyl (R)-4-(1-(4-((1-(3-cyano-2-methylphenyl)ethyl)amino)-7-methoxy-2-methylquinazolin-6-yl)piperidin-4-yl)piperazine-1-carboxylate 23b, yield 55%.

MS m/z (ESI): 600.3 $[M+1]^+$

Step 2

(R)-3-(1-((7-methoxy-2-methyl-6-(4-(piperazin-1-yl)piperidin-1-yl)quinazolin-4-yl)amino)ethyl)-2-methylbenzonitrile tert-butyl (R)-4-(1-(4-((1-(3-cyano-2-methylphenyl)ethyl)amino)-7-methoxy-2-methylquinazolin-6-yl)piperidin-4-yl)piperazine-1-carboxylate 23b (120 mg, 0.2 mmol), and dioxane (2 mL) were added to a 25 mL flask, 4M hydrogen chloride/1,4-dioxane solution (0.2 mL) was added, the above mixture reacted at room temperature for 2 hours. LC-MS showed that the reaction was completed, and the solvent was concentrated to obtain 90 mg of (R)-3-(1-((7-methoxy-2-methyl-6-(4-(piperazin-1-yl)piperidin-1-yl)quinazolin-4-yl)amino)ethyl)-2-methylbenzonitrile 23c crude product, the above crude product was used directly in the next step.

MS m/z (ESI): 500.3 $[M+1]^+$

Step 3

(R)-3-(1-((7-methoxy-2-methyl-6-(4-(4-(methylsulfonyl)piperazin-1-yl)piperidin-1-yl)quinazolin-4-yl)amino)ethyl)-2-methylbenzonitrile (R)-3-(1-((7-methoxy-2-methyl-6-(4-(piperazin-1-yl)piperidin-1-yl)quinazolin-4-yl)amino)ethyl)-2-methylbenzonitrile 23c crude product (90.00 mg, 0.18 mmol), dichloromethane (8 mL), triethylamine (0.8 mL), methanesulfonyl chloride (61.9 mg, 0.54 mmol) were added to a 25 mL flask, the above mixture reacted at room temperature overnight. LC-MS showed that the reaction was completed. Ethyl acetate was added to the reaction solution, and the reaction solution was washed three times with water and once with saturated salt solution. The organic phase of the reaction solution was dried over anhydrous sodium sulfate, filtered, and concentrated under reduced pressure. The obtained residue was purified by silica gel column chromatography (eluent: system B) to obtain 52 mg of (R)-3-(1-((7-methoxy-2-methyl-6-(4-(4-(methylsulfonyl)piperazin-1-yl)piperidin-1-yl)quinazolin-4-yl)amino)ethyl)-2-methylbenzonitrile 23, yield 48%.

$^1H$ NMR (400 MHz, DMSO-$d_6$) δ 8.17 (d, J=3.4 Hz, 1H), 7.80 (d, J=8.0, 1H), 7.63 (s, 1H), 7.62 (d, J=7.0 Hz, 1H), 7.36 (t, J=7.8 Hz, 1H), 6.97 (s, 1H), 5.64 (p, J=6.9 Hz, 1H), 3.87 (s, 3H), 3.51 (d, J=11.1 Hz, 2H), 3.14-3.10 (m, 4H), 2.88 (s, 3H), 2.72 (s, 3H), 2.68-2.59 (m, 6H), 2.30 (s, 3H), 1.88-1.85 (m, 2H), 1.73-1.58 (m, 2H), 1.53 (d, J=7.1 Hz, 3H) ppm.

MS m/z (ESI): 578.4 $[M+1]^+$

Example 24

(R)-3-(1-((7-methoxy-2-methyl-6-(4-(1-methylpiperidin-4-yl)piperazin-1-yl) quinazolin-4-yl)amino) ethyl)-2-methylbenzonitrile

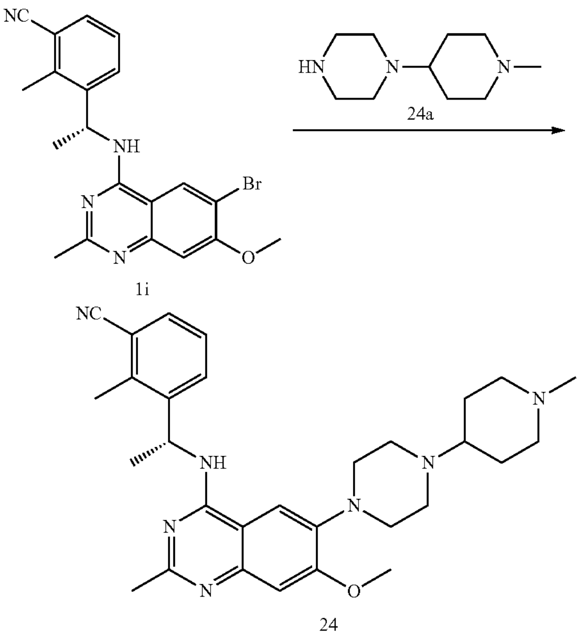

1i 24a 24

(R)-3-(1-((6-bromo-7-methoxy-2-methylquinazolin-4-yl) amino)ethyl)-2-methylbenzonitrile 1i (150.0 mg, 0.365 mmol), 1-(1-methylpiperidin-4-yl)piperazine 24a (133.7 mg, 0.73 mmol), sodium tert-butoxide (105.1 mg, 1.09 mmol), $Pd_2(dba)_3$ (33.4 mg, 0.0365 mmol), BINAP (45.4 mg, 0.073 mmol) and 1,4-dioxane (6 mL) were added to a 10 mL microwave reaction tube, the above mixture reacted at 125 degrees for 1 hour under nitrogen atmosphere. LC-MS showed that the reaction was completed. The reaction solution was cooled to room temperature, filtered through diatomite, and washed with ethyl acetate. The organic phase of the reaction solution was collected, washed three times with water, and once with saturated salt solution, dried over anhydrous sodium sulfate, filtered, and concentrated under reduced pressure. The obtained residue was purified by silica gel column chromatography (eluent: system B) to obtain 40 mg of (R)-3-(1-((7-methoxy-2-methyl-6-(4-(1-methylpiperidin-4-yl)piperazin-1-yl)quinazolin-4-yl)amino)ethyl)-2-methylbenzonitrile 24, yield 21%.

$^1H$ NMR (400 MHz, DMSO-$d_6$) δ 8.16 (d, J=7.1 Hz, 1H), 7.79 (d, J=7.8 Hz, 1H), 7.63 (s, 1H), 7.62 (d, J=8.3 Hz, 1H), 7.35 (t, J=7.8 Hz, 1H), 6.98 (s, 1H), 5.64 (p, J=6.9 Hz, 1H), 3.86 (s, 3H), 3.17-2.99 (m, 4H), 2.85-2.80 (m, 2H), 2.72 (s, 3H), 2.67-2.64 (m, 4H), 2.30 (s, 3H), 2.24-2.20 (m, 1H), 2.18 (s, 3H), 2.02-1.86 (m, 2H), 1.79-1.75 (m, 2H), 1.53 (d, J=7.1 Hz, 3H) 1.48-1.45 (m, 2H) ppm.

MS m/z (ESI): 514.4 $[M+1]^+$

Example 25

(R)-3-(1-((6-(4-(4-ethylpiperazin-1-yl)piperidin-1-yl)-7-methoxy-2-methylquinazolin-4-yl)amino) ethyl)-2-methylbenzonitrile

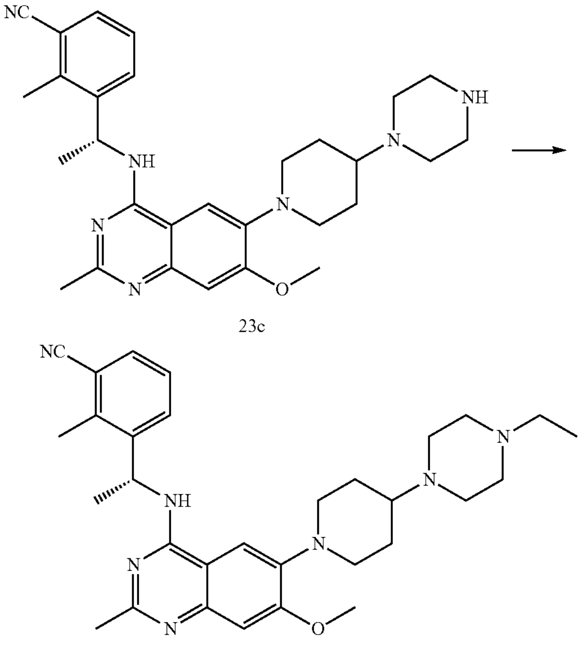

23c 25

(R)-3-(1-((7-methoxy-2-methyl-6-(4-(piperazin-1-yl)piperidin-1-yl)quinazolin-4-yl)amino)ethyl)-2-methylbenzonitrile 23c (120.0 mg, 0.24 mmol), dichloromethane (6 mL), acetaldehyde (31.7 mg, 0.721 mmol), and acetic acid (14.4 mg, 0.24 mmol) were added to a 25 mL flask, the above mixture reacted at room temperature for 2 hours. Sodium cyanoborohydride (45.3 mg, 0.72 mmol) was added and the mixture reacted at room temperature for an additional hour. LC-MS showed that the reaction was completed. Ethyl acetate was added to the reaction solution, and the reaction solution was washed three times with water and once with saturated salt solution. The organic phase of the reaction solution was dried over anhydrous sodium sulfate, filtered, and concentrated under reduced pressure. The obtained residue was purified by silica gel column chromatography (eluent: system B) to obtain 60 mg of (R)-3-(1-((6-(4-(4-ethylpiperazin-1-yl)piperidin-1-yl)-7-methoxy-2-methylquinazolin-4-yl)amino)ethyl)-2-methylbenzonitrile 25, yield 45%.

$^1$H NMR (400 MHz, DMSO-$d_6$) δ 8.24 (d, J=7.1 Hz, 1H), 7.81 (d, J=8.0, 1H), 7.65 (s, 1H), 7.62 (d, J=7.9 Hz, 1H), 7.35 (t, J=7.8 Hz, 1H), 6.98 (s, 1H), 5.65 (p, J=6.9 Hz, 1H), 3.87 (s, 3H), 3.67-3.43 (m, 2H), 2.72 (s, 3H), 2.69-2.60 (m, 3H), 2.30 (s, 3H), 1.92-1.89 (m, 2H), 1.68-1.60 (m, 2H), 1.54 (d, J=7.0 Hz, 3H), 1.08 (t, J=7.2 Hz, 3H) ppm.

MS m/z (ESI): 528.3 [M+1]$^+$

Example 26

(R)-3-(1-((7-acetyl-2-methyl-6-(2-oxa-7-azaspiro[3.5]nonan-7-yl)quinazolin-4-yl)amino)ethyl)-2-methylbenzonitrile

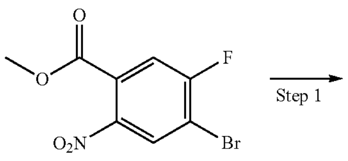

26a

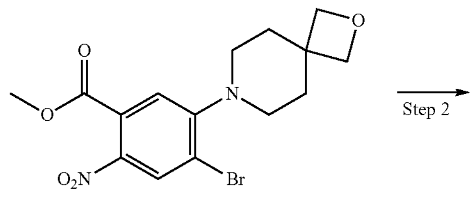

26b

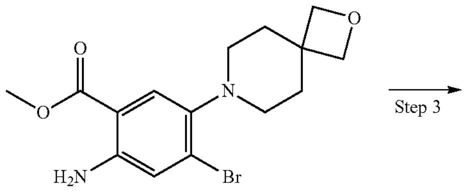

26c

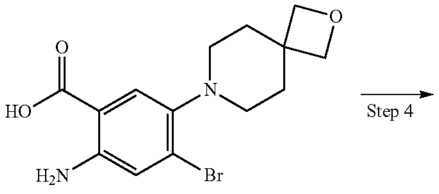

26d

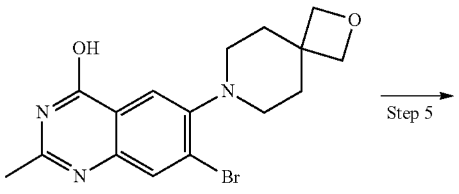

26e

-continued

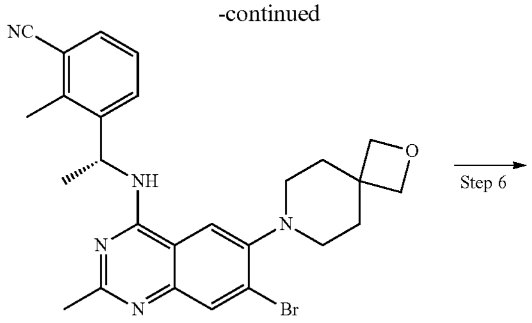

26f

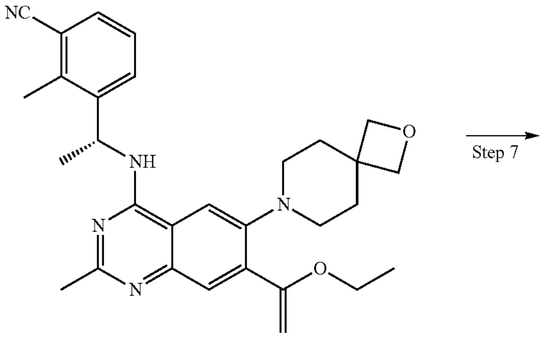

26g

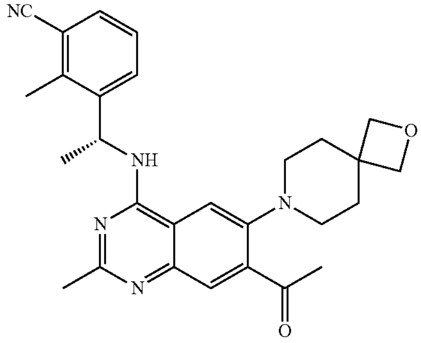

26

Step 1

Methyl 4-bromo-2-nitro-5-(2-oxa-7-azaspiro[3.5]nonan-7-yl)benzoate

Methyl 4-bromo-5-fluoro-2-nitro-benzoate 26a (1.2 g, 4.32 mmol), 2-oxa-7-azaspiro[3.5]nonane (1.56 g, 6.47 mmol), potassium carbonate (1.79 g, 12.95 mmol), and DMF (12 mL) were added sequentially into a 50 mL reaction flask, the above mixture reacted at room temperature for 2 hours. LC-MS showed that the reaction was completed. Saturated aqueous ammonium chloride solution (30 mL) and ethyl acetate were added to the reaction solution. The reaction solution was washed three times with water and once with saturated salt solution. The organic phase of the reaction solution was dried over anhydrous sodium sulfate, filtered, and concentrated under reduced pressure. The obtained residue was separated and purified by silica gel column chromatography (eluent: system A) to obtain 1.3 g of methyl 4-bromo-2-nitro-5-(2-oxa-7-azaspiro[3.5]nonan-7-yl)benzoate 26b, yield 78%.

MS m/z (ESI): 385.1, 387.0 [M+H]$^+$

Step 2

Methyl 2-amino-4-bromo-5-(2-oxa-7-azaspiro[3.5]nonan-7-yl)benzoate

Methyl 4-bromo-2-nitro-5-(2-oxa-7-azaspiro[3.5]nonan-7-yl)benzoate 26b (1.3 g, 3.37 mmol), iron powder (1.01 g, 18.17 mmol), acetic acid (3 mL), and ethanol (15 mL) were added to a 50 mL reaction flask, and the above mixture was heated to 70 degrees and reacted for 4 hours. LC-MS showed that the reaction was completed. The reaction solution was concentrated to evaporate the solvent, ethyl acetate was added, saturated $NaHCO_3$ aqueous solution was added to adjust the pH to 8-10, filtered through diatomite, washed with ethyl acetate, and the organic phase of the reaction solution was concentrated. The obtained residue was separated and purified by silica gel column chromatography (eluent: system A) to obtain 1.1 g of methyl 2-amino-4-bromo-5-(2-oxa-7-azaspiro[3.5]nonan-7-yl)benzoate 26c, yield 85%.

MS m/z (ESI): 355.1, 357.1 $[M+H]^+$

Step 3

2-Amino-4-bromo-5-(2-oxa-7-azaspiro[3.5]nonan-7-yl)benzoic acid

Methyl 2-amino-4-bromo-5-(2-oxa-7-azaspiro[3.5]nonan-7-yl)benzoate 26c (1.1 g, 3.10 mmol), lithium hydroxide monohydrate (259.9 mg, 6.19 mmol), methanol (10 mL), and water (2 mL) were added to a reaction flask, and the above mixture was heated to 65 degrees and reacted for 3 hours. LC-MS showed that the reaction was completed. 1 M HCl was added to adjust the pH of the reaction solution to 2-4. The reaction solution was concentrated to evaporate the solvent, ethyl acetate was added, and washed three times with water. The organic phase of the reaction solution was separated and concentrated under reduced pressure to obtain 1.0 g of 2-amino-4-bromo-5-(2-oxa-7-azaspiro[3.5]nonan-7-yl)benzoic acid 26d, yield 94%.

MS m/z (ESI): 341.1[M+1]

Step 4

7-Bromo-2-methyl-6-(2-oxa-7-azaspiro[3.5]nonan-7-yl)quinazolin-4-ol 2-amino-4-bromo-5-(2-oxa-7-azaspiro[3.5]nonan-7-yl) benzoic acid 26d (1.0 g, 2.93 mmol) and acetic anhydride (12 mL) were added to a 50 mL reaction flask, the above mixture reacted at 140 degrees for 2.5 hours. LC-MS showed that the reaction was completed. The reaction solution was concentrated to evaporate the solvent. The crude reaction product was transferred to a 100 mL sealed tube, ammonia (30 mL) was added, and the crude reaction product reacted at 100 degrees for 3 hours. The crude reaction product was concentrated to remove ammonia, and the sample was mixed with silica gel. The obtained residue was separated and purified by silica gel column chromatography (eluent: system B) to obtain 900 mg of 7-bromo-2-methyl-6-(2-oxa-7-azaspiro[3.5]nonan-7-yl)quinazolin-4-ol 26e, yield 85%.

MS m/z (ESI): 365.1, 367.1 $[M+H]^+$

Step 5

(R)-3-(1-((7-bromo-2-methyl-6-(2-oxa-7-azaspiro[3.5]nonan-7-yl)quinazolin-4-yl)amino)ethyl)-2-methylbenzonitrile 7-bromo-2-methyl-6-(2-oxa-7-azaspiro[3.5]nonan-7-yl) quinazolin-4-ol 26e (450 mg, 1.24 mmol), (R)-3-(1-aminoethyl)-2-methylbenzonitrile hydrochloride 1g (346 mg, 1.48 mmol), BOP (820 mg, 1.85 mmol), DBU (565 mg, 3.71 mmol), DMSO (5 mL) were added to a reaction flask, and the above mixture reacted at room temperature for 3 hours. LC-MS showed that the reaction was completed. Ethyl acetate was added to the reaction solution, and the reaction solution was washed three times with water and once with saturated salt solution. The organic phase of the reaction solution was dried over anhydrous sodium sulfate, filtered, and concentrated under reduced pressure. The obtained residue was separated and purified by silica gel column chromatography (eluent: system A) to obtain 480 mg of (R)-3-(1-((7-bromo-2-methyl-6-(2-oxa-7-azaspiro[3.5]nonan-7-yl)quinazolin-4-yl)amino)ethyl)-2-methylbenzonitrile 26f, yield 76%.

MS m/z (ESI): 506.2, 508.2 $[M+H]^+$

Step 6

(R)-3-(1-((7-(1-ethoxyvinyl)-2-methyl-6-(2-oxa-7-azaspiro[3.5]nonan-7-yl) quinazolin-4-yl)amino)ethyl)-2-methylbenzonitrile (R)-3-(1-((7-bromo-2-methyl-6-(2-oxa-7-azaspiro[3.5]nonan-7-yl)quinazolin-4-yl)amino)ethyl)-2-methylbenzonitrile 26f (300 mg, 0.592 mmol), tributyl(1-ethoxyvinyl)stannane (278.1 mg, 0.77 mmol), $Pd(PPh_3)_2Cl_2$ (83.2 mg, 0.12 mmol), triethylamine (179.8 mg, 1.78 mmol), and 1,4-dioxane (8 mL) were added to the 25 mL reaction flask, nitrogen was replaced three times, and the above mixture reacted at 100 degrees for 3 hours. LC-MS showed that the reaction was completed. The reaction solution was added with potassium fluoride and stirred, filtered through diatomite, concentrated, added with ethyl acetate, washed three times with water and once with saturated salt solution. The organic phase of the reaction solution was dried over anhydrous sodium sulfate, filtered, and concentrated under reduced pressure. The obtained residue was separated and purified by silica gel column chromatography (eluent: system B) to obtain 200 mg of (R)-3-(1-((7-(1-ethoxyvinyl)-2-methyl-6-(2-oxa-7-azaspiro[3.5]nonan-7-yl)quinazolin-4-yl)amino)ethyl)-2-methylbenzonitrile 26g, yield 68%.

MS m/z (ESI): 498.3 $[M+H]^+$

Step 7

(R)-3-(1-((7-acetyl-2-methyl-6-(2-oxa-7-azaspiro[3.5]nonan-7-yl)quinazolin-4-yl)amino)ethyl)-2-methylbenzonitrile (R)-3-(1-((7-(1-ethoxyvinyl)-2-methyl-6-(2-oxa-7-azaspiro[3.5]nonan-7-yl) quinazolin-4-yl)amino)ethyl)-2-methylbenzonitrile 26g (200 mg, 0.402 mmol), dichloromethane (10 mL), trifluoroacetic acid (0.5 mL) were added to a 25 mL reaction flask, the above mixture reacted at room temperature for 1 hour. LC-MS showed that the reaction was completed. Saturated $NaHCO_3$ aqueous solution was added to adjust the pH of the reaction solution to 8-10. Ethyl acetate was added to extract the reaction solution. The organic phase of the reaction solution was washed three times with water and once with saturated salt solution, dried over anhydrous sodium sulfate, filtered, and concentrated under reduced pressure. The obtained residue was separated and purified by silica gel column chromatography (eluent: system B) to obtain 40 mg of (R)-3-(1-((7-acetyl-2-methyl-6-(2-oxa-7-azaspiro[3.5]nonan-7-yl)quinazolin-4-yl)amino)ethyl)-2-methylbenzonitrile 26, yield 24%.

$^1H$ NMR (400 MHz, DMSO-$d_6$) δ 8.52 (d, J=7.0 Hz, 1H), 7.87 (s, 1H), 7.79 (d, J=7.9 Hz, 1H), 7.63 (d, J=7.6 Hz, 1H), 7.42 (s, 1H), 7.36 (t, J=7.8 Hz, 1H), 5.65 (t, J=7.1 Hz, 1H), 4.38 (s, 4H), 2.91-2.88 (m, 4H), 2.71 (s, 3H), 2.59 (s, 3H), 2.33 (s, 3H), 1.97-1.95 (m, 4H), 1.56 (d, J=7.0 Hz, 3H) ppm.

MS m/z (ESI): 470.2 [M+H]$^+$

Example 27

(R)-3-(1-((6-(4-(4-acetylpiperazin-1-yl)piperidin-1-yl)-7-methoxy-2-methylquinazolin-4-yl)amino)ethyl)-2-methylbenzonitrile

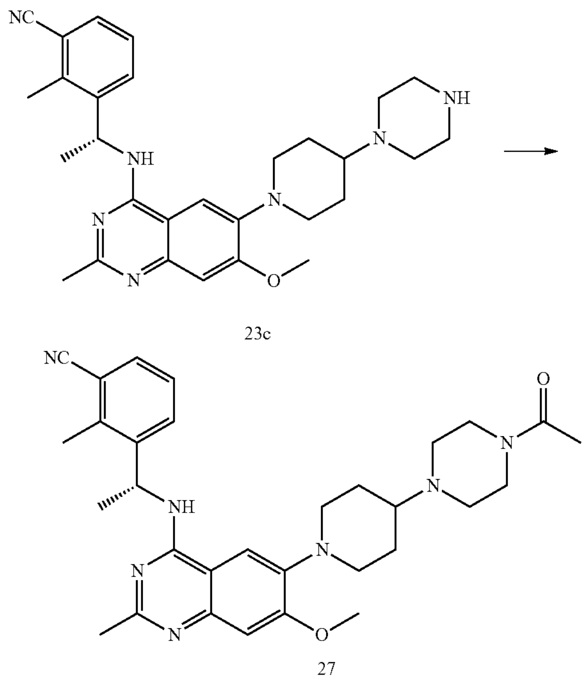

(R)-3-(1-((7-methoxy-2-methyl-6-(4-(piperazin-1-yl)piperidin-1-yl)quinazolin-4-yl)amino)ethyl)-2-methylbenzonitrile 23c (200.0 mg, 0.4 mmol) and acetic anhydride (6 mL) were added to a 25 mL flask, and the above mixture reacted at 140 degrees for 5 hours. LC-MS showed that the reaction was completed. The reaction solution was concentrated to remove acetic anhydride. Water (20 mL) and saturated sodium bicarbonate solution were added to adjust the pH of the reaction solution to slightly basic. The reaction solution was extracted three times with ethyl acetate. The organic phase of the reaction solution was washed once with saturated salt solution, dried over anhydrous sodium sulfate, filtered, and concentrated under reduced pressure. The obtained residue was purified by silica gel column chromatography (eluent: system B) to obtain 90 mg of (R)-3-(1-((6-(4-(4-acetylpiperazin-1-yl)piperidin-1-yl)-7-methoxy-2-methylquinazolin-4-yl)amino)ethyl)-2-methylbenzonitrile 27, yield 40%.

MS m/z (ESI): 542.3[M+H]$^+$ $^1$H NMR (400 MHz, DMSO-$d_6$) δ 8.18 (d, J=7.0 Hz, 1H), 7.80 (d, J=7.9 Hz, 1H), 7.62 (s, 1H), 7.62 (d, J=7.7 Hz, 1H), 7.35 (t, J=7.8 Hz, 1H), 6.97 (s, 1H), 5.64 (q, J=7.2 Hz, 1H), 3.87 (s, 3H), 3.58-3.47 (m, 3H), 3.45-3.41 (s, 4H), 2.72 (s, 3H), 2.71-2.59 (m, 2H), 2.55-2.39 (m, 3H), 2.30 (s, 3H), 1.99 (s, 3H), 1.87-1.84 (m, 2H), 1.68-1.59 (m, 2H), 1.53 (d, J=6.9 Hz, 3H) ppm.

Example 28

(R)-3-(1-((7-methoxy-2-methyl-6-(4-(morpholine-4-carbonyl)piperidin-1-yl) quinazolin-4-yl)amino) ethyl)-2-methylbenzonitrile

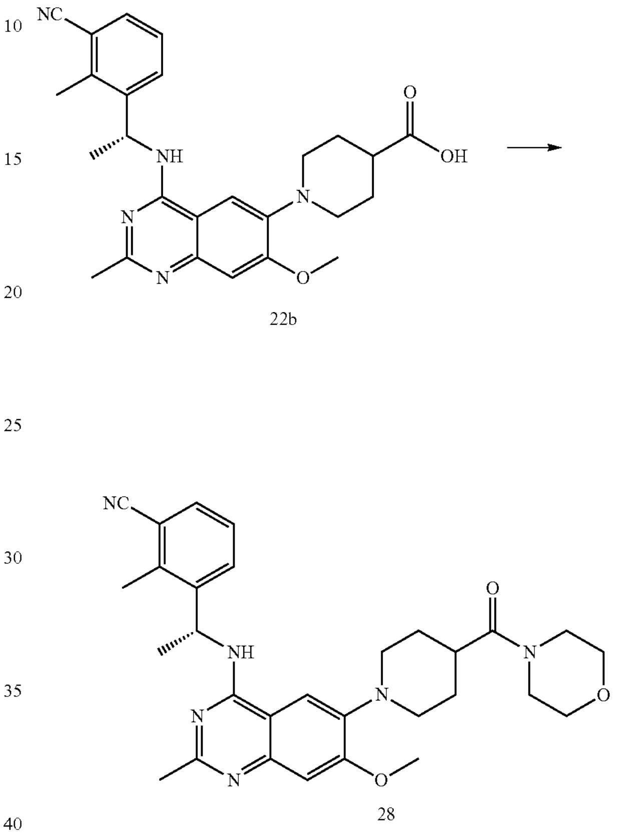

(R)-1-(4-((1-(3-cyano-2-methylphenyl)ethyl)amino)-7-methoxy-2-methylquinazolin-6-yl)piperidine-4-carboxylic acid 22b (200 mg, 0.435 mmol), morpholine (49.3 mg, 0.59 mmol), HATU (248.2 mg, 0.65 mmol), DMF (5 mL), triethylamine (220.2 mg, 2.18 mmol)) were added to a 25 mL flask, and the above mixture reacted at room temperature overnight. LC-MS showed that the reaction was completed. Ethyl acetate was added to wash the reaction solution. The reaction solution was washed three times with water and once with saturated salt solution. The organic phase of the reaction solution was dried over anhydrous sodium sulfate, filtered, and concentrated under reduced pressure. The obtained residue was purified by silica gel column chromatography (eluent: system B) to obtain 200 mg of (R)-3-(1-((7-methoxy-2-methyl-6-(4-(morpholine-4-carbonyl)piperidin-1-yl)quinazolin-4-yl)amino)ethyl)-2-methylbenzonitrile 28, yield 83%.

MS m/z (ESI): 529.3[M+H]$^+$ $^1$H NMR (400 MHz, DMSO-$d_6$) δ 8.34 (s, 1H), 7.80 (d, J=7.9 Hz, 1H), 7.65 (s, 1H), 7.63 (d, J=8.3 Hz, 1H), 7.36 (t, J=7.8 Hz, 1H), 6.98 (s, 1H), 5.65 (q, J=7.3 Hz, 1H), 3.88 (s, 3H), 3.59-3.56 (m, 6H), 3.48 (s, 4H), 2.85-2.75 (m, 3H), 2.71 (s, 3H), 2.32 (s, 3H), 1.84-1.76 (m, 4H), 1.54 (d, J=6.9 Hz, 3H) ppm.

Example 29

(R)-1-(4-((1-(3-cyano-2-methylphenyl)ethyl)amino)-7-methoxy-2-methylquinazolin-6-yl)-N-(2-hydroxyethyl)-N-methylpiperidine-4-carboxamide

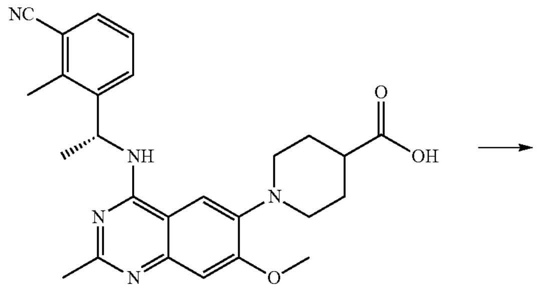

22b

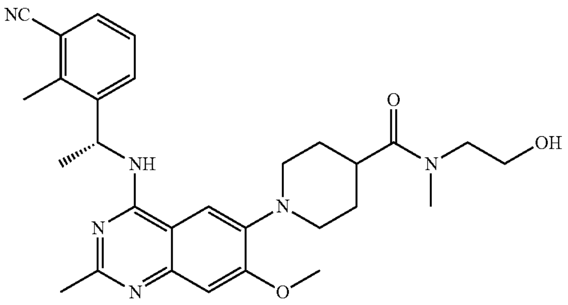

29

(R)-1-(4-((1-(3-cyano-2-methylphenyl)ethyl)amino)-7-methoxy-2-methylquinazolin-6-yl)piperidine-4-carboxylic acid 22b (150 mg, 0.326 mmol), 2-(methylamino)ethyl-1-ol hydrochloride (31.9 mg, 0.424 mmol), HATU (186.2 mg, 0.49 mmol), DMF (2 mL), triethylamine (165.2 mg, 1.63 mmol) were added to a 25 mL flask, and the above mixture reacted at room temperature overnight. LC-MS showed that the reaction was completed. Ethyl acetate was added to wash the reaction solution. The reaction solution was washed three times with water and once with saturated salt solution. The organic phase of the reaction solution was dried with anhydrous sodium sulfate, filtered, and concentrated under reduced pressure. The obtained residue was purified by silica gel column chromatography (eluent: system B) to obtain 20 mg of (R)-1-(4-((1-(3-cyano-2-methylphenyl)ethyl)amino)-7-methoxy-2-methylquinazolin-6-yl)-N-(2-hydroxyethyl)-N-methylpiperidine-4-carboxamide 29, yield 11%.

MS m/z (ESI): 517.3$[M+H]^+$ $^1$H NMR (400 MHz, DMSO-$d_6$) δ 8.67 (s, 1H), 7.81 (d, J=7.9 Hz, 1H), 7.75 (s, 1H), 7.63 (d, J=7.6 Hz, 1H), 7.37 (t, J=7.8 Hz, 1H), 7.02 (s, 1H), 5.69 (q, J=7.0 Hz, 1H), 4.74 (s, 1H), 3.90 (s, 3H), 3.56-3.53 (m, 4H), 3.24-3.21 (m, 4H), 3.08-3.05 (m, 4H), 2.85 (s, 3H), 2.71 (s, 3H), 2.36 (s, 3H), 1.56 (d, J=7.0 Hz, 3H) ppm.

Example 30

Ethyl (R)-4-(4-((1-(3-cyano-2-methylphenyl)ethyl)amino)-7-methoxy-2-methylquinazolin-6-yl)piperazine-1-carboxylate

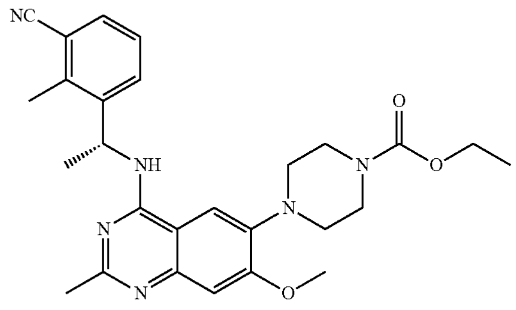

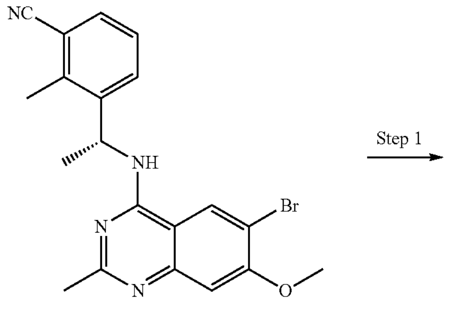

1i

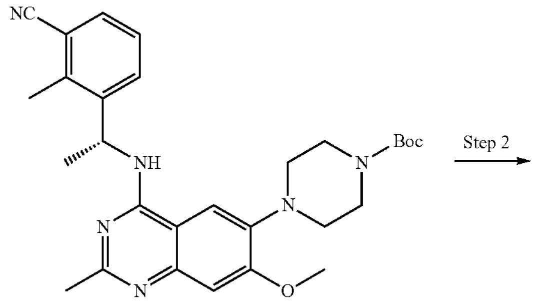

30a

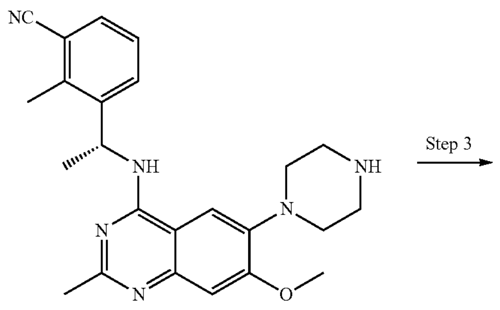

30b

-continued

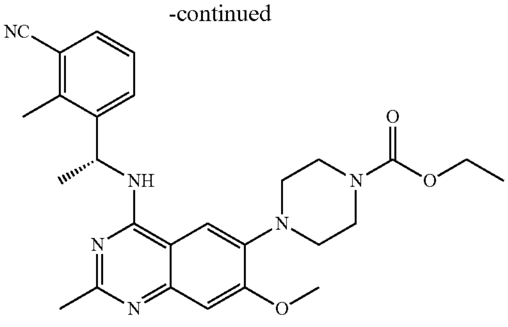

30

Step 1

(R)-3-(1-((6-bromo-7-methoxy-2-methylquinazolin-4-yl) amino)ethyl)-2-methylbenzonitrile 1i (411 mg, 1 mmol), Boc-piperazine (372.5 mg, 2 mmol), tris(dibenzylideneacetone)dipalladium (84 mg, 0.1 mmol), 1,1'-binaphthyl-2,2'-bisdiphenylphosphine (127 mg, 0.2 mmol) and sodium tert-butoxide (384.4 mg, 4 mmol) were added to a microwave tube. 1,4-dioxane (20 mL) was added, and the above mixture reacted under microwave conditions at 125 degrees for 1 hour under $N_2$ atmosphere. LC-MS showed that the reaction was completed. The reaction solution was cooled to room temperature, filtered through diatomite, and washed with ethyl acetate. The organic phase of the reaction solution was collected, washed three times with water and once with saturated salt solution, dried over anhydrous sodium sulfate, filtered, and concentrated under reduced pressure. The obtained residue was purified by silica gel column chromatography (eluent: system B) to obtain 358 mg of tert-butyl (R)-4-(4-((1-(3-cyano-2-methylphenyl)ethyl)amino)-7-methoxy-2-methylquinazolin-6-yl) piperazine-1-carboxylate 30a, yield 70%.

MS m/z (ESI): 517.3[M+H]$^+$

Step 2

Tert-butyl (R)-4-(4-((1-(3-cyano-2-methylphenyl)ethyl) amino)-7-methoxy-2-methylquinazolin-6-yl) piperazine-1-carboxylate 30a (358 mg, 0.69 mmol) was added to a 50 mL reaction flask, 1,4-dioxane (15 mL) was added, and 4M HCl/1,4-dioxane solution (6 mL) was added, and the mixture was stirred at room temperature for 4 hours. LC-MS showed that the reaction was completed. The solvent was removed from the reaction solution under reduced pressure, ethyl acetate was added, saturated sodium bicarbonate was used to adjust the pH of the reaction solution to slightly basic, and the reaction solution was extracted. The organic phase of the reaction solution was washed three times with water and once with saturated salt solution, and the solvent was removed under reduced pressure to obtain 276 mg of (R)-3-(1-((7-methoxy-2-methyl-6-(piperazin-1-yl)quinazolin-4-yl)amino)ethyl)-2-methylbenzonitrile 30b crude product, the above crude product was directly used in the next reaction.

MS m/z (ESI): 417.2[M+H]$^+$

Step 3

(R)-3-(1-((7-methoxy-2-methyl-6-(piperazin-1-yl)quinazolin-4-yl)amino)eth yl)-2-methylbenzonitrile 30b (80 mg, 0.19 mmol) was added to a 25 mL one-neck flask, dichloromethane (10 mL), triethylamine (0.2 mL), and ethyl chloroformate (42 mg, 0.38 mmol) were added, and the above mixture reacted at room temperature for 1 hour. LC-MS showed that the reaction was completed. Dichloromethane was added to the reaction solution, and the reaction solution was washed three times with water and once with saturated salt solution. The organic phase of the reaction solution was dried with anhydrous sodium sulfate, filtered, and concentrated under reduced pressure. The obtained residue was purified by silica gel column chromatography (eluent: system B) to obtain 40.5 mg of ethyl (R)-4-(4-((1-(3-cyano-2-methylphenyl)ethyl)amino)-7-methoxy-2-methylquinazolin-6-yl)piperazine-1-carboxylate 30, yield 41%.

MS m/z (ESI): 489.3[M+H]$^+$ $^1$H NMR (400 MHz, DMSO-$d_6$) δ 8.19 (d, J=7.5 Hz, 1H), 7.78 (d, J=7.9 Hz, 1H), 7.67 (s, 1H), 7.62 (d, J=7.5 Hz, 1H), 7.36 (t, J=7.8 Hz, 1H), 7.00 (s, 1H), 5.64 (p, J=7.1 Hz, 1H), 4.08 (q, J=7.0 Hz, 2H), 3.88 (s, 3H), 3.56 (s, 4H), 3.03 (d, J=5.1 Hz, 4H), 2.71 (s, 3H), 2.30 (s, 3H), 1.53 (d, J=6.9 Hz, 3H), 1.21 (t, J=7.1 Hz, 3H) ppm.

Example 31

(R)-3-(1-((7-methoxy-2-methyl-6-(4-(morpholine-4-carbonyl)piperazin-1-yl)quinazolin-4-yl)amino) ethyl)-2-methylbenzonitrile

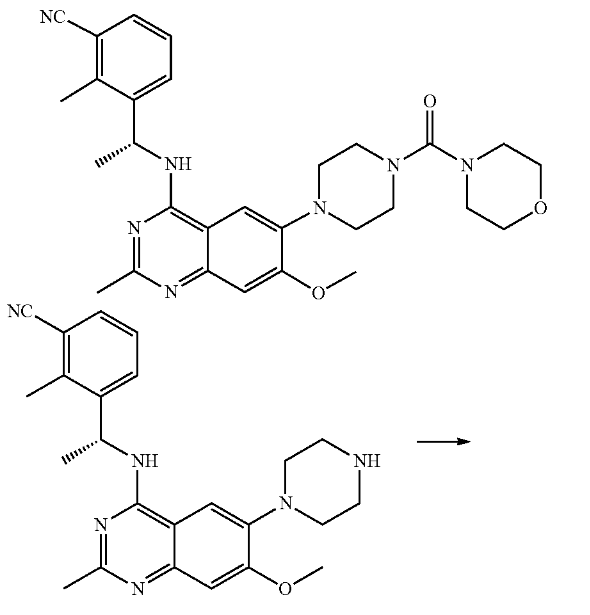

30b

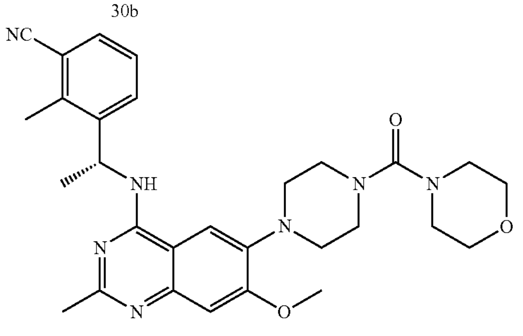

31

(R)-3-(1-((7-methoxy-2-methyl-6-(piperazin-1-yl)quinazolin-4-yl)amino)eth yl)-2-methylbenzonitrile 30b (80 mg, 0.19 mmol) was added to a 25 mL one-neck flask, dichloromethane (5 mL), triethylamine (0.2 mL), and morpholine-4-carbonyl chloride (57.5 mg, 0.38 mmol) were added, and the mixture reacted at room temperature for 3 hours. LC-MS showed that the reaction was completed. Dichloromethane was added to the reaction solution, and the reaction solution was washed three times with water and once with saturated salt solution. The organic phase of the reaction solution was dried over anhydrous sodium sulfate, filtered, and concentrated under reduced pressure. The obtained residue was purified by silica gel column chromatography (eluent: System B) to obtain 16.1 mg of (R)-3-(1-((7-methoxy-2-methyl-6-(4-(morpholine-4-carbonyl)piperazin-1-yl)quinazolin-4-yl)amino)ethyl)-2-methylbenzonitrile 31, yield 16%.

MS m/z (ESI): 530.3[M+H]$^+$ $^1$H NMR (400 MHz, DMSO-$d_6$) δ 8.19 (d, J=7.4 Hz, 1H), 7.79 (d, J=7.9 Hz, 1H), 7.67 (s, 1H), 7.62 (d, J=7.7 Hz, 1H), 7.36 (t, J=7.8 Hz, 1H), 7.00 (s, 1H), 5.93-5.52 (m, 1H), 3.88 (s, 3H), 3.59 (s, 4H), 3.37-3.18 (m, 8H), 3.07-3.01 (m, 4H), 2.72 (s, 3H), 2.30 (s, 3H), 1.53 (d, J=7.0 Hz, 3H) ppm.

Example 32

(R)-3-(1-((6-(1-acetyl-4-methoxypiperidin-4-yl)-7-methoxy-2-methylquinazolin-4-yl)amino)ethyl)-2-methylbenzonitrile

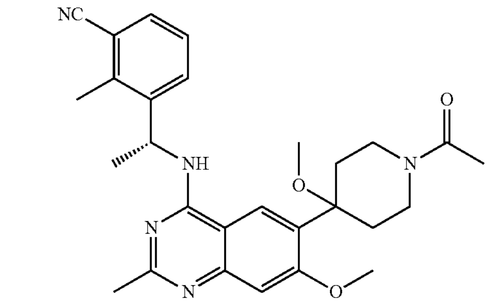

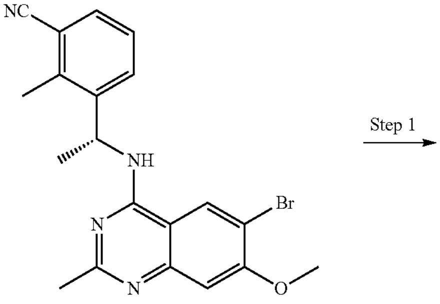

1i

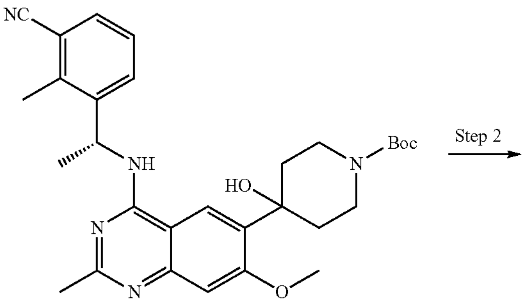

32a

-continued

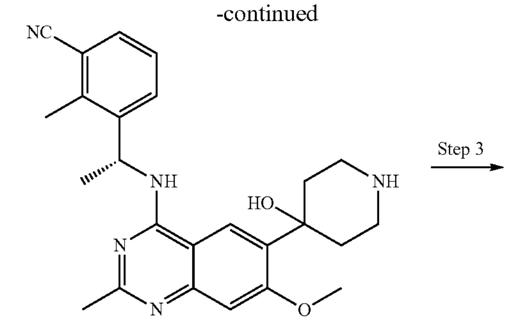

32b

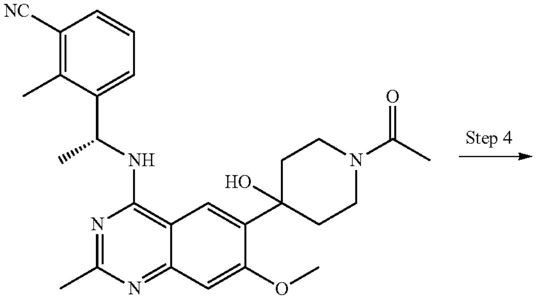

32c

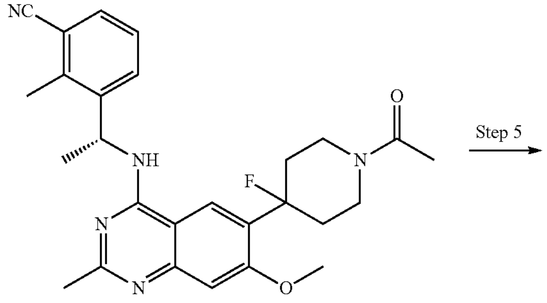

32d

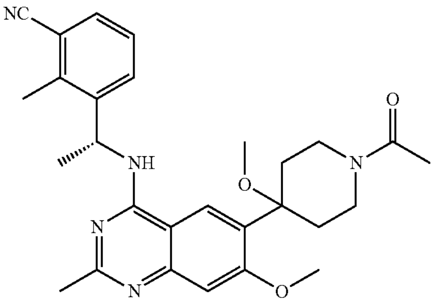

32

Step 1

(R)-3-(1-((6-bromo-7-methoxy-2-methylquinazolin-4-yl)amino)ethyl)-2-methylbenzonitrile 1i (1.64 g, 4 mmol) was added to a 250 mL three-necked flask, and tetrahydrofuran (40 mL) was added. Nitrogen was replaced three times, the temperature was lowered to −78 degrees, 2.7 M methyllithium solution in diethoxymethane (2.3 mL, 6 mmol) was added, and the above mixture reacted with the temperature kept for 15 minutes. 2.5M n-butyllithium solution in n-hexane (2.4 mL, 6 mmol) was added, and the mixture reacted with the temperature kept for 1 hour. tert-butyl 4-oxo-piperidine-1-carboxylate (2.39 g, 12 mmol) was dissolved in tetrahydrofuran (20 mL) and slowly added to the above reaction solution through a syringe. After the addition was completed, the temperature was returned to room temperature, and the above mixture reacted for 2 hours. The reaction solution was quenched by adding saturated ammonium chloride solution, and extracted with ethyl acetate. The organic phase of the reaction solution was washed three times with water and once with saturated salt solution, dried over anhydrous sodium sulfate, filtered, and concentrated under reduced pressure. The obtained residue was purified by silica gel column chromatography (eluent: system B) to obtain 500 mg of tert-butyl (R)-4-(4-((1-(3-cyano-2-methylphenyl)ethyl)amino)-7-methoxy-2-methylquinazolin-6-yl)-4-hydroxy-piperidine-1-carboxylate 32a, yield 24%.

MS m/z (ESI): 532.3[M+H]$^+$

Step 2

Tert-butyl (R)-4-(4-((1-(3-cyano-2-methylphenyl)ethyl)amino)-7-methoxy-2-methylquinazolin-6-yl)-4-hydroxy-piperidine-1-carboxylate 32a (500 mg, 0.71 mmol) was added to the 100 mL one-neck flask, 1,4-dioxane (20 mL) was added, 4M hydrogen chloride/1,4-dioxane solution (5 mL) was added, and the above mixture reacted at room temperature for 2 hours. LC-MS showed that the reaction was completed. The solvent was removed under reduced pressure to obtain 350 mg of (R)-3-(1-((6-(4-hydroxy-piperidin-4-yl)-7-methoxy-2-methylquinazolin-4-yl)amino)ethyl)-2-methylbenzonitrile 32b crude product, the above crude product was directly used in the next step.

MS m/z (ESI): 432.3[M+H]$^+$

Step 3

350 mg crude product of (R)-3-(1-((6-(4-hydroxy-piperidin-4-yl)-7-methoxy-2-methylquinazolin-4-yl))amino)ethyl)-2-methylbenzonitrile 32b was dissolved in DMF (5 mL), acetic acid (83.5 mg), HATU (528 mg), and DIPEA (360 mg) were added, and the above mixture was stirred at room temperature overnight. LC-MS showed that the reaction was completed. Ethyl acetate was added to the reaction solution, the reaction solution was washed three times with water. The organic phase of the reaction solution was washed once with saturated salt solution, dried over anhydrous sodium sulfate, filtered, and concentrated. The obtained residue was purified by silica gel column chromatography (eluent: system B) to obtain 200 mg of (R)-3-(1-((6-(1-acetyl-4-hydroxy-piperidine-4-yl)-7-methoxy-2-methylquinazolin-4-yl)amino)ethyl)-2-methylbenzonitrile 32c product, the combined yield of the two steps was 60%.

MS m/z (ESI): 474.3[M+H]$^+$

Step 4

(R)-3-(1-((6-(1-acetyl-4-hydroxy-piperidine-4-yl)-7-methoxy-2-methylquinazolin-4-yl)amino)ethyl)-2-methylbenzonitrile 32c (200 mg, 0.36 mmol) was added to dichloromethane (5 mL), cooled to 0 degrees in an ice bath, DAST (173.6 mg, 1.08 mmol) was added, the above mixture reacted for 3 hours after returning to room temperature. LC-MS showed that the reaction was completed. Saturated sodium bicarbonate aqueous solution was added to adjust the pH of the reaction solution to 7-9. The organic phase of the reaction solution was separated, and the aqueous phase of the reaction solution was extracted twice with dichloromethane. The organic phases were combined, dried over anhydrous sodium sulfate, filtered, and concentrated. The obtained residue was purified by silica gel column chromatography (eluent: system B) to obtain 110 mg of (R)-3-(1-((6-(1-acetyl-4-fluoro-piperidin-4-yl)-7-methoxy-2-methylquinazolin-4-yl)amino)ethyl)-2-methylbenzonitrile 32d, yield 65%.

MS m/z (ESI): 476.3[M+H]$^+$

Step 5

(R)-3-(1-((6-(1-acetyl-4-fluoro-piperidin-4-yl)-7-methoxy-2-methylquinazolin-4-yl)amino)ethyl)-2-methylbenzonitrile 32d (110 mg, 0.23 mmol), methanol/water (5 mL/2.5 mL) and sodium methoxide (125.0 mg, 2.3 mmol) were added to a 25 mL one-neck flask, and the mixture reacted at 70 degrees for 8 hours. LC-MS showed that the reaction was completed. The solvent was removed under reduced pressure, ethyl acetate was added to the reaction solution, the reaction solution was washed three times with water and once with saturated salt solution, dried over anhydrous sodium sulfate, filtered, and concentrated to obtain 21 mg of (R)-3-(1-((6-(1-acetyl-4-methoxypiperidin-4-yl)-7-methoxy-2-methylquinazolin-4-yl)amino)ethyl)-2-methylbenzonitrile 32, yield 18%.

MS m/z (ESI): 488.3[M+H]$^+$ $^1$H NMR (400 MHz, DMSO-$d_6$) δ 8.48 (s, 1H), 8.10 (s, 1H), 7.80 (s, 1H), 7.62 (d, J=7.7 Hz, 1H), 7.36 (t, J=7.8 Hz, 1H), 7.05 (s, 1H), 5.66 (t, J=6.9 Hz, 1H), 4.38-4.33 (m, 1H), 3.86 (s, 3H), 3.72-3.67 (m, 1H), 3.43-3.39 (m, 1H), 2.95 (s, 3H), 2.90-2.84 (m, 1H), 2.72 (s, 3H), 2.42-2.37 (m, 2H), 2.32 (s, 3H), 2.27-2.25 (m, 1H), 2.03 (s, 3H), 1.98-1.94 (m, 1H), 1.55 (d, J=6.9 Hz, 3H) ppm.

Biological Evaluation

Test Example 1. Test of the Compounds of the Present Invention for Blocking the Binding of KRAS G12C Protein to SOS1

The following method was used to determine the abilities of compounds of the invention to block the interaction of SOS1 with the KRAS G12C protein in vitro. KRAS-G12C/SOS1 BINDING ASSAY KITS (Art. No. 63ADK000CB16PEG) from Cisbio was used in this method. Please refer to the kit instruction for detailed experimental operations.

The experimental process can be briefly described as follows: diluent buffer (Art. No. 62DLBDDF) was used to prepare a working solution with a concentration of 5× for Tag1-SOS1 and Tag2-KRAS-G12C protein. The test compounds were dissolved in DMSO to prepare storage solutions of 10 mM, and then the solutions were diluted with dilution buffer for later use. First, 2 μL of the test compound (the final concentrations of the reaction system were 10000 nM-0.1 nM) was added to the well, then 4 μL of Tag1-SOS1 5× working solution and 4 μL of Tag2-KRAS-G12C 5× working solution were added, and the above mixture was centrifuged, mixed, and stood for 15 minutes; then 10 μL of premixed anti-Tag1-$Tb^{3+}$ and anti-Tag2-XL665 were added, and the mixture was incubated at room temperature for 2 hours; finally, a microplate reader was used in TF-FRET mode to measure the fluorescence intensity of each well emitting wavelengths of 620 nM and 665 nM under the excitation wavelength of 304 nM, and the fluorescence intensity ratio 665/620 in each well was calculated. Compared with the fluorescence intensity ratio of a control group (0.1% DMSO), the percentage inhibition rates of the test compounds at each concentration were calculated, and the $IC_{50}$ values of the compounds were obtained by performing nonlinear regression analysis with logarithmic values of the compound concentration-inhibition rate by GraphPad Prism 5 software, which was shown in Table 1.

TABLE 1

| Compound number | $IC_{50}$ (nM) Inhibition of KRAS-G12C/SOS1 binding |
|---|---|
| 1 | 26.2 |
| 2 | 20.7 |
| 4 | 65.2 |
| 5 | 28.0 |
| 6 | 1.1 |
| 7 | 35.7 |
| 8 | 62.0 |
| 9 | 53.7 |
| 10 | 36.7 |
| 11 | 39.5 |
| 12 | 88.4 |
| 15 | 31.7 |
| 16 | 54.3 |
| 16c | 20.3 |
| 19 | 22.3 |
| 21 | 63.2 |

Activities of the compounds of the present invention for blocking the binding of KRAS G12C protein and SOS1

Conclusion: the compounds of the present invention have strong blocking effects on the interaction between KRAS G12C protein and SOS1.

Test Example 2. Determination of the Inhibition of the Compounds of the Present Invention on OCI-AML5 Cell Proliferation The following method was used to determine the influence of the compounds of the present invention on OCI-AML5 cells proliferation. OCI-AML5 cells (containing SOS1 N233Y mutation) were purchased from Nanjing Kebai Biotechnology Co., Ltd. and cultured in MEMα medium containing 10% fetal bovine serum, 100 U penicillin, and 100 μg/mL streptomycin. The activities of the cells were determined by CellTiter-Glo® Luminescent Cell Viability Assay Kit (Promega, Art. No. G7573).

The experimental method was operated according to the steps in the kit instruction, which were briefly described as follows: the test compounds were first dissolved in DMSO to prepare storage solutions of 10 mM, and then diluted with culture mediums to prepare test samples. The final concentrations of the compounds were 10000 nM to 0.15 nM. Cells in logarithmic phase were inoculated in a 96-well cell culture plate with 1,000 cells per well, after cultured overnight in 5% $CO_2$ incubator at 37° C., the test compounds were added to the incubator to continue the culture for 120 hours. After the culture was completed, 50 μL of CellTiter-Glo detection solution was added to each well, shaken for 5 minutes and then stood for 10 minutes. Then, a Luminescence mode was used to read the luminescence values of each well of the samples on a microplate reader. By comparing with the numerical value of a control group (0.3% DMSO), the percentage inhibition rates of the compounds at each concentration were calculated, and the $IC_{50}$ values of the compounds inhibiting cell proliferation were obtained by performing nonlinear regression analysis with logarithmic values of the compound concentration-inhibition rate by GraphPad Prism 5 software, which can be seen in Table 2.

TABLE 2

Inhibition activities of the compounds of the present invention on OCI-AML5 cells proliferation

| Compound number | $IC_{50}$ (nM) Inhibition on OCI-AML5 cell proliferation |
|---|---|
| 1 | 46.4 |
| 2 | 8.4 |
| 3 | 42.9 |
| 4 | 6.3 |
| 5 | 11.3 |
| 6 | 5.5 |
| 7 | 2.7 |
| 8 | 12.0 |
| 9 | 25.0 |
| 10 | 16.8 |
| 11 | 13.6 |
| 12 | 23.0 |
| 13 | 25.4 |
| 15 | 3.7 |
| 16c | 13.1 |
| 17 | 10.6 |
| 18 | 2.6 |
| 19 | 16.4 |
| 22 | 7.2 |
| 23 | 41.1 |
| 26 | 17.4 |

Conclusion: the compounds of the present invention have good inhibition effects on OCI-AML5 cell proliferation.

Test Example 3. Determination of the Inhibition Activities of the Compounds of the Present Invention on p-ERK1/2 in DLD-1 Cells The following method was used to determine the inhibition activities of the compounds of the present invention on p-ERK1/2 in DLD-1 cells. The Advanced phospho-ERK1/2 (Thr202/tyr204) kit (Art. No. 64AERPEH) from Cisbio was used in this method. Please refer to the kit instruction for detailed experimental operations. DLD-1 cells (containing KRAS G13D mutation) were purchased from the Cell Resource Center of Shanghai Institutes for Biological Sciences, Chinese Academy of Sciences.

The experimental process can be briefly described as follows: DLD-1 cells were cultured in RPMI 1640 complete medium containing 10% fetal bovine serum, 100 U penicillin, 100 μg/mL streptomycin and 1 mM Sodium Pyruvate. DLD-1 cells were plated in a 96-well plate at 30,000 cells per well, after cultured overnight in 5% $CO_2$ incubator at 37° C. with complete culture medium. The test compounds were dissolved in DMSO to prepare storage solutions of 10 mM, and then diluted with RPMI 1640 basic mediums. 90 μL of RPMI 1640 basic mediums containing the test compounds at the corresponding concentration were added to each well. The final concentrations of the test compounds in the reaction system were 10,000 nM to 0.15 nM, and were placed in a cell culture incubator for 3 hours and 40 minutes. Subsequently, 10 μL of hEGF (purchased from Roche, Art. No. 11376454001) prepared with RPMI 1640 basic medium was added to a final concentration of 5 nM, and placed in the incubator for culturing for 20 minutes. The cell supernatant was discarded, and the cells were washed with PBS on ice-bath. Then, 45 μl of 1× cell phospho/total protein lysis buffer (component of Advanced phospho-ERK1/2 kit) was added to each well for lysis. The 96-well plate was placed on ice for 0.5 hours to lyse, and then the lysate was detected according to the instruction of the Advanced phospho-ERK1/2 (Thr202/tyr204) kit. Finally, the microplate reader was used in TF-FRET mode to measure the fluorescence intensity of each well emitting wavelengths of 620 nM and 665 nM under the excitation wavelength of 304 nM, and the fluorescence intensity ratio 665/620 in each well was calculated. By comparing with the fluorescence intensity ratio of a control group (0.1% DMSO), the percentage inhibition rates of the test compounds at each concentration were calculated, and the $IC_{50}$ values of the compounds were obtained by performing nonlinear regression analysis with logarithmic values of the compound concentration-inhibition rate by GraphPad Prism 5 software, which can be seen in Table 3.

TABLE 3

Inhibition activities of the compounds of the present invention on p-ERK1/2 in DLD-1 cells

| Compound number | $IC_{50}$ (nM) Inhibition on p-ERK½ in DLD-1 cells |
|---|---|
| 1 | 48.7 |
| 2 | 65.4 |
| 5 | 66.1 |
| 7 | 31.1 |
| 8 | 38.2 |
| 11 | 29.7 |
| 13 | 73.5 |
| 17 | 29.2 |
| 19 | 46.3 |
| 22 | 20.9 |
| 27 | 31.2 |

Conclusion: the compounds of the present invention have good inhibition effects on ERK phosphorylation in DLD-1 cells.

Test Example 4. Determination of the Inhibition of the Compounds of the Present Invention on NCI-H358 Cell Proliferation The following method was used to determine the effects of the compounds of the present invention on NCI-H358 cell proliferation under three-dimensional (3D) non-anchored conditions. NCI-H358 cells (containing KRAS G12C mutation) were purchased from the Cell Resource Center of Shanghai Institutes for Biological Sciences, Chinese Academy of Sciences, and cultured in RPMI 1640 medium containing 10% fetal bovine serum, 100 U penicillin, 100 μg/mL streptomycin and 1 mM Sodium Pyruvate. The activities of the cells were determined by CellTiter-Glo® 3D Cell Viability Assay Kit (Promega, Art. No. G9683).

The experimental method was operated according to the steps in the kit instruction, which can be briefly described as follows: the test compounds were first dissolved in DMSO to prepare storage solutions of 10 mM, and then diluted with culture mediums to prepare test samples. The final concentrations of the compounds were 10000 nM to 0.15 nM. Cells in logarithmic phase were inoculated in an ultra-low adsorption 384-well cell culture plate (PerkinElmer, #3830) with 2000 cells per well, and the test compounds were added and cultured for 120 hours. After the culture was completed, 30 μL of CellTiter-Glo 3D detection solution was added to each well, shaken for 30 minutes and then stood for 120 minutes. Then, a Luminescence mode was used to read the luminescence values of each well of the samples on a microplate reader. By comparing with the numerical value of a control group (0.1% DMSO), the percentage inhibition rates of the compounds at each concentration were calculated, and the $IC_{50}$ values of the compounds inhibiting cell proliferation were obtained by performing nonlinear regression analysis with logarithmic values of the compound concentration-inhibition rate by GraphPad Prism 5 software, which can be seen in Table 4.

TABLE 4

Inhibition activities of the compounds of the present invention on NCI-H358 cell proliferation

| Compound number | $IC_{50}$ (nM) Inhibition on NCI-H358 cell proliferation |
|---|---|
| 1 | 78.3 |
| 2 | 49.6 |
| 4 | 7.0 |
| 5 | 10.7 |
| 11 | 71.4 |
| 18 | 6.9 |
| 19 | 21.2 |
| 20 | 52.4 |
| 22 | 15.1 |

Conclusion: the compounds of the present invention have good inhibition effects on H358 cell proliferation.

Test Example 5. Pharmacokinetic Evaluation of the Compounds of the Present Disclosure in ICR Mice 1. Abstract ICR normal mice were used as test animals, and LC/MS/MS was used to determine the drug concentrations at different moments in plasma of ICR mice by intragastric administration. The pharmacokinetic behavior of the compounds of the present invention in ICR mice was studied to evaluate the pharmacokinetic characteristics of the above compounds.

2. Experimental Plan 2.1 Experimental Drugs

Compound 4, Compound 26 and Compound 32.

2.2 Experimental Animals

ICR mice, male, 27.8-38 g, were purchased from Zhejiang Vital River Laboratory Animal Technology Co., Ltd.

2.3 Preparation of Drugs

An appropriate amount of the compound was weighed, and DMA:30% Solutol HS-15:Saline=5:5:90 (v/v/v) was used as the solvent to prepare a fully dissolved solution, and then administered to obtain a 1 mg/mL colorless solution.

2.4 Administration

The ICR mice in the intragastric group of each compound to be tested (nine mice in each group) were fasted overnight followed by intragastric administration (administration dosage was 10 mg/kg and the administration volume was 10 mL/kg), and ate 4 hours after administration.

3. Operation 0.1 mL of blood was collected via orbit before administration and 0.25 hour, 0.5 hour, 1 hour, 2 hours, 4 hours, 8 hours, 12 hours, and 24 hours after administration, and placed in EDTA-K2 anticoagulant tubes. The collected blood samples were placed on ice, and plasma was separated by centrifugation (centrifugation condition: 1500 g, 10 minutes). The collected plasma samples were stored at −40~−20° C. before analysis.

LC-MS/MS was used to determine the content of the compound to be tested in mouse plasma after intragastric administration.

4. Results of Pharmacokinetic Parameters

The pharmacokinetic parameters of the compounds of the present invention can be seen in the table below.

TABLE 5

Pharmacokinetic parameters of the compounds of the present invention in mice

| | Pharmacokinetic experiments | | | |
|---|---|---|---|---|
| Compound number | Administration mode Administration dose | Plasma concentration $C_{max}$ (ng/mL) | Area under curve $AUC_{0-t}$ (ng · h/mL) | Half-life $T_{1/2}$ (h) |
| 4 | PO (10 mg/kg) | 2310 | 5820 | 0.85 |
| 26 | PO (10 mg/kg) | 2830 | 7700 | 1.98 |
| 32 | PO (10 mg/kg) | 5610 | 22100 | 2.29 |

Conclusion: the compounds of the present invention have good pharmacokinetic properties in ICR mice.

Test Example 6. Pharmacokinetic Evaluation of the Compounds of the Present Invention in Balb/c Mice 1. Abstract Balb/c normal mice were used as test animals, and LC/MS/MS was used to determine the drug concentrations at different moments in plasma of balb/c mice by intragastric administration. The pharmacokinetic behavior of the compounds of the present invention in Balb/c mice was studied to evaluate the pharmacokinetic characteristics of the above compounds.

2. Experimental Plan 2.1 Experimental Drugs

Compound 27 and Compound 30.

2.2 Experimental Animals

Nine Balb/c normal mice, male, were evenly divided into 3 groups, with 3 mice in each group, purchased from Zhejiang Vital River Laboratory Animal Technology Co., Ltd.

2.3 Preparation of Drugs

An appropriate amount of the compound was weighed, and DMA:30% Solutol HS-15:Saline=5:5:90 (v/v/v) was used as the solvent to prepare a fully dissolved solution with a concentration of 1 mg/mL.

2.4 Administration

The mice in the intragastric group of each compound to be tested (nine mice in each group) were fasted overnight followed by intragastric administration (administration dosage was 10 mg/kg and the administration volume was 10 mL/kg), and ate 4 hours after administration.

3. Operation 0.1 mL of blood was collected via jugular vein before administration and 0.25 hour, 0.5 hour, 1 hour, 2 hours, 4 hours, 6 hours, 8 hours, and 24 hours after administration, and placed in 0.1% sodium heparin anticoagulant test tubes. The collected blood samples were placed on ice, and plasma was separated by centrifugation (centrifugation condition: 7000 g, 5 minutes). The collected plasma samples were stored at −80° C. before analysis.

LC-MS/MS was used to determine the content of the compound to be tested in mouse plasma after intragastric administration.

4. Results of Pharmacokinetic Parameters

The pharmacokinetic parameters of the compounds of the present invention can be seen in the table below.

TABLE 6

Pharmacokinetic parameters of the compounds of the present invention in mice

| | Pharmacokinetic experiments | | | |
|---|---|---|---|---|
| Compound number | Administration mode Administration dose | Plasma concentration $C_{max}$ (ng/mL) | Area under curve $AUC_{0-t}$ (ng · h/mL) | Half-life $T_{1/2}$ (h) |
| 27 | PO (10 mg/kg) | 1150 | 4663 | 4.91 |
| 30 | PO (10 mg/kg) | 4658 | 10812 | 0.79 |

Conclusion: the compounds of the present invention have good pharmacokinetic properties in Balb/c mice.

Test Example 7. Pharmacokinetic Evaluation of the Compound of the Present Invention in Rats 1. Purpose of Experiment SD rats were used as the test animals, and LC/MS/MS was used to determine the drug concentrations at different moments in plasma after compound 11 of the present invention was administered to the rats through intravenous injection or intragastric administration. The pharmacokinetic characteristics of compound 11 of the present invention in SD rats were studied.

2. Experimental Plan 2.1 Experimental Drugs

Compound 11 of the present invention;

2.2 Experimental Animals

SD rats, male, 195-235 g, 6-8 weeks old, were purchased from Vital River Laboratory Animal Technology Co., Ltd.

2.3 Preparation of Drugs

Intravenous injection group: an appropriate amount of the compound to be tested was weighed, and an appropriate amount of DMA:30% Solutol HS-15:Saline=5:5:90 (v/v/v) was added respectively, vortexed, and a solution with a final concentration of 0.2 mg/mL was prepared.

Intragastric administration group: an appropriate amount of the compound to be tested was weighed, and an appropriate amount of DMA:30% Solutol HS-15:Saline=5:5:90 (v/v/v) was added, vortexed, and a solution with a final concentration of 1 mg/mL was prepared.

2.4 Administration

The SD rats were divided into intravenous injection group (3 rats/group) and intragastric administration group (3 rats/group) according to the compound to be tested.

Intravenous injection group: rats were fasted overnight and then administered by intravenous injection (administration dosage was 1 mg/kg, and administration volume was 5 mL/kg), and ate 4 hours after administration.

Intragastric administration group: rats were fasted overnight followed by intragastric administration (administration dosage was 10 mg/kg, and administration volume was 10 mL/kg), and ate 4 hours after administration.

3. Operation

Intravenous injection group: about 150 μL of blood was collected through jugular vein into EDTA-K2 anticoagulant tubes 0.083 hour, 0.25 hour, 0.5 hour, 1 hour, 2 hours, 4 hours, 8 hours and 24 hours after administration. The collected blood sample was placed on ice, and plasma was separated by centrifugation (centrifugation condition: 1500 g, 10 minutes). The collected plasma sample was stored at −40~−20° C. before analysis.

Intragastric administration group: about 100 μL of blood was collected through jugular vein into EDTA-K2 anticoagulant tubes 0.25 hour, 0.5 hour, 1 hour, 2 hours, 4 hours, 8 hours and 24 hours after administration. The collected blood sample was placed on ice, and plasma was separated by centrifugation (centrifugation condition: 1500 g, 10 minutes). The collected plasma sample was stored at −40~−20° C. before analysis.

LC-MS/MS was used to determine the content of the compound to be tested in rat plasma after intravenous injection and intragastric administration of the compound.

4. Results of Pharmacokinetic Parameters

The pharmacokinetic parameters of the compound of the present invention can be seen in the table below.

TABLE 7

Pharmacokinetic parameters of the compound of the present invention in rats

| Compound number | Pharmacokinetic parameters: Administration mode Administration dose | Plasma concentration $C_{max}$ (ng/mL) | Area under curve $AUC_{0-t}$ (ng · h/mL) | Half-life $T_{1/2}$ (h) | Bioavailability F (%) |
|---|---|---|---|---|---|
| 11 | Oral (10 mg/kg) | 1150 ± 349 | 4860 ± 1670 | 2.41 ± 2.11 | 79.4 |
| | injection (1 mg/kg) | N/A | 612 ± 126 | 0.73 ± 0.32 | |

Conclusion: the compound of the present invention has good pharmacokinetic properties in rats.

Test Example 8. Pharmacokinetic Evaluation of the Compound of the Present Invention in Dogs 1. Purpose of Experiment Beagle dogs were used as test animals, and LC/MS/MS was used to determine the drug concentrations at different moments in plasma of beagle dog by intravenous injection or intragastric administration of BI3406 and compound 11 of the present invention. The pharmacokinetic characteristics of compound 11 of the present invention in beagle dogs were studied.

2. Experimental Plan 2.1 Experimental Drugs

BI-3406 and compound 11 of the present invention, 2.2 Experimental Animals

Beagle, male, 13 to 14 months old, purchased from Beijing Mas Biotechnology Co., Ltd.

2.3 Preparation of Drugs

Intravenous injection group: an appropriate amount of the compound to be tested was weighed, and an appropriate amount of DMA:30% Solutol HS-15:Saline=5:5:90 (v/v/v) was added, vortexed, and a solution with a final concentration of 0.5 mg/mL was prepared.

Intragastric administration group: an appropriate amount of the compound to be tested was weighed, and an appropriate amount of DMA:30% Solutol HS-15:Saline=5:5:90 (v/v/v) was added, vortexed, and a solution with a final concentration of 1 mg/mL was prepared.

2.4 Administration

The beagle dogs were divided into intravenous injection group (3 dogs/group) and intragastric administration group (3 dogs/group) according to the compound to be tested.

Intravenous injection group: dogs were fasted overnight and then administered by intravenous injection (administration dosage was 0.5 mg/kg, and administration volume was 1 mL/kg), and ate 4 hours after administration.

Intragastric administration group: dogs were fasted overnight followed by intragastric administration (administration dosage was 10 mg/kg, and administration volume was 2 mL/kg), and ate 4 hours after administration.

3. Operation

Intravenous injection group: about 0.5 mL of blood was collected through jugular vein into EDTA-K2 anticoagulant tubes at 0.083 hour, 0.25 hour, 0.5 hour, 1 hour, 2 hours, 4 hours, 8 hours and 24 hours after administration. The collected blood sample was placed on ice, and plasma was separated by centrifugation (centrifugation condition: 1500 g, 10 minutes). The collected plasma sample was stored at −40~−20° C. before analysis.

Intragastric administration group: about 0.5 mL of blood was collected through jugular vein into EDTA-K2 anticoagulant tubes at 0.25 hour, 0.5 hour, 1 hour, 2 hours, 4 hours, 8 hours and 24 hours after administration. The collected blood sample was placed on ice, and plasma was separated by centrifugation (centrifugation condition: 1500 g, 10 minutes). The collected plasma sample was stored at −40~−20° C. before analysis.

LC-MS/MS was used to determine the content of the compound to be tested in dog plasma after intravenous injection and intragastric administration of the compound.

4. Results of Pharmacokinetic Parameters

The pharmacokinetic parameters of the compound of the present invention can be seen in the table below.

TABLE 8

Pharmacokinetic parameters of the compound of the present invention in dogs

| Compound number | Pharmacokinetic parameters: Administration mode Administration dose | Plasma concentration $C_{max}$ (ng/mL) | Area under curve $AUC_{0-t}$ (ng · h/mL) | Half-life $T_{1/2}$ (h) | Bioavailability F (%) |
|---|---|---|---|---|---|
| BI-3406 | Oral (2 mg/kg) | 180 ± 63.3 | 886 ± 339 | 3.49 ± 0.64 | N/A |
| 11 | Oral (2 mg/kg) | 456 ± 149 | 3510 ± 1750 | 4.21 ± 0.943 | 126.6 |
| | injection (0.5 mg/kg) | N/A | 693 ± 183 | 2.81 ± 0.45 | |

Conclusion: compared with the positive compound BI-3406, compound 11 of the present invention has higher plasma concentration and area under curve in beagle dogs at an oral dose of 2 mg/kg, and has good pharmacokinetic properties.

Note: BI-3406 was prepared through WO2018115380. The specific structure was as follows:

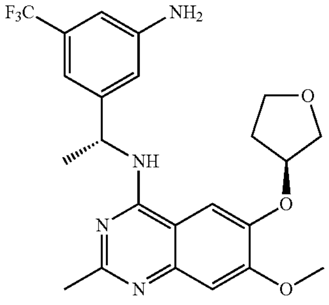

Test Example 9. Pharmacodynamic Evaluation of the Compound of the Present Invention in the Nude Mouse Subcutaneous Xenotransplanted Model of Human Lung Cancer NCI-H2122

1. Purpose of Experiment

The anti-tumor effect and safety of compound 11 of the present invention were evaluated in a Balb/c nude mouse animal model of subcutaneous xenotransplanted NCI-H2122.

2. Experimental Animals

BALB/c; nude mice, female, 6-7 weeks old (the age of mice when tumor cells were inoculated), purchased from Jiangsu Jicui Yaokang Biotechnology Co., Ltd.

3. Preparation of Test Substance

The solvent control group was given DMSO:castor oil:5% glucose injection=20:10:70 (v/v/v).

AMG-510: an appropriate amount of AMG-510 was weighed, and an appropriate amount of DMSO:castor oil: 5% glucose injection=20:10:70 (v/v/v) was added. After the above mixture was fully dissolved, an appropriate amount of 1 M hydrochloric acid was added, vortexed and mixed to prepare a solution with a concentration of 3 mg/mL.

Compound 11: an appropriate amount of compound 11 was weighed, and an appropriate amount of DMSO:castor oil:5% glucose injection=20:10:70 (v/v/v) was added. After the above mixture was fully dissolved, an appropriate amount of 1 M hydrochloric acid was added, vortexed and mixed to prepare a solution with a concentration of 3 mg/mL.

4. Cell Culture

H2122 cells were cultured in 1640 culture medium containing 10% fetal bovine serum and 1% penicillin-streptomycin-amphotericin B solution. H2122 cells in the exponential growth phase were collected and resuspended in matrigel solution (matrigel:PBS=1:1 (V/V)) to a suitable concentration for subcutaneous tumor inoculation in nude mice.

6. Animal Modeling and Random Grouping

Female Balb/c nude mice were subcutaneously inoculated with about $3.0\times10^6$H2122 cells on the right sides of their backs. When the average volume of the tumors reaches about 150-200 $mm^3$, the mice were randomly divided according to the tumor sizes with 6 mice in each group.

7. Animal Administration and Observation

Group 1 (G1), solvent control group;

Group 2 (G2), AMG-510 was given by intragastric administration at a dose of 30 mg/kg;

Group 3 (G3), Example 11 was given by intragastric administration at a dose of 30 mg/kg;

Group 4 (G4), AMG-510 and Example 11 were administered in combination, and the dosages were respectively: AMG-510, 30 mg/kg (QD); Example 11, 30 mg/kg (QD).

After tumor inoculation, routine monitoring included the effects of tumor growth and treatment on the normal behaviors of the animals, specifically the mobility, feeding and drinking, weight gain or loss, eyes, coat and other abnormalities of the experimental animals.

Calculation formulae for a relative tumor volume (RTV), a relative tumor proliferation rate (T/C) and a tumor inhibition percentage (IR) were as follows:

(1) TV (tumor volume)=½×a×$b^2$, wherein a and b represent the length and width of the tumor respectively;

(2) RTV (relative tumor volume)=$V_t/V_0$, wherein $V_0$ is the tumor volume measured at the time of administration when grouping (i.e. $d_0$), and $V_t$ is the tumor volume at each measurement;

(3) relative tumor proliferation rate T/C (%)=$T_{RTV}/C_{RTV}\times$ 100%, wherein $T_{RTV}$ is the RTV of the treatment group and $C_R$TV is the RTV of the control group;

(4) Tumor growth inhibition rate TGI (%)=(1−T/C)× 100%; wherein, T and C are the relative tumor volumes of the treatment group and the control group at a specific time point.

(5) IR (%)=(1−$TW_t/TW_c$)×100%, wherein, $TW_t$ is the tumor weight of the treatment group and $TW_c$ is the tumor weight of the control group. The anti-tumor evaluation criteria are (cytotoxic drugs): T/C (%)>40% is invalid; T/C (%)≤40%, and after statistical processing, P<0.05 is effective.

8. Results

TABLE 10

Changes in tumor volume of nude mice in each group with treatment time of the compounds of the present invention in the NCI-H2122 subcutaneous xenotransplanted tumor model

| Group | Days after Administration Tumor volume ($mm^3$) (x ± S) | | | | | |
|---|---|---|---|---|---|---|
| | Day 0 | Day 3 | Day 7 | Day 10 | Day 14 | Day 16 |
| solvent control group | 199 ± 21 | 332 ± 28 | 504 ± 70 | 641 ± 85 | 883 ± 129 | 1006 ± 168 |
| AMG-510 (30 mg/kg) | 199 ± 21 | 263 ± 17 | 343 ± 29 | 406 ± 38 | 538 ± 47 | 563 ± 58 |
| Example 11 (30 mg/kg) | 199 ± 18 | 329 ± 36 | 460 ± 53 | 551 ± 60 | 704 ± 88 | 757 ± 90 |

TABLE 10-continued

Changes in tumor volume of nude mice in each group with treatment time of the compounds of the present invention in the NCI-H2122 subcutaneous xenotransplanted tumor model

| Group | Days after Administration Tumor volume ($mm^3$) ($x \pm S$) | | | | | |
|---|---|---|---|---|---|---|
| | Day 0 | Day 3 | Day 7 | Day 10 | Day 14 | Day 16 |
| AMG-510 (30 mg/kg) + Example 11 (30 mg/kg) | 198 ± 27 | 240 ± 41 | 326 ± 42 | 335 ± 49 | 375 ± 56 | 387 ± 58 |

TABLE 11

Analysis of the efficacy of each group of the compounds of the present invention in the NCI-H2122 subcutaneous xenotransplanted tumor model

| Group | 16 days after administration | | |
|---|---|---|---|
| | Tumor volume (x ± S) | Relative tumor volume (x ± S) | TGI % |
| Solvent control group | 1006 ± 168 | 5.09 ± 0.69 | — |
| AMG-510 (30 mg/kg) | 563 ± 58 | 2.90 ± 0.26 | 43.0% |
| Example 11 (30 mg/kg) | 757 ± 90 | 4.03 ± 0.67 | 20.7% |
| AMG-510 (30 mg/kg) + Example 11 (30 mg/kg) | 387 ± 58 | 1.99 ± 0.18 | 60.8% |

TABLE 12

Tumor weight and inhibition rate of tumor weight of animals in each group at the end of the experiment

| Group | Tumor weight (g) (x ± S) | Inhibition rate of tumor weight (%) |
|---|---|---|
| Solvent control group | 0.7549 ± 0.0913 | — |
| AMG-510 (30 mg/kg) | 0.4203 ± 0.0447 | 44.3% |
| Example 11 (30 mg/kg) | 0.6283 ± 0.0663 | 16.8% |
| AMG-510 (30 mg/kg) + Example 11 (30 mg/kg) | 0.3045 ± 0.0536 | 60.0% |

Note:
Data were expressed as "mean ± standard error".

The changes in tumor volume of mice in each group in the NCI-H2122 model for the compounds of the present invention can be seen in FIG. 1. Conclusion: When the KRAS-G12C inhibitor non-sensitive cell line NCI-H2122 was used, under the combination with AMG-510, compound 11 has a good anti-tumor activity. Compared with the solvent control group, there was no significant change in the body weight of animals in each treatment group. No animals died during the experiment in both the drug administration group and the solvent control group, indicating that the animals had good drug tolerance under the experimental conditions.

The invention claimed is:

1. A compound represented by general formula (I) or a stereoisomer, a tautomer or a pharmaceutically acceptable salt thereof:

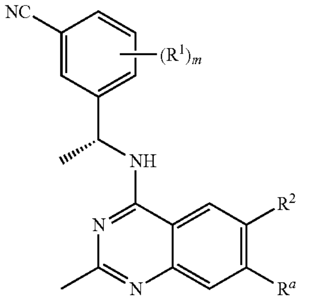

(I)

wherein:

$R^a$ is cyano, —C(O)$R^3$ or $C_1$-$C_6$ alkoxy;

$R^1$ are the same or different, and are each independently halogen, hydroxyl, amino, $C_1$-$C_6$ alkyl or $C_1$-$C_6$ alkoxy; wherein, the alkyl or alkoxy is optionally further substituted by one or more substituents selected from halogen, hydroxyl, cyano, amino, $C_1$-$C_6$ alkyl and $C_1$-$C_6$ alkoxy;

$R^2$ is $C_3$-$C_6$ cycloalkyl, 3-6 membered monocyclic heterocyclyl, 6-11 membered spiroheterocyclyl, 6-11 membered bridged heterocyclyl, 6-11 membered fused heterocyclyl or 6-11 membered fused ring; wherein, the cycloalkyl, monocyclic heterocyclyl, spiroheterocyclyl, bridged heterocyclyl, fused heterocyclyl or fused ring is optionally further substituted by one or more $R^A$s;

$R^A$ is each independently halogen, cyano, hydroxyl, amino, oxo, $C_1$-$C_6$ alkyl, $C_1$-$C_6$ alkoxy, $C_3$-$C_6$ cycloalkyl, 3-8 membered heterocyclyl, —C(O)$R^3$ or —$SO_2R^4$, wherein, the alkyl, alkoxy or cycloalkyl is optionally further substituted by one or more substituents selected from halogen, nitro, cyano, hydroxyl, amino, $C_1$-$C_6$ alkyl, $C_3$-$C_6$ cycloalkyl, $C_1$-$C_6$ alkoxy and —$SO_2R^4$; the heterocyclyl is optionally further substituted by one or more substituents selected from halogen, nitro, cyano, hydroxyl, amino, oxo, $C_1$-$C_6$ alkyl, $C_3$-$C_6$ cycloalkyl, $C_1$-$C_6$ alkoxy, —C(O)$R^3$ and —$SO_2R^4$;

$R^3$ is each independently $C_1$-$C_6$ alkyl, $C_1$-$C_3$ alkoxy, $C_3$-$C_6$ cycloalkyl, —$NR^5R^6$ or 3-6 membered heterocyclyl, wherein, the alkyl or cycloalkyl is optionally further substituted by one or more substituents selected from hydroxyl, halogen, nitro, amino, cyano, $C_1$-$C_6$ alkyl, $C_1$-$C_6$ alkoxy, $C_1$-$C_6$ haloalkyl and $C_1$-$C_6$ haloalkoxy; the heterocyclyl is optionally further substituted by one or more substituents selected from hydroxyl, halogen, nitro, amino, cyano, oxo, $C_1$-$C_6$ alkyl, $C_1$-$C_6$ alkoxy, $C_1$-$C_6$ haloalkyl and $C_1$-$C_6$ haloalkoxy;

$R^4$ is each independently amino, $C_1$-$C_6$ alkyl or $C_3$-$C_6$ cycloalkyl;

$R^5$ and $R^6$ are each independently a hydrogen atom or $C_1$-$C_6$ alkyl, wherein, the alkyl is optionally further substituted by one or more substituents selected from hydroxyl, halogen, amino, cyano and $C_1$-$C_6$ alkoxy;

or, $R^5$ and Re together with the N atom bound therewith form a 4-10 membered heterocyclic ring, the formed heterocyclic ring is optionally further substituted with a substituent selected from halogen, cyano, hydroxyl, amino, oxo, $C_1$-$C_6$ alkyl, $C_1$-$C_6$ alkoxy, —C(O)$R^7$ and $C_3$-$C_6$ cycloalkyl;

$R^7$ is $C_1$-$C_3$ alkyl or $C_3$-$C_6$ cycloalkyl, the alkyl or cycloalkyl is optionally further substituted by one or more substituents selected from hydroxyl, halogen, amino, cyano and $C_1$-$C_6$ alkoxy; and m is 0, 1, 2, 3 or 4.

2. The compound represented by general formula (I) or the stereoisomer, the tautomer, or the pharmaceutically acceptable salt thereof according to claim 1, which is a compound represented by general formula (II) or a stereoisomer, a tautomer, or a pharmaceutically acceptable salt thereof:

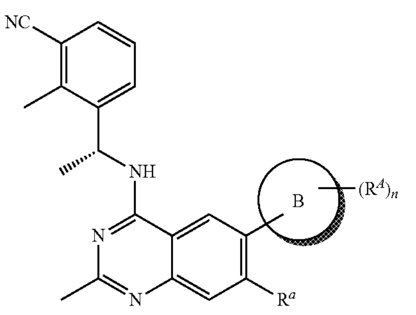

(II)

wherein:

$R^a$ is cyano, acetyl or methoxy;

ring B is $C_3$-$C_6$ cycloalkyl, 3-6 membered monocyclic heterocyclyl, 6-11 membered spiroheterocyclyl, 6-11 membered bridged heterocyclyl, 6-11 membered fused heterocyclyl or 6-11 membered fused ring;

$R^4$ is each independently halogen, cyano, hydroxyl, amino, oxo, $C_1$-$C_6$ alkyl, $C_1$-$C_6$ alkoxy, $C_3$-$C_6$ cycloalkyl, 3-8 membered heterocyclyl, —C(O)$R^3$ or —$SO_2R^4$, wherein, the alkyl, alkoxy or cycloalkyl is optionally further substituted by one or more substituents selected from halogen, nitro, cyano, hydroxyl, amino, $C_1$-$C_6$ alkyl, $C_3$-$C_6$ cycloalkyl, $C_1$-$C_6$ alkoxy and —$SO_2R^4$; the heterocyclyl is optionally further substituted by one or more substituents selected from halogen, nitro, cyano, hydroxyl, amino, oxo, $C_1$-$C_6$ alkyl, $C_3$-$C_6$ cycloalkyl, $C_1$-$C_6$ alkoxy, —C(O)$R^3$ and —$SO_2R^4$;

$R^3$ is $C_1$-$C_6$ alkyl, $C_1$-$C_3$ alkoxy, $C_3$-$C_6$ cycloalkyl, —$NR^5R^6$ or 3-6 membered heterocyclyl; wherein, the alkyl or cycloalkyl is optionally further substituted by one or more substituents selected from halogen, cyano and $C_1$-$C_6$ alkyl; the heterocyclyl is optionally further substituted by one or more substituents selected from halogen, cyano, oxo and $C_1$-$C_6$ alkyl;

$R^4$ is each independently amino, $C_1$-$C_6$ alkyl or $C_3$-$C_6$ cycloalkyl;

$R^5$ and $R^6$ are each independently a hydrogen atom or $C_1$-$C_6$ alkyl, wherein, the alkyl is optionally further substituted by one or more substituents selected from hydroxyl, halogen, amino, cyano and $C_1$-$C_6$ alkoxy;

or, $R^5$ and Re together with the N atom bound therewith form a 4-10 membered heterocyclic ring, the formed heterocyclic ring is optionally further substituted with a substituent selected from halogen, cyano, hydroxyl, amino, oxo, $C_1$-$C_6$ alkyl, $C_1$-$C_6$ alkoxy, —C(O)$R^7$ and $C_3$-$C_6$ cycloalkyl;

$R^7$ is $C_1$-$C_3$ alkyl or $C_3$-$C_6$ cycloalkyl, the alkyl or cycloalkyl is optionally further substituted by one or more substituents selected from hydroxyl, halogen, amino, cyano and $C_1$-$C_6$ alkoxy; and n is 0, 1, 2 or 3.

3. The compound or the stereoisomer, the tautomer, or the pharmaceutically acceptable salt thereof according to claim 2, wherein ring B is the following group:

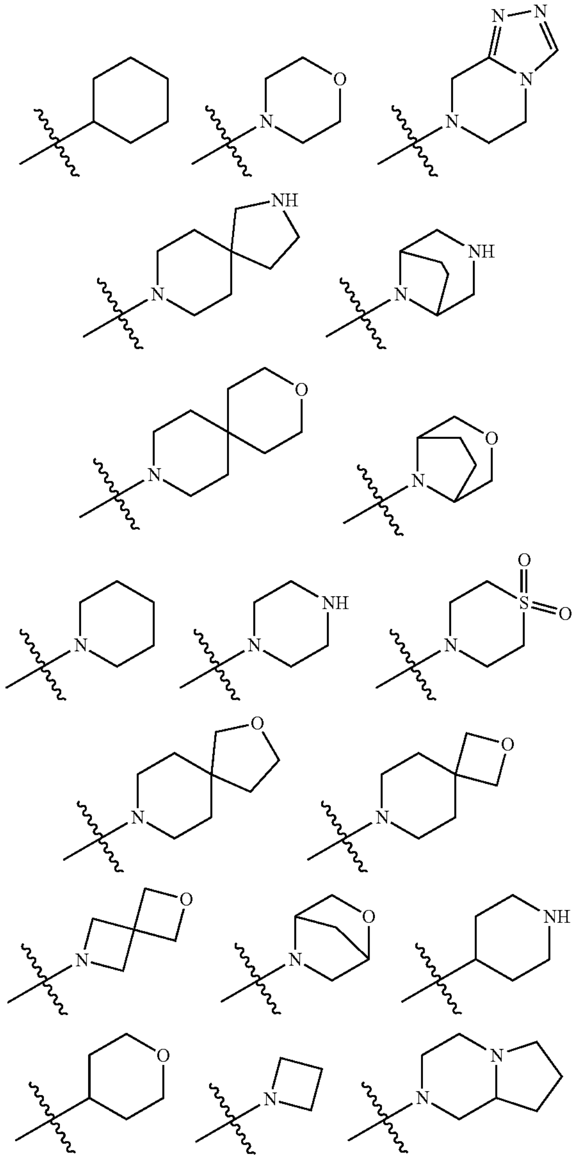

-continued
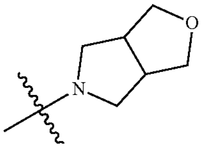
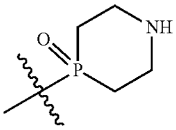
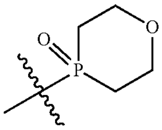
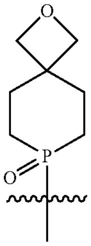
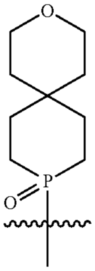
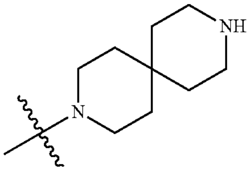
or
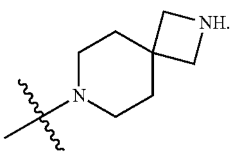
4. The compound or the stereoisomer, the tautomer, or the pharmaceutically acceptable salt thereof according to claim 2, wherein
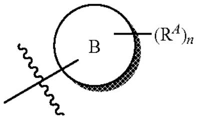
is the following group:
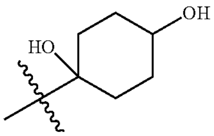
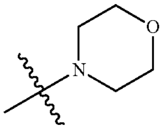
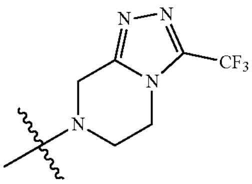
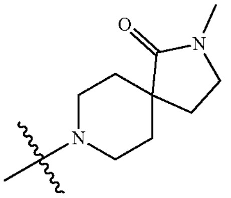
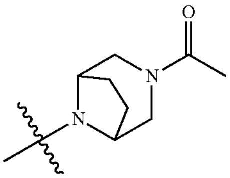
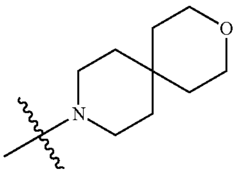
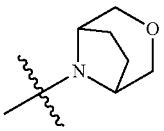
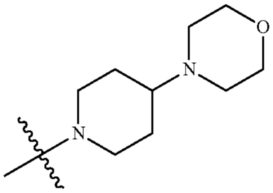
-continued
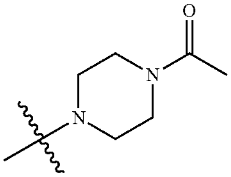
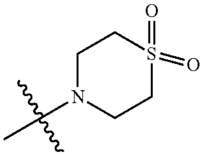
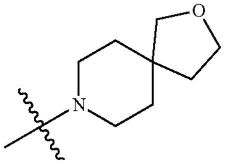
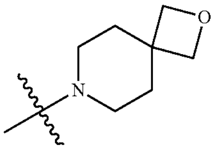
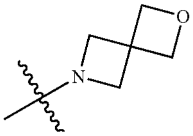
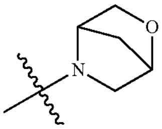
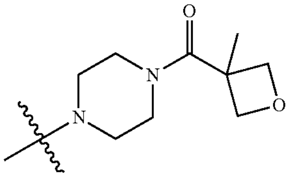
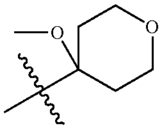
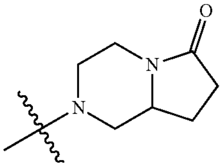
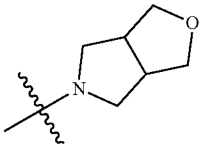
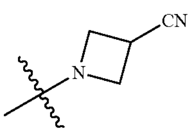
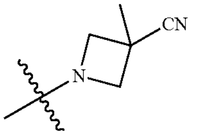
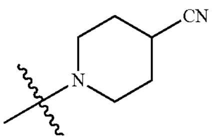
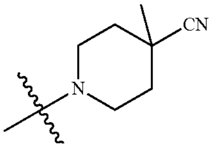
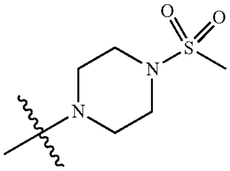
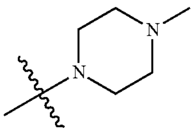
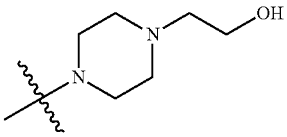
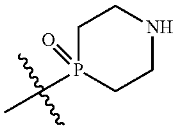
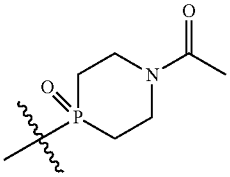
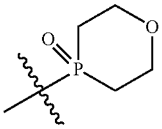

-continued
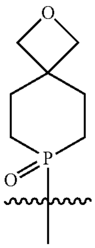
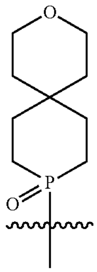
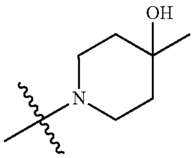
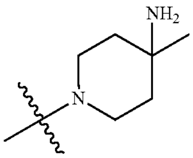
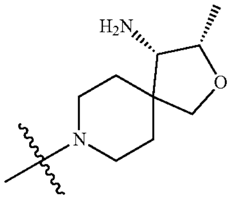
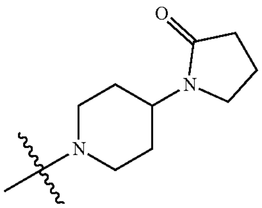
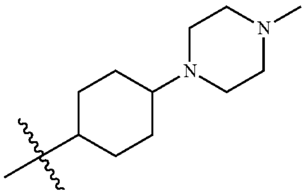
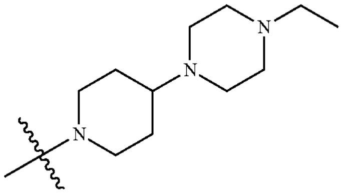
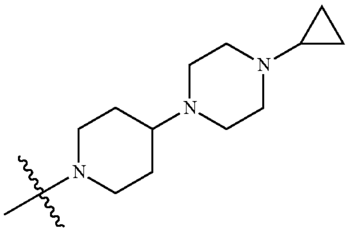
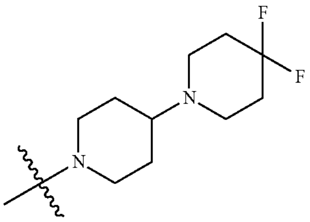
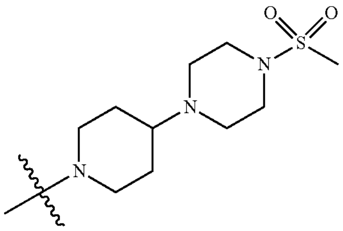
-continued
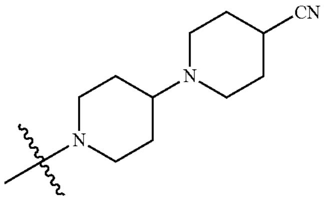
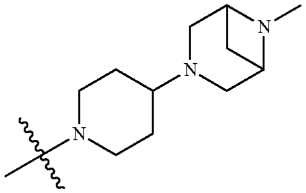
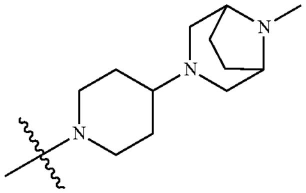
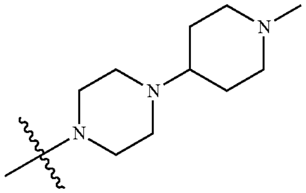
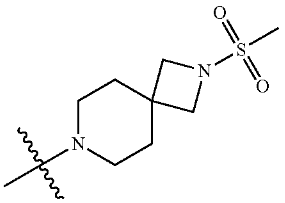
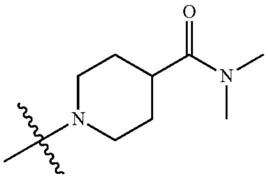
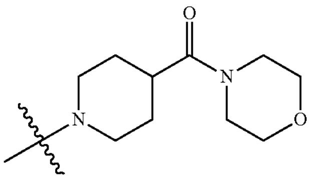
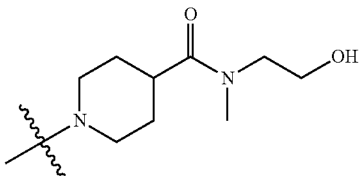
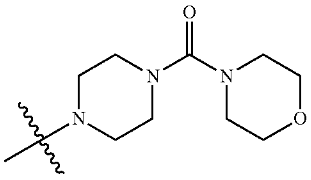

-continued

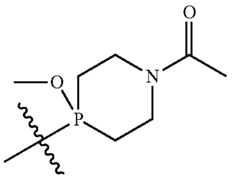

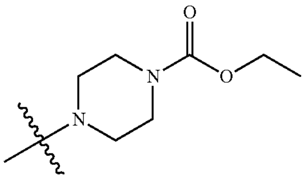

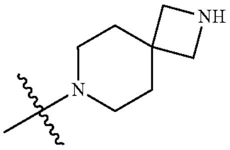

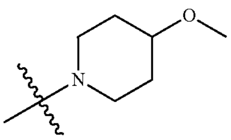

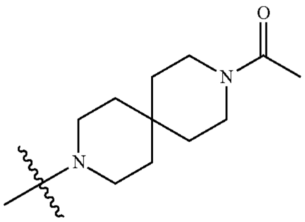

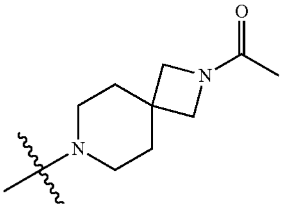

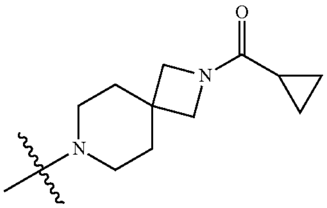

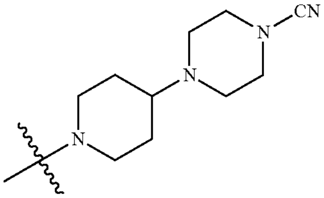

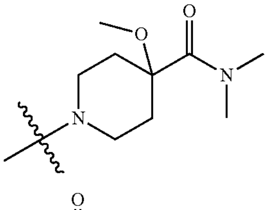

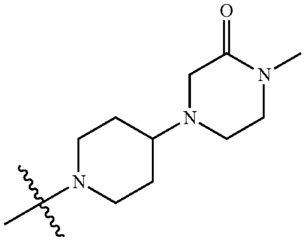

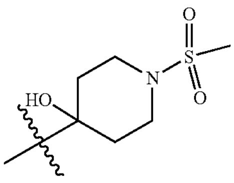

-continued

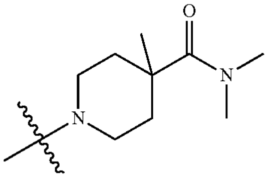

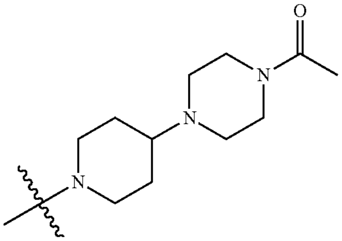

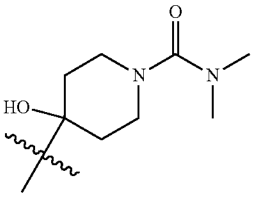

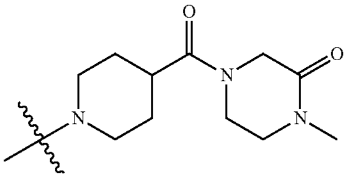

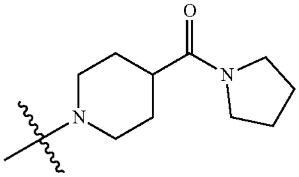

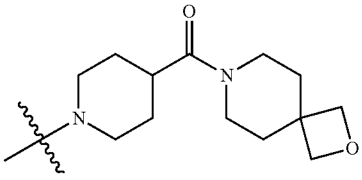

or

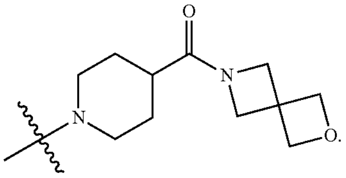

5. The compound or the stereoisomer, the tautomer, or the pharmaceutically acceptable salt thereof according to claim 1, wherein $R^1$ is methyl.

6. The compound or the stereoisomer, the tautomer, or the pharmaceutically acceptable salt thereof according to claim 1, wherein $R^a$ is methoxy.

7. The compound or the stereoisomer, the tautomer, or the pharmaceutically acceptable salt thereof according to claim 1, wherein $R^a$ is acetyl.

8. The compound or the stereoisomer, the tautomer, or the pharmaceutically acceptable salt thereof according to claim 1, wherein the compound is:

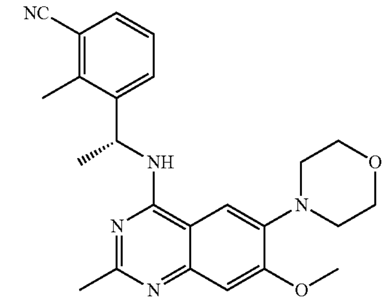
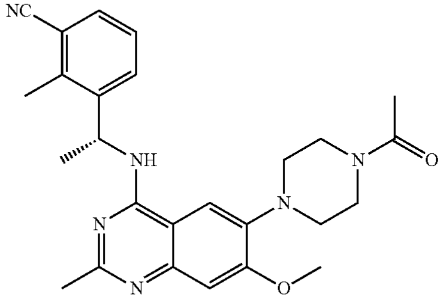
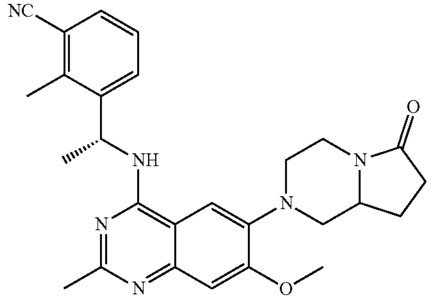
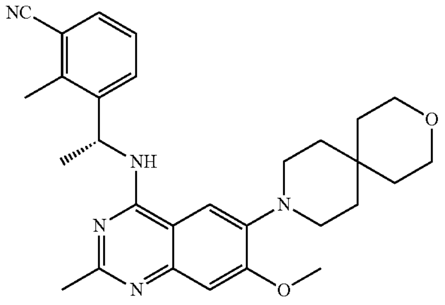
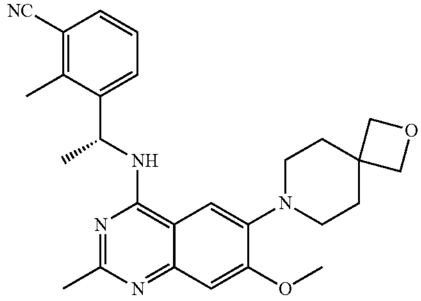
-continued
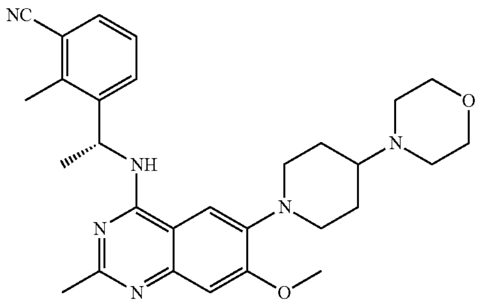
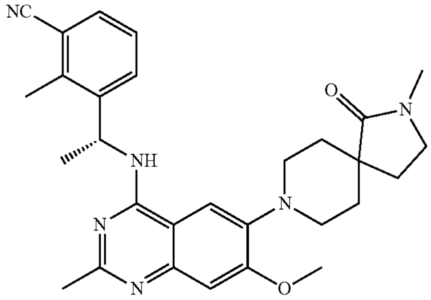
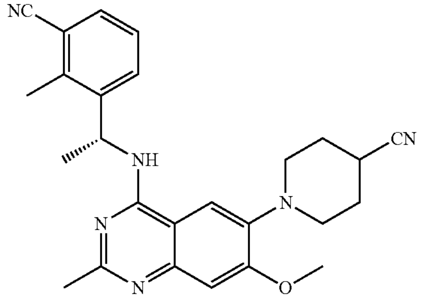
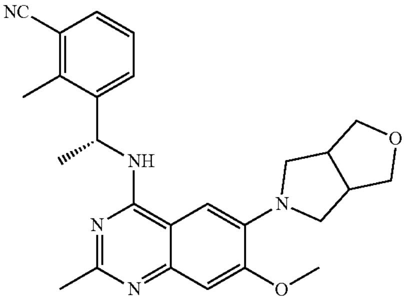
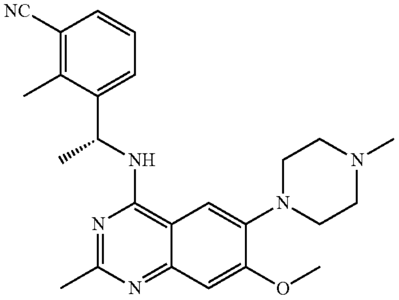

-continued
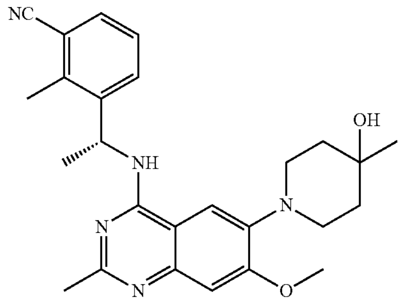
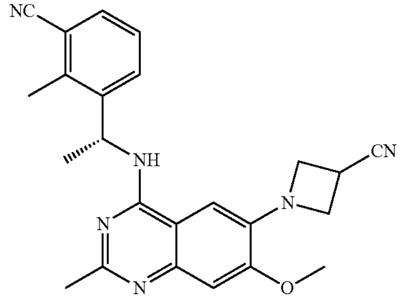
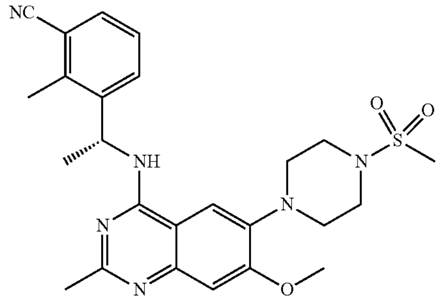
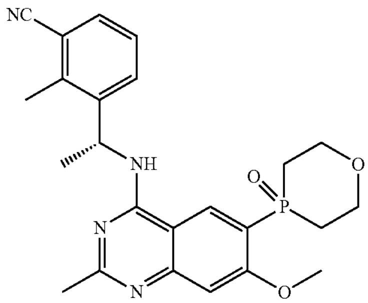
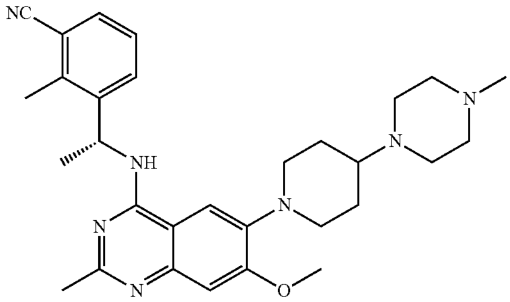
-continued
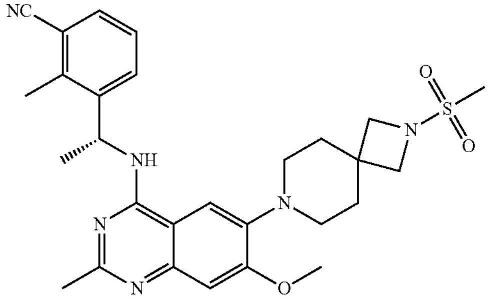
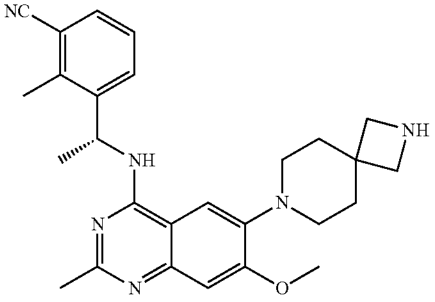
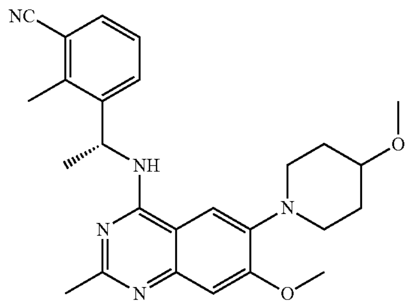
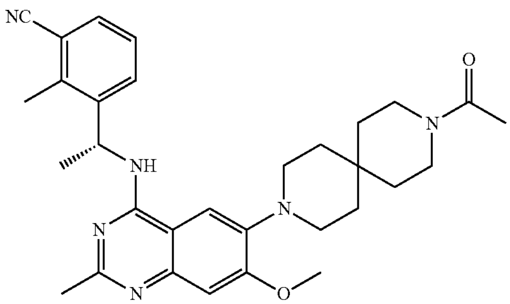
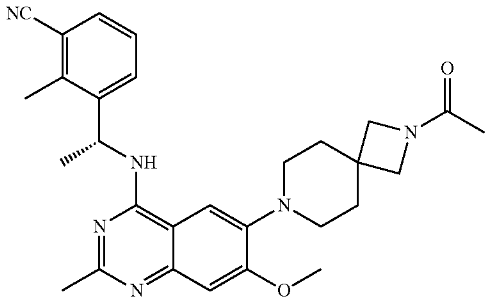

-continued
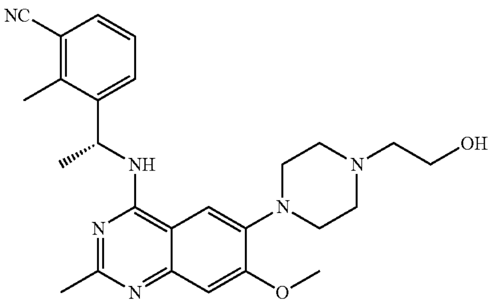
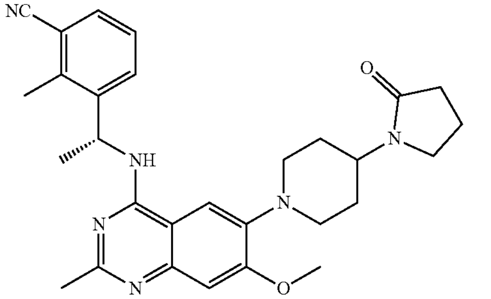
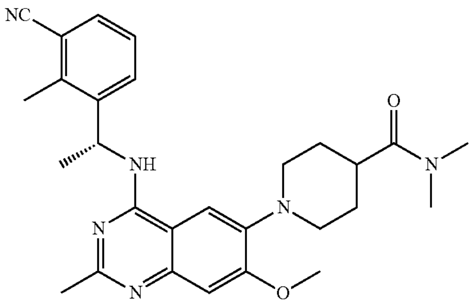
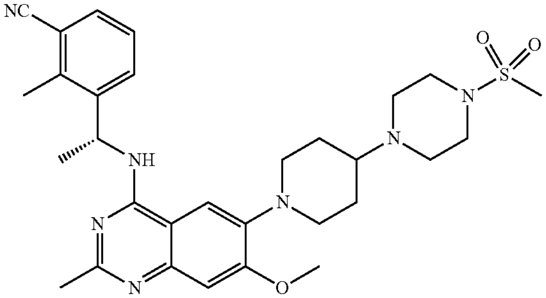
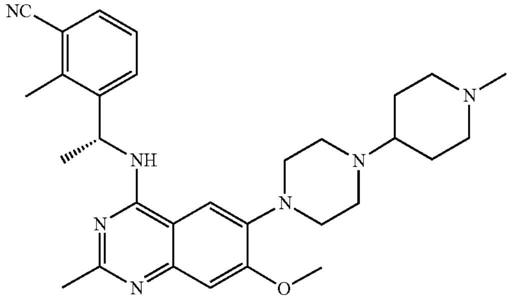
-continued
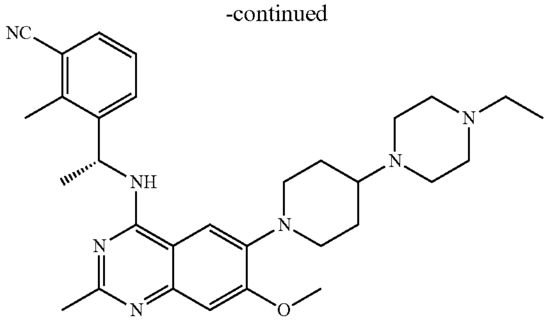
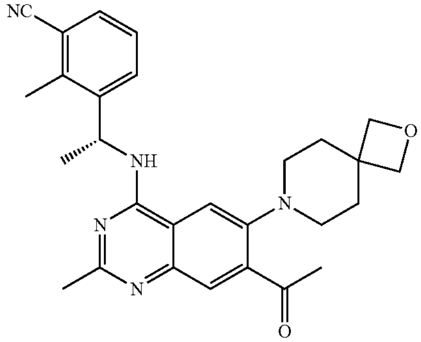
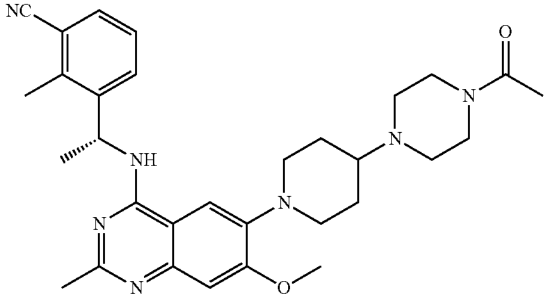
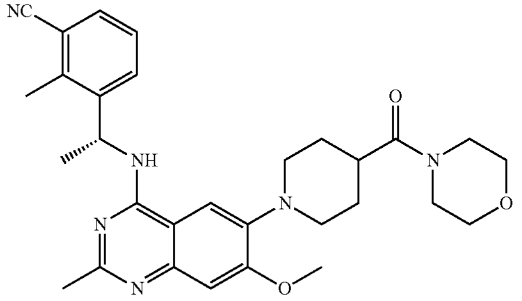
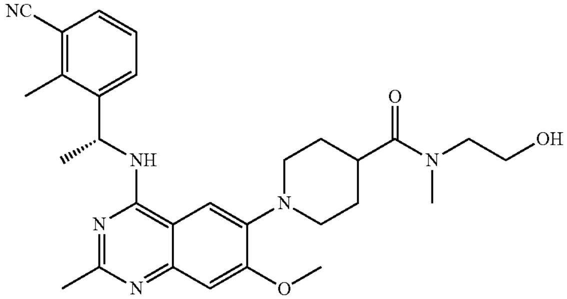

-continued
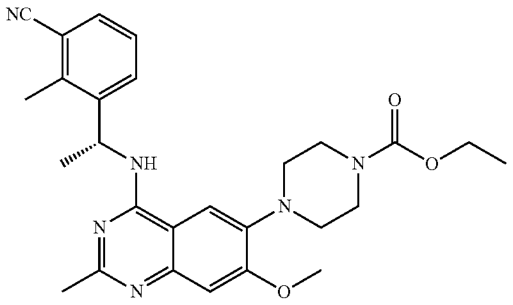
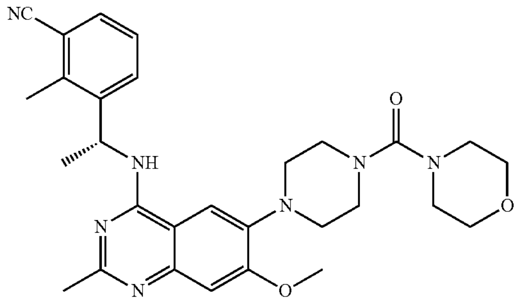
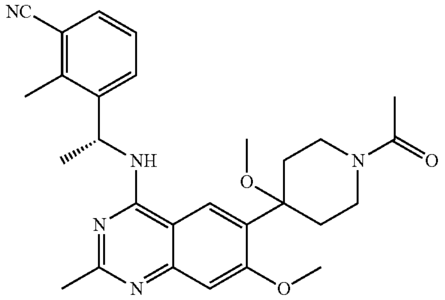
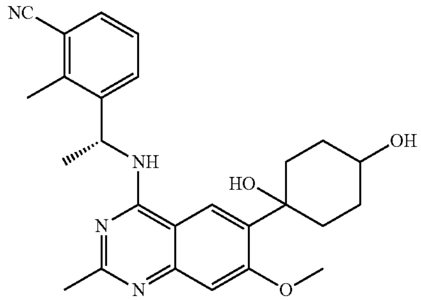
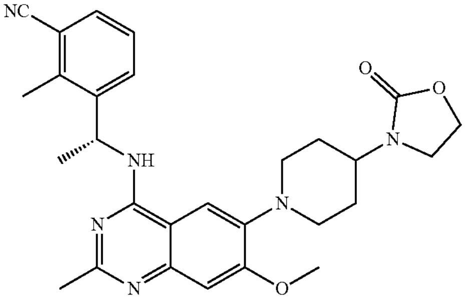
-continued
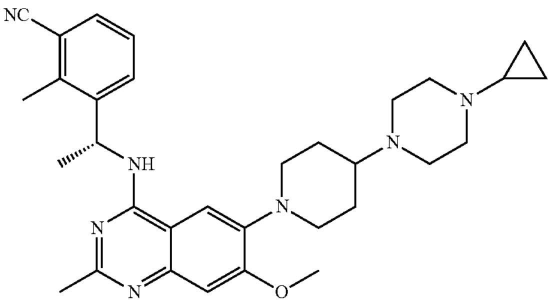
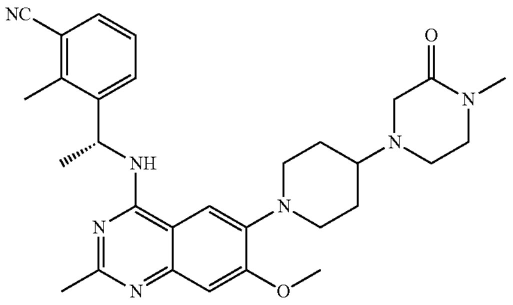
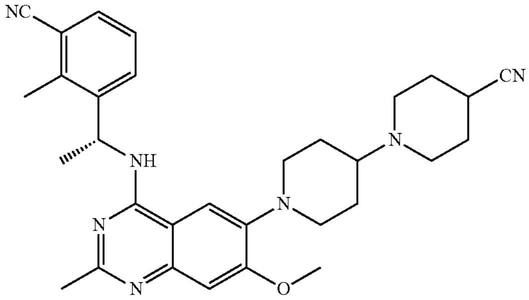
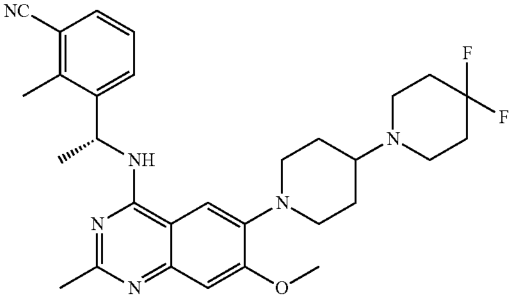
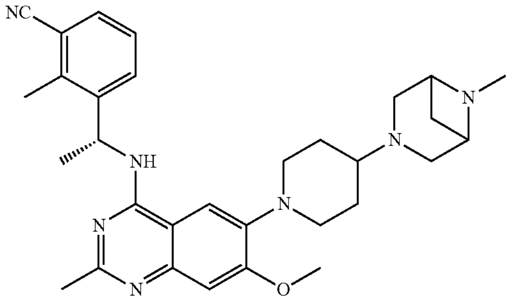

-continued
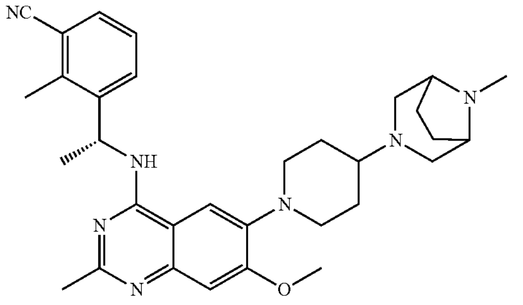
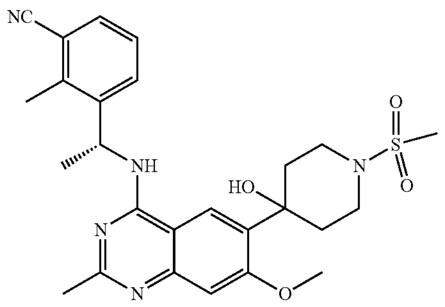
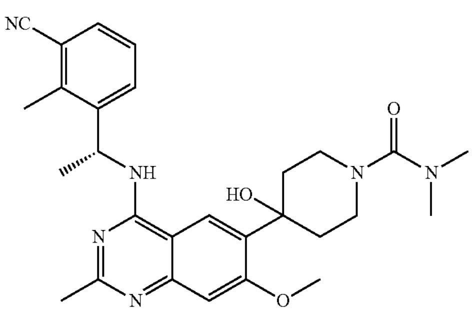
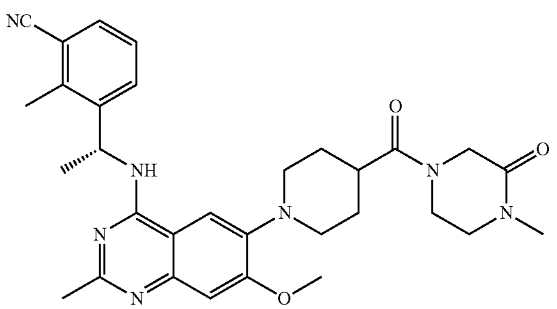
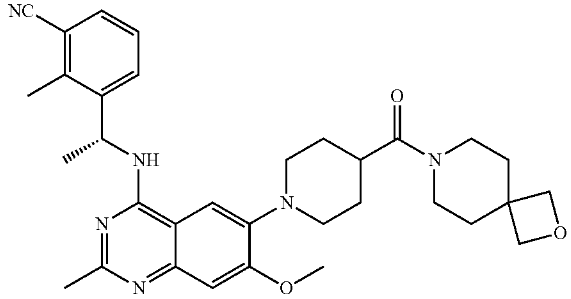 [SMILES: COc1cc2nc(C)nc(N[C@H](C)c3cccc(C#N)c3C)c2cc1N1CCC(C(=O)N2CCC3(CC2)COC3)CC1]
-continued
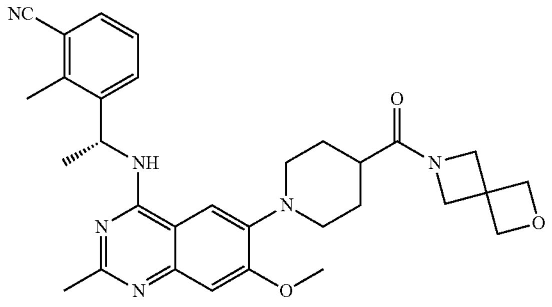 [SMILES: COc1cc2nc(C)nc(N[C@H](C)c3cccc(C#N)c3C)c2cc1N1CCC(C(=O)N2CC3(COC3)C2)CC1]
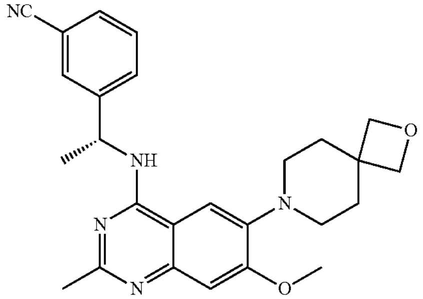
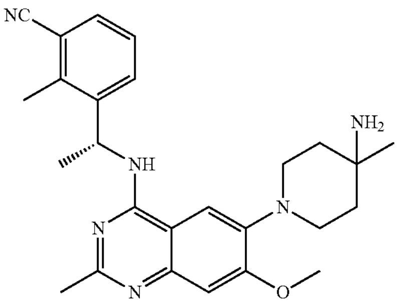
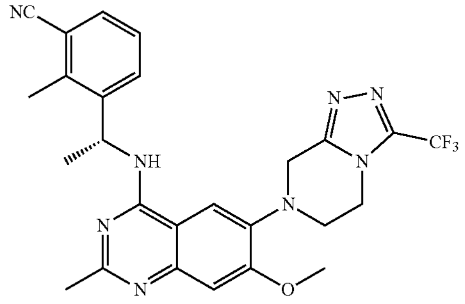
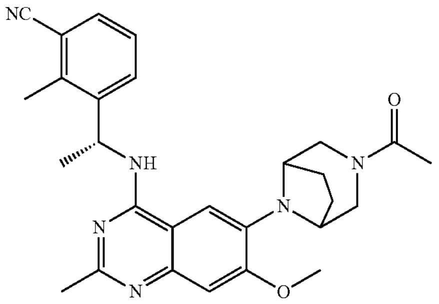

-continued
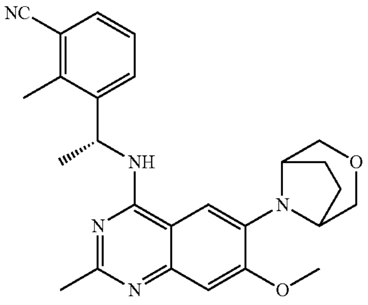
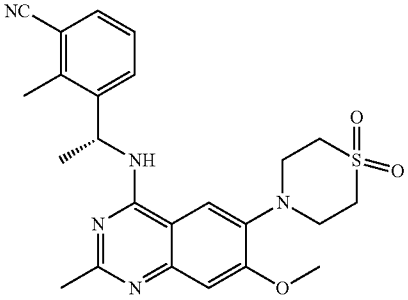
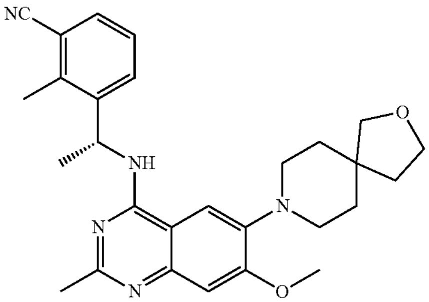
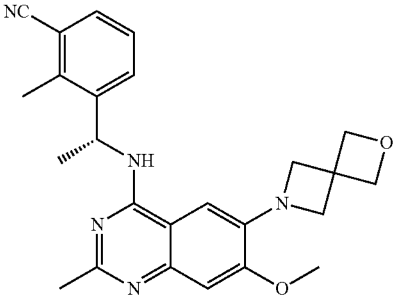
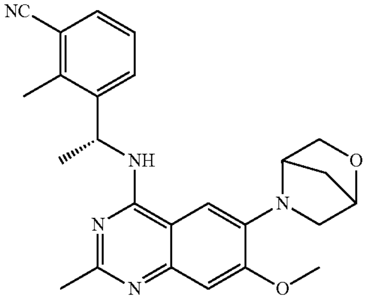
-continued
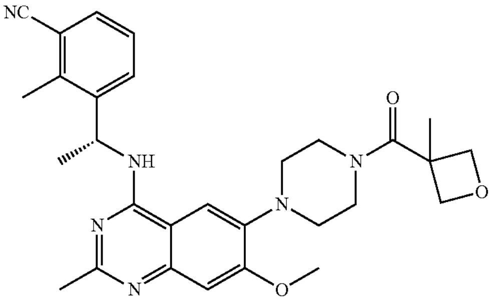
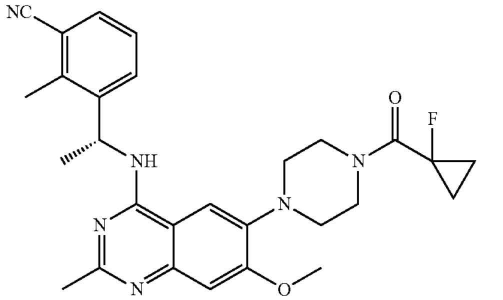
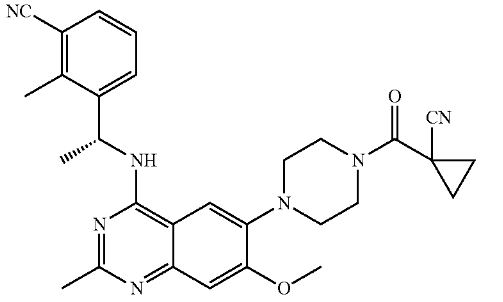
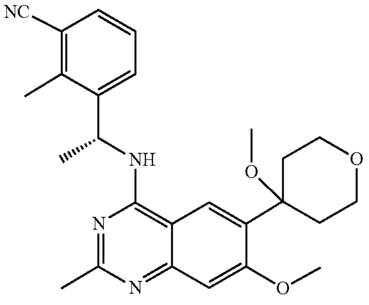
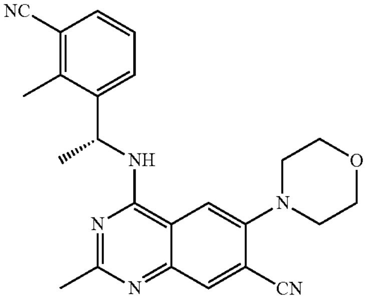

-continued

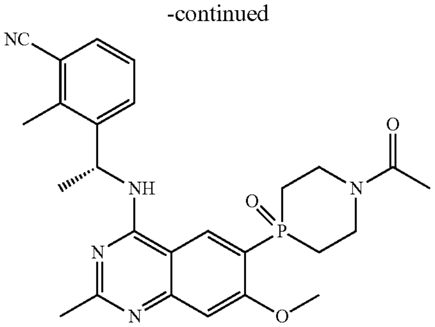

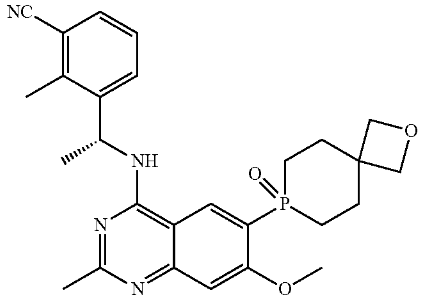

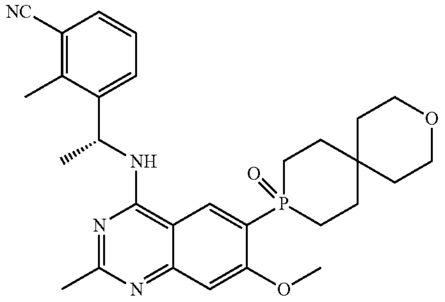

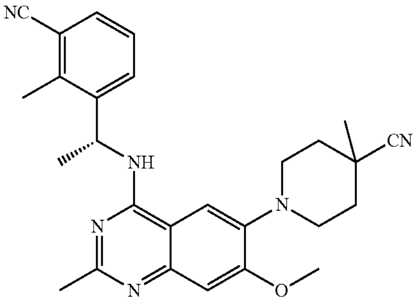

or

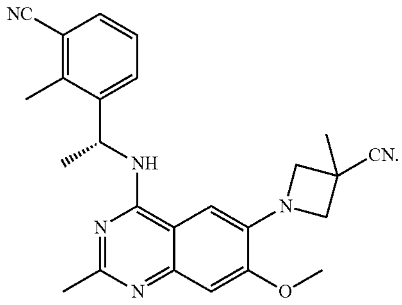

9. The compound or the stereoisomer, the tautomer, or the pharmaceutically acceptable salt thereof according to claim 1, wherein $R^1$ is $C_1$-$C_6$ alkyl.

10. The compound or the stereoisomer, the tautomer, or the pharmaceutically acceptable salt thereof according to claim 1, wherein $R^1$ is methyl.

11. The compound or the stereoisomer, the tautomer, or the pharmaceutically acceptable salt thereof according to claim 2, wherein $R^a$ is methoxy.

12. The compound or the stereoisomer, the tautomer, or the pharmaceutically acceptable salt thereof according to claim 2, wherein $R^a$ is acetyl.

13. The compound or the stereoisomer, the tautomer, or the pharmaceutically acceptable salt thereof according to claim 2, wherein the compound is:

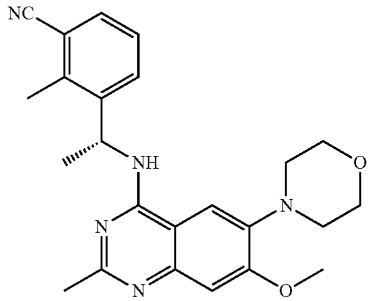

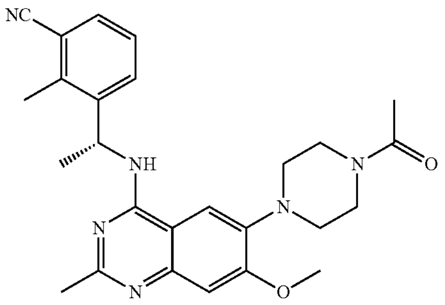

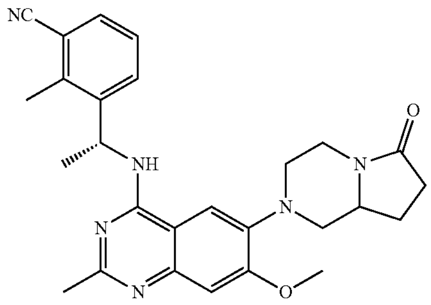

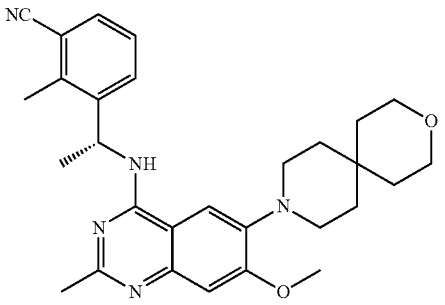

-continued
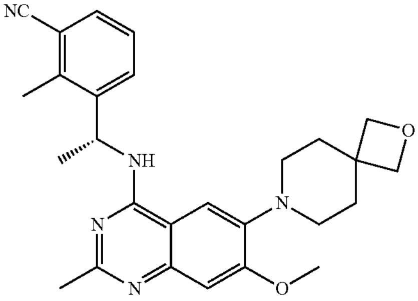
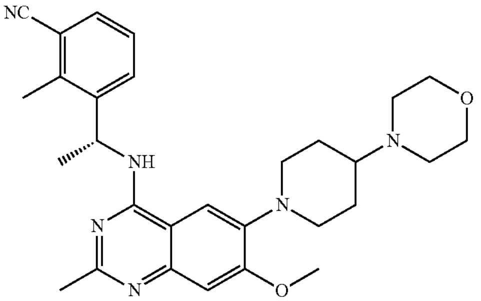
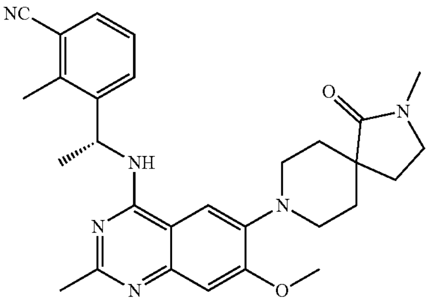
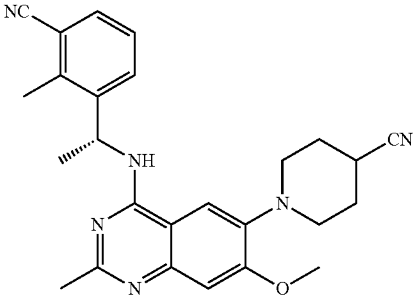
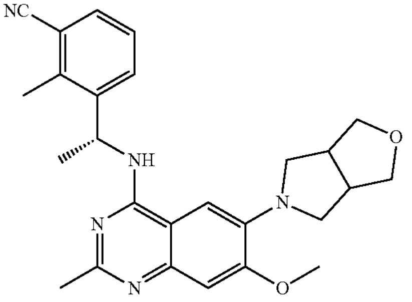
-continued
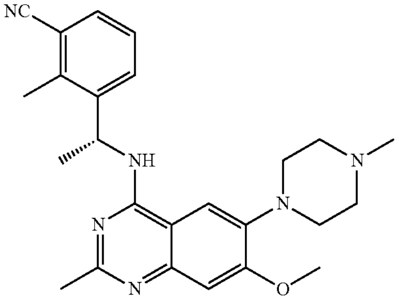
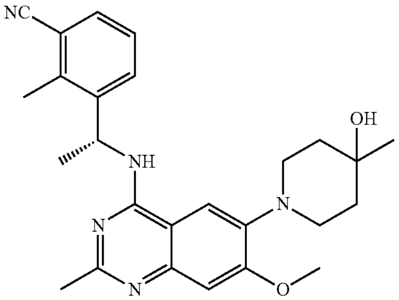
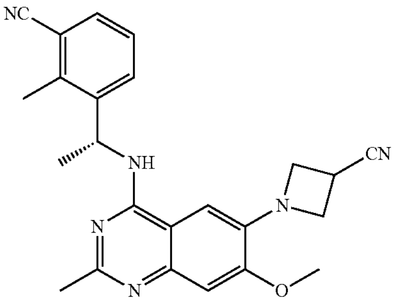
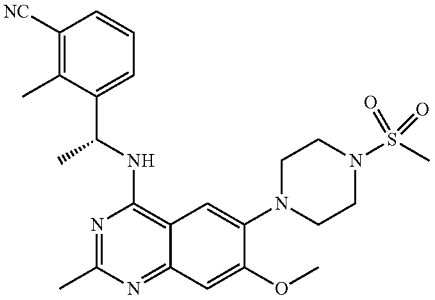
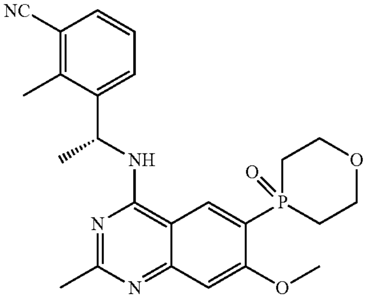

-continued
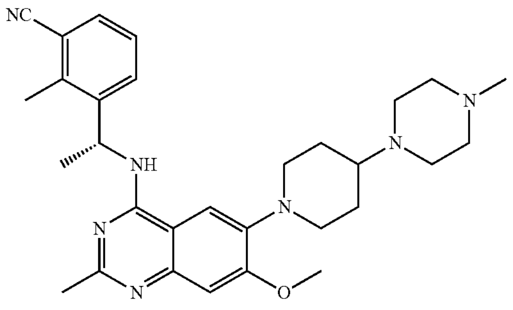
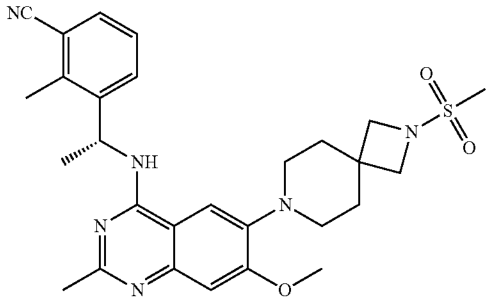
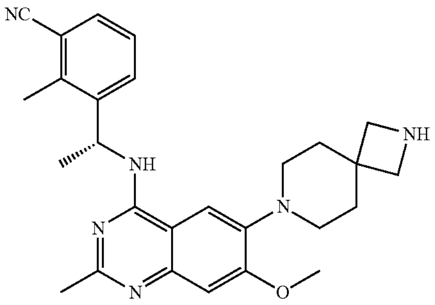
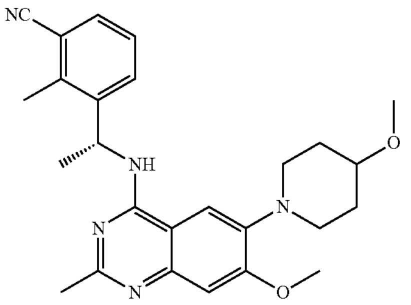
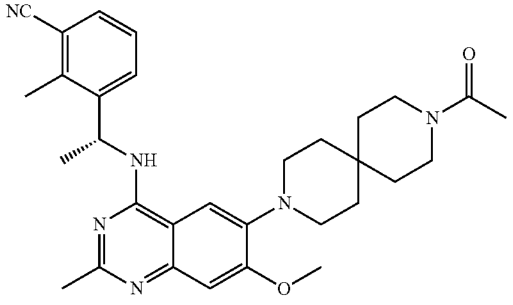
-continued
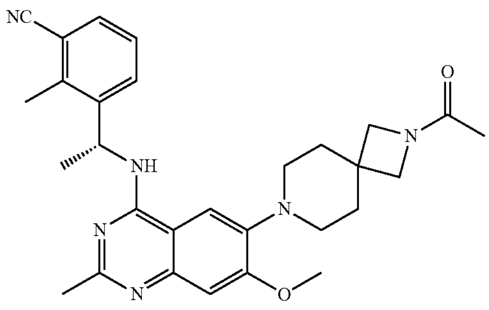
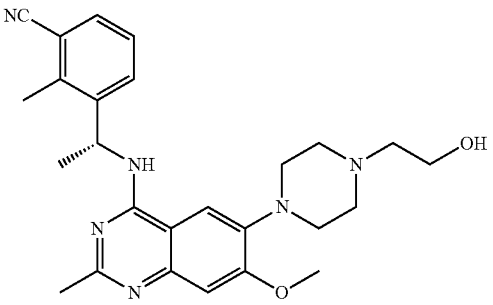
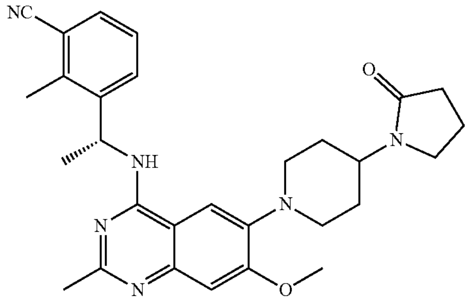
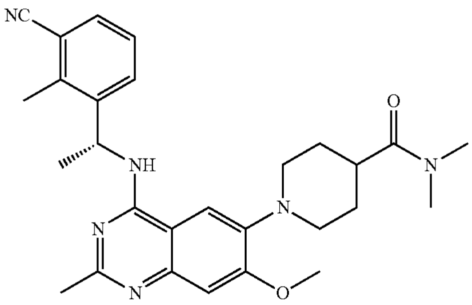
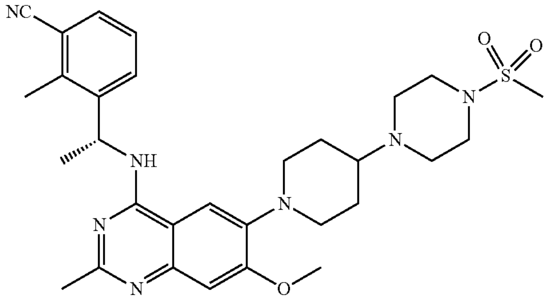

-continued
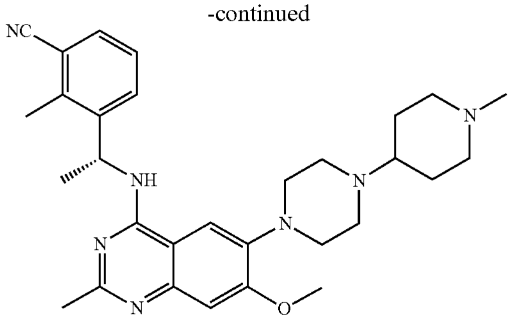
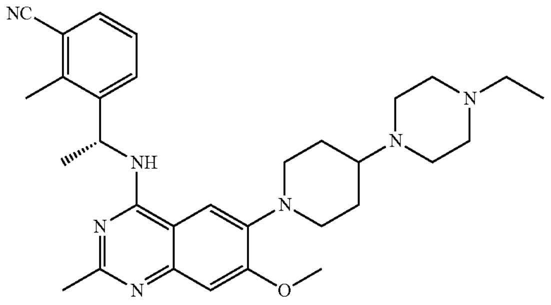
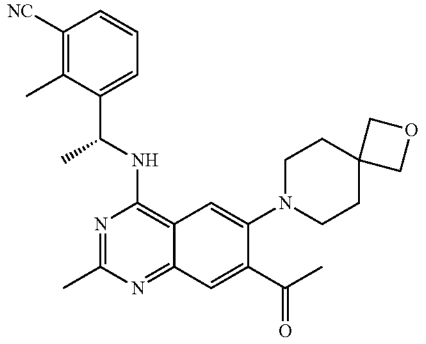
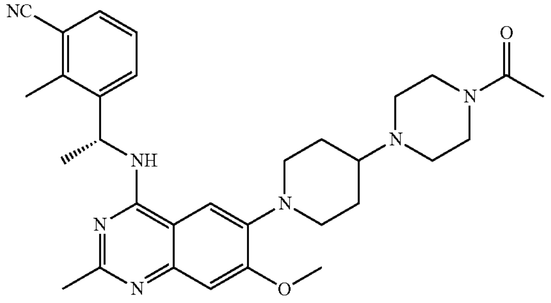
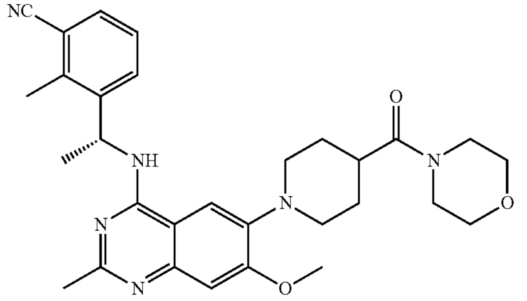
-continued
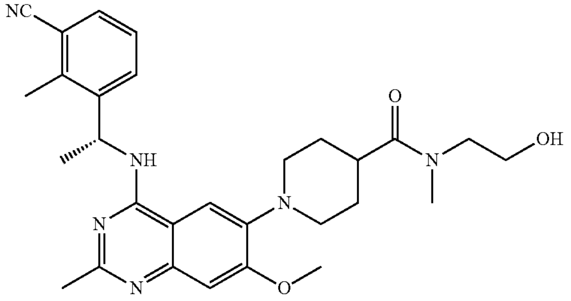
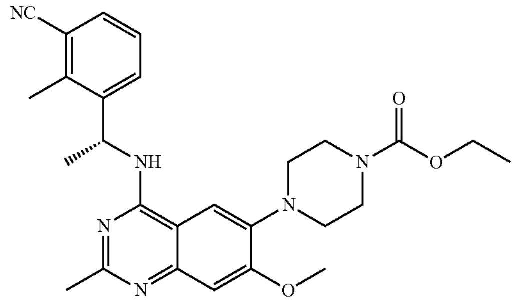
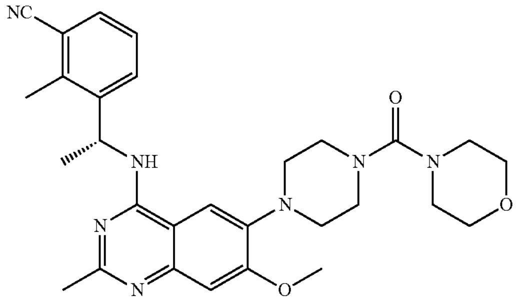
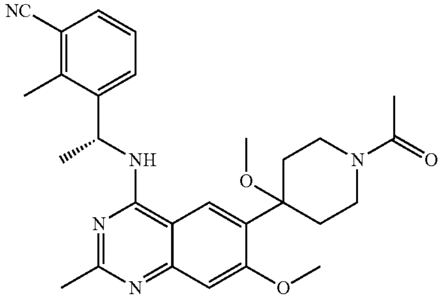
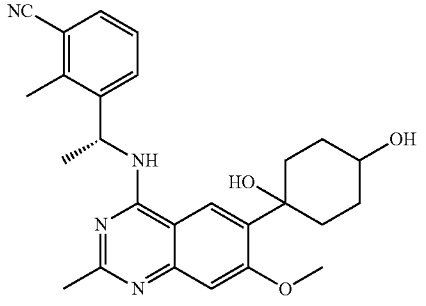

-continued
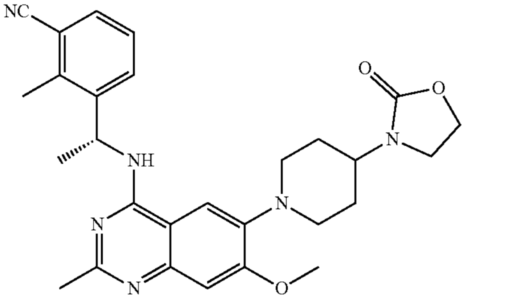
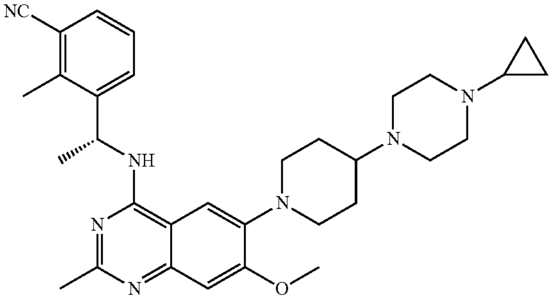
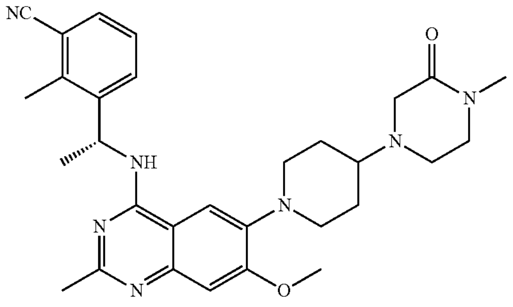
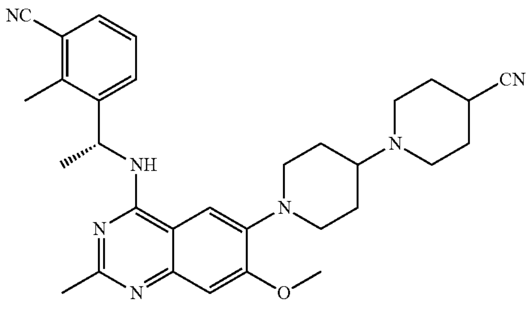
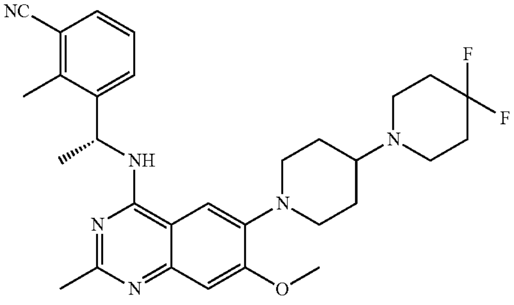
-continued
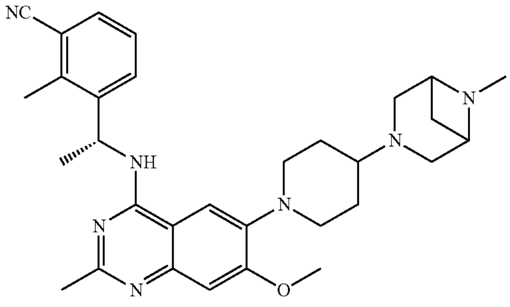
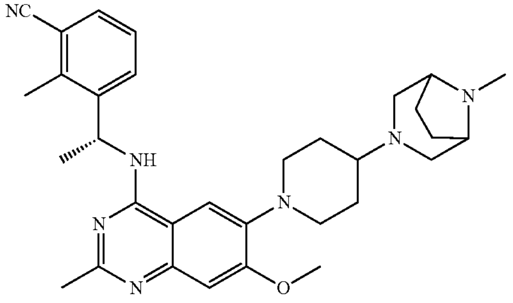
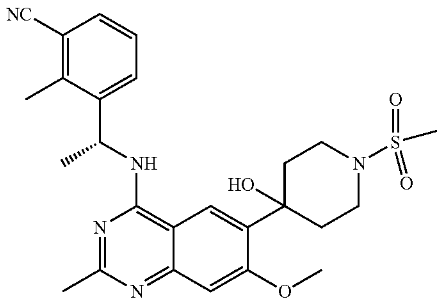
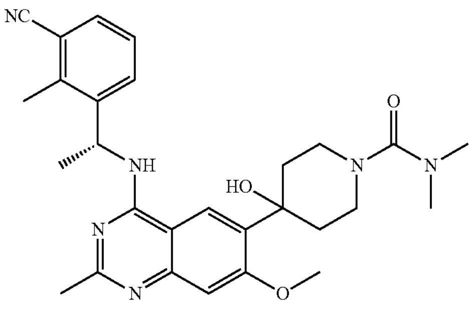
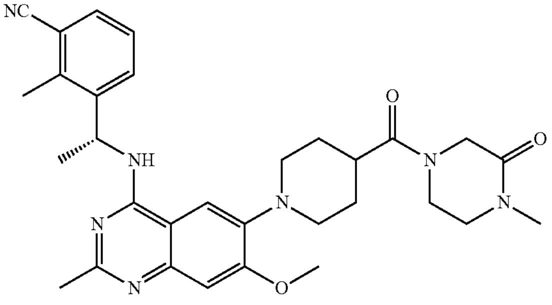

-continued
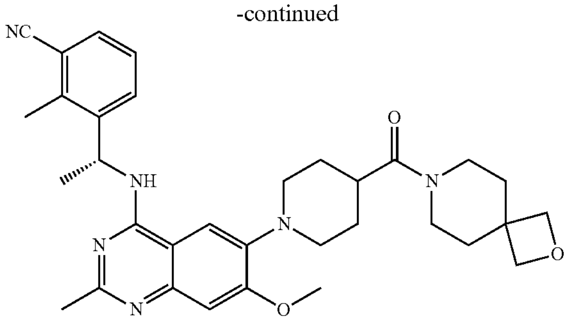
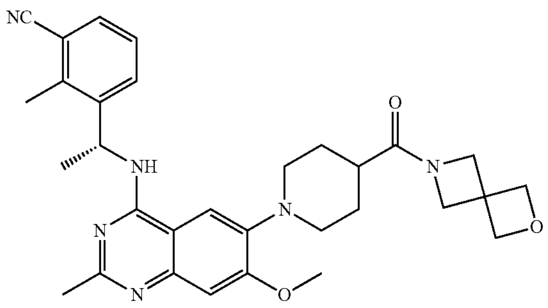
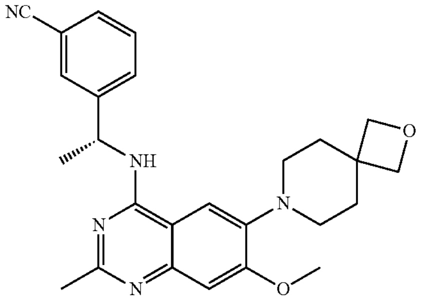
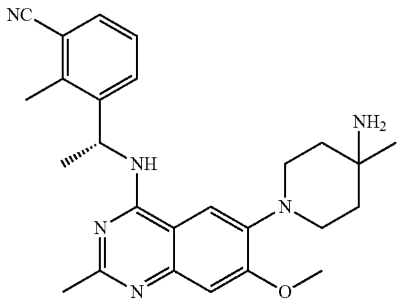
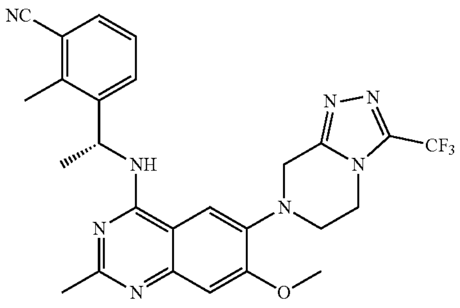
-continued
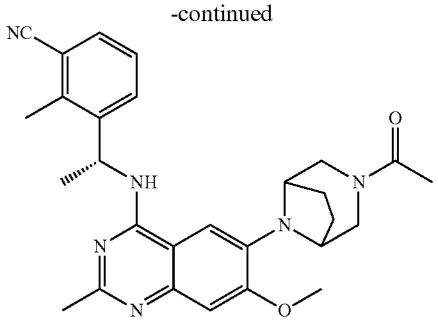
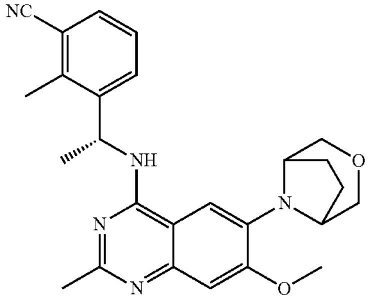
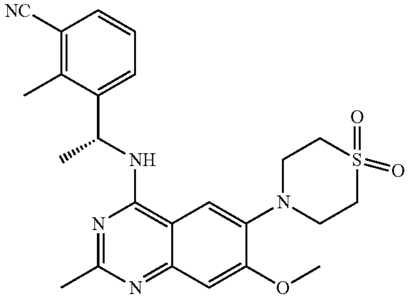
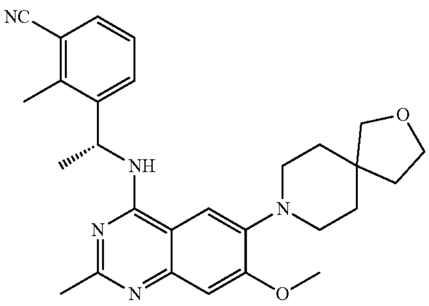
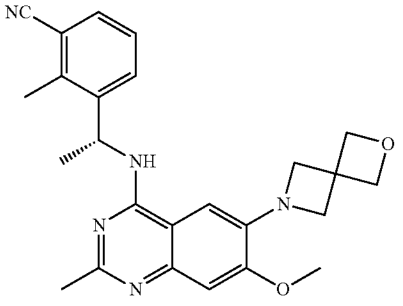

-continued
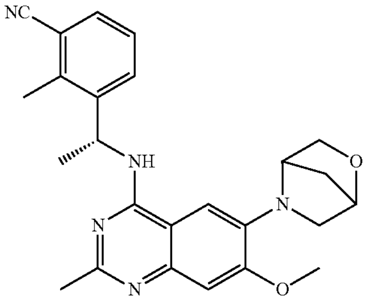
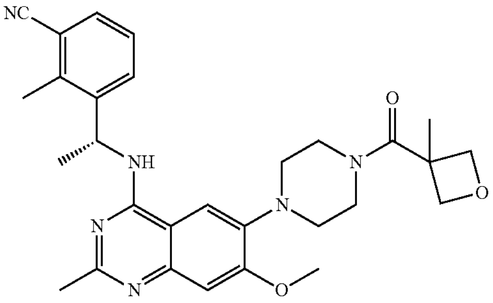
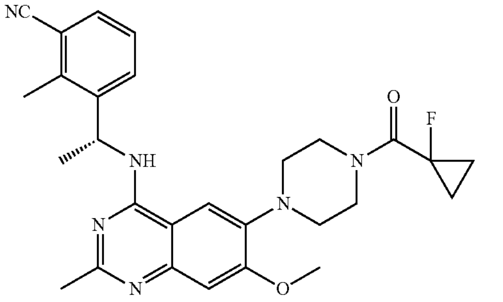
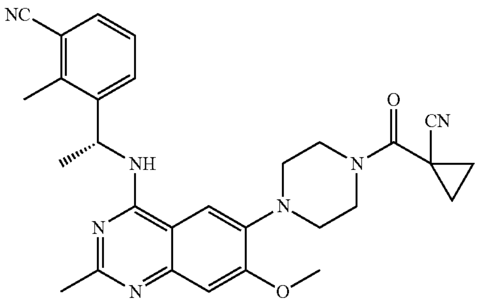
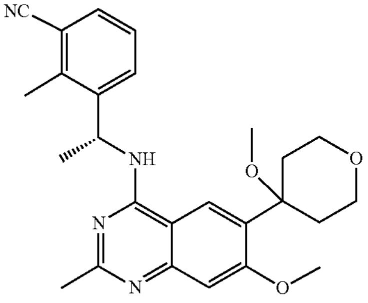
-continued
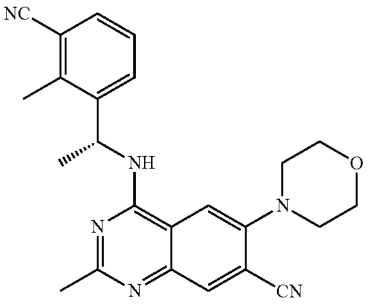
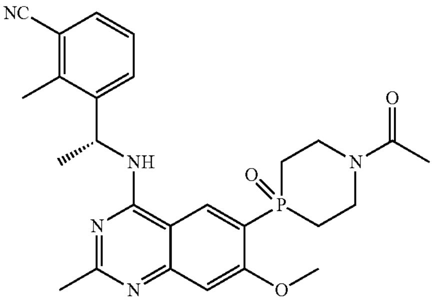
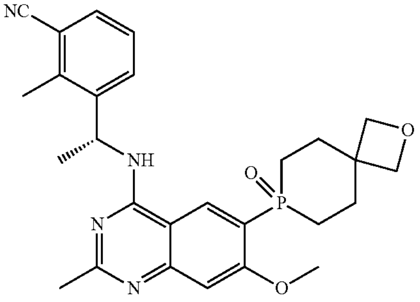
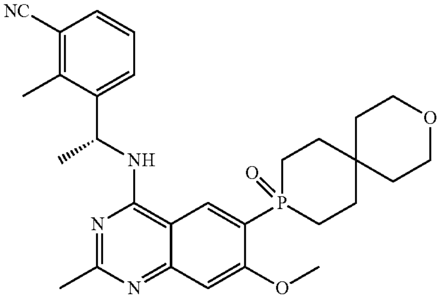
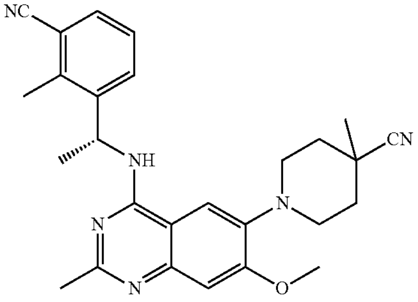
or -continued

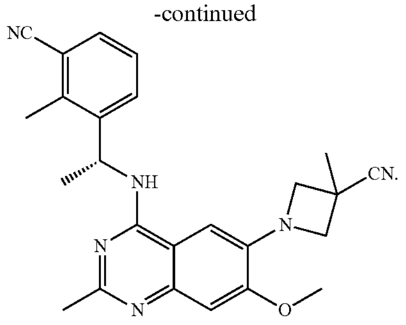

14. A pharmaceutical composition comprising an effective amount of the compound or the stereoisomer, the tautomer, or the pharmaceutically acceptable salt thereof according to claim 1, and a pharmaceutically acceptable carrier, an excipient or a combination thereof.

15. A composition comprising the compound or the stereoisomer, the tautomer, or the pharmaceutically acceptable salt thereof according to claim 1, or the pharmaceutical composition comprising an effective amount of the compound or the stereoisomer, the tautomer, or the pharmaceutically acceptable salt thereof according to claim 1, and other medicaments.

16. The composition according to claim 15, wherein the other medicaments are KRAS G12C inhibitors.

17. A method for inhibiting SOS1, comprising administering a therapeutically effective amount of the compound or the stereoisomer, the tautomer, or the pharmaceutically acceptable salt thereof according to claim 1, or the pharmaceutical composition comprising an effective amount of the compound or the stereoisomer, the tautomer, or the pharmaceutically acceptable salt thereof according to claim 1 to a subject in need thereof.

18. A method for treating a disease mediated by SOS1, comprising administering a therapeutically effective amount of the compound or the stereoisomer, the tautomer, or the pharmaceutically acceptable salt thereof according to claim 1, or the pharmaceutical composition comprising an effective amount of the compound or the stereoisomer, the tautomer, or the pharmaceutically acceptable salt thereof according to claim 1 to a subject in need thereof.

19. The method according to claim 18, wherein the disease mediated by SOS1 is lung cancer, pancreatic cancer, colon cancer, bladder cancer, prostate cancer, bile duct cancer, gastric cancer, diffuse large B-cell lymphoma, neurofibroma, Noonan syndrome, cardio-facio-cutaneous syndrome, type I hereditary gingival fibromatosis, embryonal rhabdomyosarcoma, Sertoli cell testicular tumor or cutaneous granular cell tumor.

20. The method according to claim 18, wherein the disease mediated by SOS1 is cancer related to signaling pathway dependence of RAS family proteins, cancer caused by SOS1 mutations, or hereditary disease caused by SOS1 mutations.

* * * * *